(12) United States Patent
Fujimura et al.

(10) Patent No.: US 8,871,304 B2
(45) Date of Patent: Oct. 28, 2014

(54) (AMIDE AMINO ALKANE) METAL COMPOUND, METHOD OF MANUFACTURING METAL-CONTAINING THIN FILM USING SAID METAL COMPOUND

(75) Inventors: Osamu Fujimura, Ube (JP); Hiroki Kanato, Ichihara (JP); Masashi Shirai, Ube (JP); Hiroshi Nihei, Ube (JP)

(73) Assignee: Ube Industries, Ltd., Ube-shi, Yamaguchi (JP)

( * ) Notice: Subject to any disclaimer, the term of this patent is extended or adjusted under 35 U.S.C. 154(b) by 0 days.

(21) Appl. No.: 13/882,824

(22) PCT Filed: Nov. 2, 2011

(86) PCT No.: PCT/JP2011/075347
§ 371 (c)(1),
(2), (4) Date: Jul. 5, 2013

(87) PCT Pub. No.: WO2012/060428
PCT Pub. Date: May 10, 2012

(65) Prior Publication Data
US 2013/0273250 A1    Oct. 17, 2013

(30) Foreign Application Priority Data

| Nov. 2, 2010 | (JP) | 2010-245941 |
|---|---|---|
| Jan. 5, 2011 | (JP) | 2011-000372 |
| Aug. 4, 2011 | (JP) | 2011-170697 |
| Sep. 5, 2011 | (JP) | 2011-192228 |

(51) Int. Cl.

| H01L 51/00 | (2006.01) |
|---|---|
| C07F 15/00 | (2006.01) |
| C07F 13/00 | (2006.01) |
| C07F 5/00 | (2006.01) |
| C07F 3/00 | (2006.01) |
| C07F 15/06 | (2006.01) |
| C07F 15/04 | (2006.01) |
| C07F 15/02 | (2006.01) |
| C07F 3/02 | (2006.01) |
| C07F 3/06 | (2006.01) |

(52) U.S. Cl.
CPC ........ *H01L 51/0083* (2013.01); *H01L 51/0084* (2013.01); *H01L 51/0077* (2013.01); *H01L 51/0089* (2013.01); *H01L 51/0092* (2013.01); *C07F 15/065* (2013.01); *C07F 15/045* (2013.01); *C07F 5/003* (2013.01); *C07F 15/025* (2013.01); *C07F 13/005* (2013.01); *C07F 3/02* (2013.01); *C07F 3/06* (2013.01)
USPC .......... 427/255.394; 564/512; 556/1; 556/45; 556/118; 556/138; 534/15

(58) Field of Classification Search
USPC ........... 556/1, 45, 118, 138; 564/512; 534/15; 427/255.394
See application file for complete search history.

(56) References Cited

U.S. PATENT DOCUMENTS

| 5,731,856 A | 3/1998 | Kim et al. |
|---|---|---|
| 5,744,864 A | 4/1998 | Cillessen et al. |

(Continued)

FOREIGN PATENT DOCUMENTS

| EP | 1737044 A | 12/2006 |
|---|---|---|
| EP | 2226847 A | 9/2010 |

(Continued)

OTHER PUBLICATIONS

Pohl, U.W., et al., "Synthesis and properties of zinc-nitrogen compounds for theMOVPE of p-type ZnSe", Journal of Crystal Growth, vol. 170, No. 1, Jan. 1997, pp. 144-148.

(Continued)

*Primary Examiner* — Porfirio Nazario Gonzalez
(74) *Attorney, Agent, or Firm* — Nixon Peabody LLP; Jeffrey L. Costellia

(57) ABSTRACT

The present invention relates to an (amide amino alkane) metal compound represented by the formula (1):

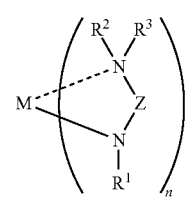

wherein
M represents a metal atom;
$R^1$ represents a linear, branched or cyclic alkyl group having 1 to 6 carbon atoms;
$R^2$ and $R^3$ may be the same as, or different from each other, and each independently represents a linear or branched alkyl group having 1 to 3 carbon atoms, or $R^2$ and $R^3$ may form a substituted or unsubstituted 5- or 6-membered ring together with the nitrogen atom to which they are bound;
Z represents a linear or branched alkylene group having 1 to 10 carbon atoms (a part of which may optionally form a ring); and
n represents a number of the ligands, which is equal to the valence of the metal (M), and represents an integer of from 1 to 3;
with the proviso that
the metal compounds in which M is Li (Lithium), Be (Beryllium), Ge (Germanium) or Nd (Neodymium) are excluded;
the metal compounds in which M is Mg (Magnesium) and $R^1$ is methyl group are excluded;
the metal compounds in which M is Zn (Zinc) and $R^1$ is methyl group are excluded;
the metal compounds in which M is Bi (Bismuth) and $R^1$ is t-butyl group are excluded; and
in cases where n is two or greater, two or more ligands may be the same as, or different from each other;
and a method of producing a metal-containing thin film using the metal compound.

8 Claims, 1 Drawing Sheet

(56) References Cited

U.S. PATENT DOCUMENTS

| | | |
|---|---|---|
| 5,908,947 A | 6/1999 | Vaartstra |
| 6,294,274 B1 | 9/2001 | Kawazoe et al. |
| 6,563,174 B2 | 5/2003 | Kawasaki et al. |
| 6,727,522 B1 | 4/2004 | Kawasaki et al. |
| 7,049,190 B2 | 5/2006 | Takeda et al. |
| 7,061,014 B2 | 6/2006 | Hosono et al. |
| 7,064,346 B2 | 6/2006 | Kawasaki et al. |
| 7,105,868 B2 | 9/2006 | Nause et al. |
| 7,211,825 B2 | 5/2007 | Shih et al |
| 7,282,782 B2 | 10/2007 | Hoffman et al. |
| 7,297,977 B2 | 11/2007 | Hoffman et al. |
| 7,323,356 B2 | 1/2008 | Hosono et al. |
| 7,385,224 B2 | 6/2008 | Ishii et al. |
| 7,402,506 B2 | 7/2008 | Levy et al. |
| 7,411,209 B2 | 8/2008 | Endo et al. |
| 7,453,065 B2 | 11/2008 | Saito et al. |
| 7,453,087 B2 | 11/2008 | Iwasaki |
| 7,462,862 B2 | 12/2008 | Hoffman et al. |
| 7,468,304 B2 | 12/2008 | Kaji et al. |
| 7,501,293 B2 | 3/2009 | Ito et al. |
| 7,674,650 B2 | 3/2010 | Akimoto et al. |
| 7,732,819 B2 | 6/2010 | Akimoto et al. |
| 2001/0046027 A1 | 11/2001 | Tai et al. |
| 2002/0056838 A1 | 5/2002 | Ogawa |
| 2002/0132454 A1 | 9/2002 | Ohtsu et al. |
| 2003/0189401 A1 | 10/2003 | Kido et al. |
| 2003/0218222 A1 | 11/2003 | Wager et al. |
| 2004/0038446 A1 | 2/2004 | Takeda et al. |
| 2004/0127038 A1 | 7/2004 | Carcia et al. |
| 2005/0017302 A1 | 1/2005 | Hoffman |
| 2005/0130417 A1 | 6/2005 | Ahn et al. |
| 2005/0199959 A1 | 9/2005 | Chiang et al. |
| 2006/0035452 A1 | 2/2006 | Carcia et al. |
| 2006/0043377 A1 | 3/2006 | Hoffman et al. |
| 2006/0091793 A1 | 5/2006 | Baude et al. |
| 2006/0108529 A1 | 5/2006 | Saito et al. |
| 2006/0108636 A1 | 5/2006 | Sano et al. |
| 2006/0110867 A1 | 5/2006 | Yabuta et al. |
| 2006/0113536 A1 | 6/2006 | Kumomi et al. |
| 2006/0113539 A1 | 6/2006 | Sano et al. |
| 2006/0113549 A1 | 6/2006 | Den et al. |
| 2006/0113565 A1 | 6/2006 | Abe et al. |
| 2006/0157863 A1 | 7/2006 | Marsh |
| 2006/0169973 A1 | 8/2006 | Isa et al. |
| 2006/0170111 A1 | 8/2006 | Isa et al. |
| 2006/0197092 A1 | 9/2006 | Hoffman et al. |
| 2006/0208977 A1 | 9/2006 | Kimura |
| 2006/0228974 A1 | 10/2006 | Thelss et al. |
| 2006/0231882 A1 | 10/2006 | Kim et al. |
| 2006/0238135 A1 | 10/2006 | Kimura |
| 2006/0244107 A1 | 11/2006 | Sugihara et al. |
| 2006/0284171 A1 | 12/2006 | Levy et al. |
| 2006/0284172 A1 | 12/2006 | Ishii |
| 2006/0292777 A1 | 12/2006 | Dunbar |
| 2007/0024187 A1 | 2/2007 | Shin et al. |
| 2007/0046191 A1 | 3/2007 | Saito |
| 2007/0052025 A1 | 3/2007 | Yabuta |
| 2007/0054507 A1 | 3/2007 | Kaji et al. |
| 2007/0090365 A1 | 4/2007 | Hayashi et al. |
| 2007/0108446 A1 | 5/2007 | Akimoto |
| 2007/0152217 A1 | 7/2007 | Lai et al. |
| 2007/0172591 A1 | 7/2007 | Seo et al. |
| 2007/0187678 A1 | 8/2007 | Hirao et al. |
| 2007/0187760 A1 | 8/2007 | Furuta et al. |
| 2007/0194379 A1 | 8/2007 | Hosono et al. |
| 2007/0252928 A1 | 11/2007 | Ito et al. |
| 2007/0272922 A1 | 11/2007 | Kim et al. |
| 2007/0287296 A1 | 12/2007 | Chang |
| 2008/0006877 A1 | 1/2008 | Mardilovich et al. |
| 2008/0038882 A1 | 2/2008 | Takechi et al. |
| 2008/0038929 A1 | 2/2008 | Chang |
| 2008/0050595 A1 | 2/2008 | Nakagawara et al. |
| 2008/0073653 A1 | 3/2008 | Iwasaki |
| 2008/0083950 A1 | 4/2008 | Pan et al. |
| 2008/0106191 A1 | 5/2008 | Kawase |
| 2008/0128689 A1 | 6/2008 | Lee et al. |
| 2008/0129195 A1 | 6/2008 | Ishizaki et al. |
| 2008/0166834 A1 | 7/2008 | Kim et al. |
| 2008/0182358 A1 | 7/2008 | Cowdery-Corvan et al. |
| 2008/0224133 A1 | 9/2008 | Park et al. |
| 2008/0254569 A1 | 10/2008 | Hoffman et al. |
| 2008/0258139 A1 | 10/2008 | Ito et al. |
| 2008/0258140 A1 | 10/2008 | Lee et al. |
| 2008/0258141 A1 | 10/2008 | Park et al. |
| 2008/0258143 A1 | 10/2008 | Kim et al. |
| 2008/0296568 A1 | 12/2008 | Ryu et al. |
| 2009/0068773 A1 | 3/2009 | Lai et al. |
| 2009/0073325 A1 | 3/2009 | Kuwabara et al. |
| 2009/0114910 A1 | 5/2009 | Chang |
| 2009/0134399 A1 | 5/2009 | Sakakura et al. |
| 2009/0152506 A1 | 6/2009 | Umeda et al. |
| 2009/0152541 A1 | 6/2009 | Maekawa et al. |
| 2009/0278122 A1 | 11/2009 | Hosono et al. |
| 2009/0280600 A1 | 11/2009 | Hosono et al. |
| 2010/0065844 A1 | 3/2010 | Tokunaga |
| 2010/0092800 A1 | 4/2010 | Itagaki et al. |
| 2010/0109002 A1 | 5/2010 | Itagaki et al. |
| 2012/0025380 A1 | 2/2012 | Neishi et al. |
| 2012/0219724 A1 | 8/2012 | Neishi et al. |

FOREIGN PATENT DOCUMENTS

| | | |
|---|---|---|
| JP | 60-198861 A | 10/1985 |
| JP | 63-210022 A | 8/1988 |
| JP | 63-210023 A | 8/1988 |
| JP | 63-210024 A | 8/1988 |
| JP | 63-215519 A | 9/1988 |
| JP | 63-239117 A | 10/1988 |
| JP | 63-265818 A | 11/1988 |
| JP | 05-251705 A | 9/1993 |
| JP | 08-264794 A | 10/1996 |
| JP | 11-505377 | 5/1999 |
| JP | 2000-044236 A | 2/2000 |
| JP | 2000-150900 A | 5/2000 |
| JP | 2002-076356 A | 3/2002 |
| JP | 2002-170993 | 6/2002 |
| JP | 2002-289859 A | 10/2002 |
| JP | 2003-031846 | 1/2003 |
| JP | 2003-086000 A | 3/2003 |
| JP | 2003-086808 A | 3/2003 |
| JP | 2004-103957 A | 4/2004 |
| JP | 2004-273614 A | 9/2004 |
| JP | 2004-273732 A | 9/2004 |
| JP | 2005-298874 | 10/2005 |
| JP | 2006-511716 | 4/2006 |
| JP | 2009-277357 | 11/2009 |
| JP | 2010-156058 | 7/2010 |
| JP | 2010-524264 | 7/2010 |
| KR | 10-0958335 B1 | 5/2010 |
| WO | WO 2004/046417 A2 | 6/2004 |
| WO | WO-2004/114391 | 12/2004 |
| WO | WO 2008/111499 A1 | 9/2008 |
| WO | WO-2008/128141 A2 | 10/2008 |
| WO | WO 2009/088522 A2 | 7/2009 |
| WO | WO 2009/117670 A2 | 9/2009 |
| WO | WO 2010/116889 A1 | 10/2010 |
| WO | WO 2011/037090 A1 | 3/2011 |
| WO | WO 2011/050073 A1 | 4/2011 |

OTHER PUBLICATIONS

Vehkamaki, Marko, et al., "Bismuth precursors for atomic layer deposition of bismuthcontainingoxide films", J. Mater. Chem., 14, Sep. 22, 2004, pp. 3191-3197.

Bell, N.A., "Some Oxy-, Amino-, andThio-beryllium Complexes", J. Chem. Soc. (A), 1966, pp. 542-544.

Fortunato.E et al., "Wide-Bandgap High-Mobility ZNO Thin-Film Transistors Produced At Room Temperature,", Appl. Phys. Lett. (Applied Physics Letters) , Sep. 27, 2004, vol. 85, No. 13, pp. 2541-2543.

Dembo.H et al., "RFCPUS on Glass and Plastic Subtrates Fabricated by TFT Transfer Technology,", IEDM 05: Technical Digest of International Electron Devices Meeting, Dec. 5, 2005, pp. 1067-1069.

(56) References Cited

OTHER PUBLICATIONS

Ikeda.T et al., "Full-Functional System Liquid Crystal Display Using CG-Silicon Technology,", SID Digest '04 : SID International Symposium Digest of Technical Papers, 2004, vol. 35, pp. 860-863.

Nomura.K et al., "Room-Temperature Fabrication of Transparent Flexible Thin-Film Transistors Using Amorphous Oxide Semiconductors,", Nature, Nov. 25, 2004, vol. 432, pp. 488-492.

Park.J et al., "Improvements in the Device Characteristics of Amorphous Indium Gallium Zinc Oxide Thin-Film Transistors By Ar Plasma Treatment,", Appl. Phys. Lett. (Applied Physics Letters) , Jun. 26, 2007, vol. 90, No. 26, pp. 262106-1-262106-3.

Takahashi.M et al., "Theoretical Analysis of IGZO Transparent Amorphous Oxide Semiconductor,", IDW '08 : Proceedings of the 15th International Display Workshops, Dec. 3, 2008, pp. 1637-1640.

Hayashi.R et al., "42.1: Invited Paper: Improved Amorphous In-Ga-Zn-O TFTS,", SID Digest '08 : SID International Symposium Digest of Technical Papers, May 20, 2008, vol. 39, pp. 621-624.

Prins.M et al., "A Ferroelectric Transparent Thin-Film Transistor,", Appl. Phys. Lett. (Applied Physics Letters) , Jun. 17, 1996, vol. 1996, vol. 68, No. 25, pp. 3650-3652.

Nakamura.M et al., "The phase relations in the In2O3-Ga2ZnO4-ZnO system at 1350° C,", Journal of Solid State Chemistry , Aug. 1, 1991, vol. 93, No. 2, pp. 298-315.

Kimizuka.N et al., "Syntheses and Single-Crystal Data of Homologous Compounds, In2O3(ZnO)m (m = 3, 4, and 5), InGaO3(ZnO)3, and Ga2O3(ZnO)m (m = 7, 8, 9, and 16) in the In2O3-ZnGa2O4-ZnO System,", Journal of Solid State Chemistry , Apr. 1, 1995, vol. 116, No. 1, pp. 170-178.

Nomura.K et al., "Thin-Film Transistor Fabricated in Single-Crystalline Transparent Oxide Semiconductor,", Science, May 23, 2003, vol. 300, No. 5623, pp. 1269-1272.

Masuda.S et al., "Transparent thin film transistors using ZnO as an active channel layer and their electrical properties,", J. Appl. Phys. (Journal of Applied Physics) , Feb. 1, 2003, vol. 93, No. 3, pp. 1624-1630.

Asakuma.N et al., "Crystallization and Reduction of Sol-Gel-Derived Zinc Oxide Films by Irradiation With Ultraviolet Lamp,", Journal of Sol-Gel Science and Technology, 2003, vol. 26, pp. 181-184.

Osada.T et al., "15.2: Development of Driver-Integrated Panel using Amorphous In-Ga-Zn-Oxide TFT,", SID Digest '09 : SID International Symposium Digest of Technical Papers, May 31, 2009, pp. 184-187.

Nomura.K et al., "Carrier transport in transparent oxide semiconductor with intrinsic structural randomness probed using single-crystalline InGaO3(ZnO)5 films,", Appl. Phys. Lett. (Applied Physics Letters) , Sep. 13, 2004, vol. 85, No. 11, pp. 1993-1995

Li.C et al., "Modulated Structures of Homologous Compounds InMO3(ZnO)m (M=In,Ga; m=Integer) Described by Four-Dimensional Superspace Group,", Journal of Solid State Chemistry , 1998, vol. 139, pp. 347-355.

Son.K et al., "42.4L: Late-News Paper: 4 Inch QVGA AMOLED Driven By the Threshold Voltage Controlled Amorphous GIZO (Ga2O3-In2O3-ZnO) TFT,", SID Digest '08 : SID International Symposium Digest of Technical Papers, May 20, 2008, vol. 39, pp. 633-636.

Lee.J et al., "World's Largest (15-Inch) XGA AMLCD Panel Using IGZO Oxide TFT,", SID Digest '08 : SID International Symposium Digest of Technical Papers, May 20, 2008, vol. 39, pp. 625-628.

Nowatari.H et al., "60.2: Intermediate Connector With Suppressed Voltage Loss for White Tandem OLEDS,", SID Digest '09 : SID International Symposium Digest of Technical Papers, May 31, 2009, vol. 40, pp. 899-902.

Kanno.H et al., "White Stacked Electrophosphorecent Organic Light-Emitting Devices Employing MOO3 As a Charge-Generation Layer,", Adv. Mater. (Advanced Materials), 2006, vol. 18, No. 3, pp. 339-342.

Tsuda.K et al., "Ultra Low Power Consumption Technologies for Mobile TFT-LCDs ,", IDW '02 : Proceedings of the 9th International Display Workshops, Dec. 4, 2002, pp. 295-298.

Van de Walle.C, "Hydrogen as a Cause of Doping in Zinc Oxide,", Phys. Rev, Lett. (Physical Review Letters), Jul. 31, 2000, vol. 85, No. 5, pp. 1012-1015.

Fung.T et al., "2-D Numerical Simulation of High Preformance Amorphous In-Ga-Zn-O TFTs for Flat Panel Displays,", AM-FPD '08 Digest of Technical Papers, Jul. 2, 2008, pp. 251-252, The Japan Society of Applied Physics.

Jeong.J et al., "3.1: Distinguished Paper: 12.1-Inch WXGA AMOLED Display Driven by Indium-Gallium-Zinc Oxide TFTs Array,", SID Digest '08 : SID International Symposium Digest of Technical Papers, May 20, 2008, vol. 39, No. 1, pp. 1-4.

Park.J et al., "High performance amorphous oxide thin film transistors with self-aligned top-gate structure,", IEDM 09: Technical Digest of International Electron Devices Meeting, Dec. 7, 2009, pp. 191-194.

Kurokawa.Y et al., "UHF RFCPUS on Flexible and Glass Substrates for Secure RFID Systems,", Journal of Solid-State Circuits , 2008, vol. 43, No. 1, pp. 292-299.

Ohara.H et al., "Amorphous In-Ga-Zn-Oxide TFTs with Suppressed Variation for 4.0 inch QVGA AMOLED Display,", AM-FPD '09 Digest of Technical Papers, Jul. 1, 2009, pp. 227-230, The Japan Society of Applied Physics.

Coates.D et al., "Optical Studies of the Amorphous Liquid-Cholesteric Liquid Crystal Transition:The "Blue Phase",", Physics Letters, Sep. 10, 1973, vol. 45A, No. 2, pp. 115-116.

Cho.D et al., "21.2:AL and SN-Doped Zinc Indium Oxide Thin Film Transistors for AMOLED Back-Plane,", SID Digest '09 : SID International Symposium Digest of Technical Papers, May 31, 2009, pp. 280-283.

Lee.M et al., "15.4:Excellent Performance of Indium-Oxide-Based Thin-Film Transistors by DC Sputtering,", SID Digest '09 : SID International Symposium Digest of Technical Papers, May 31, 2009, pp. 191-193.

Jin.D et al., "65.2:Distinguished Paper:World-Largest (6.5") Flexible Full Color Top Emission AMOLED Display on Plastic Film and Its Bending Properties, SID DIGEST '09 : SID International Digest of Technical Papers, May 31, 2009, pp. 983-985.

Sakata.J et al., "Development of 4.0-In. AMOLED Display With Driver Circuit Using Amorphous In-Ga-Zn-Oxide TFTs,", IDW '09 : Proceedings of the 16th International Display Workshops, 2009, pp. 689-692.

Park.J et al., "Amorphous Indium-Gallium-Zinc Oxide TFTS and Their Application for Large Size AMOLED,",AM-FPD '08 Digest of Technical Papers, Jul. 2, 2008, pp. 275-278.

Parks et al., "Challenge to Future Displays: Transparent AM-OLED Driven by Peald Grown ZNO TFT,", IMID '07 Digest, 2007, pp. 1249-1252.

Godo.H et al., "Temperature Dependence of Characteristics and Electronic Structure for Amorphous In-Ga-Zn-Oxide TFT,", AM-FPD '09 Digest of Technical Papers, Jul. 1, 2009, pp. 41-44.

Osada.T et al., "Development of Driver-Integrated Panel Using Amorphous In-Ga-Zn-Oxide TFT,", AM-FPD '09 Digest of Technical Papers, Jul. 1, 2009, pp. 33-36.

Hirao.T et al., "Novel Top-Gate Zinc Oxide Thin-Film Transistors (ZNO TFTS) for AMLCDS,", Journal of the SID, 2007, vol. 15, No. 1, pp. 17-22.

Hosono.H, "68.3:Invited Paper:Transparent Amorphous Oxide Semiconductors for High Performance TFT,", SID Digest '07 : SID International Symposium Digest of Technical Papers, 2007, vol. 38, pp. 1830-1833.

Godo.H et al., "P-9:Numerical Analysis on Temperature Dependence of Characteristics of Amorphous In-Ga-Zn-Oxide TFT,", SID Digest '09 : SID International Symposium Digest of Technical Papers, May 31, 2009, pp. 1110-1112.

Ohara.H et al., "21.3:4.0 In. QVGA AMOLED Display Using In-Ga-Zn-Oxide TFTS With a Novel Passivation Layer,", SID Digest '09 : SID International Symposium Digest of Technical Papers, May 31, 2009, pp. 284-287.

Miyasaka.M, "Suftla Flexible Microelectronics on Their Way to Business,", SID Digest '07 : SID International Symposium Digest of Technical Papers, 2007, vol. 38, pp. 1673-1676.

(56) References Cited

OTHER PUBLICATIONS

Chern.H et al., "An Analytical Model for the Above-Threshold Characteristics of Polysilicon Thin-Film Transistors,", IEEE Transactions on Electron Devices, Jul. 1, 1995, vol. 42, No. 7, pp. 1240-1246.
Kikuchi.H et al., "39.1:Invited Paper:Optically Isotropic Nano-Structured Liquid Crystal Composites for Display Applications,", SID Digest '09 : SID International Symposium Digest of Technical Papers, May 31, 2009, pp. 578-581.
Asaoka.Y et al., "29.1: Polarizer-Free Reflective LCD Combined With Ultra Low-Power Driving Technology,", SID Digest '09 :SID International Symposium Digest of Technical Papers, May 31, 2009, pp. 395-398.
Lee.H et al., "Current Status of , Challenges to, and Perspective View of AM-OLED ,", IDW '06 : Proceedings of the 13th International Display Workshops, Dec. 7, 2006, pp. 663-666.
Kikuchi.H et al., "62.2:Invited Paper:Fast Electro-Optical Switching In Polymer-Stabilized Liquid Crystalline Blue Phases for Display Application,", SID Digest '07 : SID International Symposium Digest of Technical Papers, 2007, vol. 38, pp. 1737-1740.
Nakamura.M, "Synthesis of Homologous Compound with New Long-Period Structure,", Nirim Newsletter, Mar. 1, 1995, vol. 150, pp. 1-4.
Kikuchi.H et al., "Polymer-Stabilized Liquid Crystal Blue Phases,", Nature Materials, Sep. 2, 2002, vol. 1, pp. 64-68.
Kimizuka.N et al., "SPINEL,YBFE2O4, and YB2FE3O7 Types of Structures for Compounds in the IN2O3 and SC2O3-A2O3-BO Systems [A; Fe, Ga, Or Al: B: Mg, Mn, Fe, Ni, Cu,Or Zn] at Temperatures Over $1000°$ C,", Journal of Solid State Chemistry, 1985, vol. 60, pp. 382-384.
Kitzerow.H et al., "Observation of Blue Phases in Chiral Networks,", Liquid Crystals, 1993, vol. 14, No. 3, pp. 911-916.
Costello.M et al., "Electron Microscopy of a Cholesteric Liquid Crystal and Its Blue Phase,", Phys. Rev. A (Physical Review. A), May 1, 1984, vol. 29, No. 5, pp. 2957-2959.
Meiboom.S et al., "Theory of the Blue Phase of Cholesteric Liquid Crystals,", Phys. Rev. Lett. (Physical Review Letters), May 4, 1981, vol. 46, No. 18, pp. 1216-1219.
Park.Sang-Hee et al., "42.3: Transparent ZnO Thin Film Transistor for the Application of High Aperture Ratio Bottom Emission AM-OLED Display,", SID Digest '08 : SID International Symposium Digest of Technical Papers, May 20, 2008, vol. 39, pp. 629-632.
Orita.M et al., "Mechanism of Electrical Conductivity of Transparent InGaZnO4,", Phys. Rev. B (Physical Review. B), Jan. 15, 2000, vol. 61, No. 3, pp. 1811-1816.
Nomura.K et al., "Amorphous Oxide Semiconductors for High-Performance Flexible Thin-Film Transistors,", Jpn. J. Appl. Phys. (Japanese Journal of Applied Physics) , 2006, vol. 45, No. 5B, pp. 4303-4308.
Janotti.A et al., "Native Point Defects in ZnO,", Phys. Rev. B (Physical Review. B), Oct. 4, 2007, vol. 76, No. 16, pp. 165202-1-165202-22.
Park.J et al., "Electronic Transport Properties of Amorphous Indium-Gallium-Zinc Oxide Semiconductor Upon Exposure to Water,", Appl. Phys. Lett. (Applied Physics Letters) , 2008, vol. 92, pp. 072104-1-072104-3.
Hsieh.H et al., "P-29:Modeling of Amorphous Oxide Semiconductor Thin Film Transistors and Subgap Density of States,", SID Digest '08 SID International Symposium Digest of Technical Papers, 2008, vol. 39, pp. 1277-1280.
Janotti.A et al., "Oxygen Vacancies In ZnO,", Appl. Phys. Lett. (Applied Physics Letters) , 2005, vol. 87, pp. 122102-1-122102-3.
Oba.F et al., "Defect energetics in ZnO: A hybrid Hartree-Fock density functional study,", Phys. Rev. B (Physical Review. B), 2008, vol. 77, pp. 245202-1-245202-6.
Orita.M et al., "Amorphous transparent conductive oxide InGaO3(ZnO)m (m<4):a Zn4s conductor,", Philosophical Magazine, 2001, vol. 81, No. 5, pp. 501-515.

Hosono.H et al., "Working hypothesis to explore novel wide band gap electrically conducting amorphous oxides and examples,", J. Non-Cryst. Solids (Journal of Non-Crystalline Solids), 1996, vol. 198-200, pp. 165-169.
Mo.Y et al., "Amorphous Oxide TFT Backplanes for Large Size AMOLED Displays,", IDW '08 : Proceedings of the 6th International Display Workshops, Dec. 3, 2008, pp. 581-584.
Kim.S et al., "High-Performance oxide thin film transistors passivated by various gas plasmas,", 214th ECS Meeting, 2008, No. 2317, ECS.
Clark.S et al., "First Principles Methods Using Castep,", Zeitschrift fur Kristallographie, 2005, vol. 220, pp. 567-570.
Lany.S et al., "Dopability, Intrinsic Conductivity, and Nonstoichiometry of Transparent Conducting Oxides,", Phys. Rev. Lett. (Physical Review Letters), Jan. 26, 2007 , vol. 98, pp. 045501-1-045501-4.
Park.J et al., "Dry etching of ZnO films and plasma-induced damage to optical properties,", J. Vac. Sci. Technol. B (Journal of Vacuum Science & Technology B), Mar. 1, 2003, vol. 21, No. 2, pp. 800-803.
Oh.M et al., "Improving the Gate Stability of ZNO Thin-Film Transistors With Aluminum Oxide Dielectric Layers,", J.Electrochem. Soc. (Journal of the Electrochemical Society), 2008, vol. 155, No. 12, pp. H1009-H1014.
Ueno.K et al., "Field-Effect Transistor on SrTiO3 With Sputtered Al2O3 Gate Insulator,", Appl. Phys. Lett. (Applied Physics Letters) , Sep. 1, 2003, vol. 83, No. 9, pp. 1755-1757.
H. Sussek et al., "Precursor chemistry of Group III nitrides Part XVI. Synthesis and structure of monomeric penta-coordinated intramolecularly adduct-stabilized amidobisazides of aluminum, gallium and indium with an all-nitrogen coordination sphere: OMCVD of GaN using $(N_3)_2 Ga\{N[CH_2 CH_2 (NEt_2)]_2\}$", Journal of Organometallic Chemistry, 2000, vol. 602, pp. 29-36.
J. Khanderi et al., "Ligand stabilised dialkyl aluminium amides as new precursors for aluminium nitride thin films", Journal of Materials Chemistry, Sep. 22, 2004, vol. 14, pp. 3210-3214.
K.P. Beaumont et al., "Platinum Complexes of Substituted Ethylenediamines and their Anti-Tumor Activity", Chemico-Biological Interactions, 1976, vol. 14, pp. 179-193.
H. Schumann et al. "Homoleptic Organometallic Compounds of Zinc, Cadmium, and Mercury, Intramolecularly Stabilized by Amine Ligands", European Journal of Inorganic Chemistry, 1998, pp. 245-252.
Extended European Search Report issued in European Application No. 11 83 8078 mailed Apr. 15, 2014.
M. Bassindale et al., "Application of polydentate chiral amines within magnesium-mediated asymmetric deprotonation reactions", Tetrahedron Letters. 45 (2004), pp. 4175-4179.
T. Cloitre et al., "ZnCdSe-ZnSe heterostructures grown by MOVPE"; Materials Science and Engineering. B43 (1997), pp. 16-20.
P. Hitchcock et al., "Anomalous reactions of the diamine $Me_2NCH_2NMe_2$ with nickel(II) and cobalt(II)", J. Chem. Soc., Dalton Trans., 2002, pp. 4720-4725.
O.T. Beachely Jr. et al., "Indium(II) Compounds Containing the Neopentyl Substituent, $In(CH_2CMe_3)_3$. $In(CH_2CMe_3)_2CI$, $In(CH_2CMe_3)CI_2$, and $In(CH_2CMe_1)_2CH_3$. Crystal and Molecular Structure of Dichloroneopentylindium(III), an Inorganic Polymer"; Organometallies, 1989, 8, pp. 1915-1921.
J. Weston, "Theoretical Study on the Structure and Electronic Properties of Mono-and Bimetallic Methylzinc Complexes Containing Bidenstate Ligands", Organometallics, 2001, 20, pp. 713-720.
D.C. Bradley et al., "Ethylenediamine complexes of magnesium: the search for volatile compounds"; Eur. J. Solid State Inorg. Chem., TOME 30, 1993, p. 241-258.
T. Maruyama, "Cobalt Thin Films Prepared by Chemical Vapor Deposition from Cobalt Acetylacetonates"; Jpn. J. Appl. Phys., Part 2, vol. 36, No. 6A, (Jun. 1, 1997), pp. 1 705-707
D. Barreca et al., "Composition and Microstructure of Cobalt Oxide Thin Films Obtained from a Novel Cobalt (II) Precursor by Chemical Vapor Deposition"; Chemistry of Materials, vol. 13, (2001), p. 588-593.
D.-X. Ye et al., "Low temperature chemical vapor deposition of Co thin films from $Co_2(CO)_8$"; Thin Solid Films, vol. 485, (Aug. 1, 2005), p. 95-100.

(56) References Cited

OTHER PUBLICATIONS

K. Kim et al., "Comparison of Co Films Deposited by Remote Plasma Atomic Layer Deposition Method with Cyclopentadienylcobalt Dicarbonyl [CpCo(CO)$_2$] and Dicobalt Octacarbonyl [Co$_2$(CO)$_8$]"; Jpn. J. Appl. Phys., Part 2, vol. 46, No. 8, (2007), pp.1.173-1.176.

Han-Bo-Ram Lee et al., "High Quality Area-Selective Atomic Layer Deposition Co Using Ammonia Gas as a Reactant"; Journal of The Electrochemical Society, vol. 157, No. 1, (2010), pp. D10-D15.

Z. Li et al., "Synthesis and characterization of volatile liquid cobalt amidinates"; Dalton Transactions, No. 19, (May 21, 2008), pp. 2592-2597.

Y. Au et al., "Selective Chemical Vapor Deposition of Manganese Self-Aligned Capping Layer for Cu Interconnections in Microelectronics"; Journal of The Electrochemical Society, vol. 157, No. 6, (2010), pp. D341-D345.

Y. Au et al., "Filling Narrow Trenches by Iodine-Catalyzed CVD of Copper and Manganese on Manganese Nitride Barrier/Adhesion Layers"; Journal of The Electrochemical Society, vol. 158, No. 5, (2011), pp. D248-D253.

A.B.M. Almamun Ashrafi et al., "High-Quality ZnO Layers Grown on 6H-SiC Substrates by Metalorganic Chemical Vapor Deposition"; Jpn. J. Appl. Phys., Part 1, vol. 43, No. 3, (Mar. 2004), pp. 1114-1117.

International Preliminary Report on Patentability mailed May 23, 2013 including English-language Translation of Written Opinion issued in the International Application No. PCT/JP2011/075347

(AMIDE AMINO ALKANE) METAL COMPOUND, METHOD OF MANUFACTURING METAL-CONTAINING THIN FILM USING SAID METAL COMPOUND

TECHNICAL FIELD

The present invention relates to a novel (amide amino alkane) metal compound, and a method of producing a metal-containing thin film on an object by a chemical vapor deposition method (hereinafter, referred to as CVD method) using the metal compound.

BACKGROUND ART

In recent years, various metal-containing thin films have been researched and developed as materials in the field of semiconductors, electronic components, and the like.

Conventionally, various magnesium compounds such as bis(cyclopentadienyl)magnesium, magnesium alkoxide and magnesium diketonato, for example, have been known as magnesium compounds to be used for the formation of magnesium-containing thin film (See Patent Documents 1 to 2). Among them, bis(cyclopentadienyl)magnesium, and analogs thereof are relatively frequently employed. Meanwhile, bis(amide amino alkane) magnesium compounds have been known and used as a catalyst, and a material for the production of medicines, agricultural chemicals, and the like, for example (See Non-Patent Documents 1 to 2).

There have been proposed, as cobalt compounds to be used for the formation of thin film, bis(acetylacetonato)cobalt (See, for example, Non-Patent Document 3), bis(dipivaloylmethanato)cobalt (See, for example, Non-Patent Document 4), octacarbonyl dicobalt (See, for example, Non-Patent Document 5 and Patent Document 3), cobalt cyclopentadienyl dicarbonyl (See, for example, Non-Patent Document 6 and Patent Document 4) and bis(trimethylsilyl cyclopentadienyl)cobalt (See, for example, Patent Document 5), bis(N,N'-diisopropylacetoamidinato)cobalt (See, for example, Patent Document 6, Patent Document 7 and Non-Patent Document 7) and bis(N-t-butyl-N'-ethylpropionamidinato)cobalt (See, for example, Patent Document 8 and Non-Patent Document 8), for example.

There have been proposed, as manganese compounds to be used for the formation of thin film, bis(dipivaloylmethanato)manganese (See, for example, Patent Document 9), bis(ethylcyclopentadienyl)manganese (See, for example, Patent Documents 9 and 10), bis(N,N'-diisopropylacetoamidinato)manganese (See, for example, Patent Document 11) and bis(N,N'-diisopropylpentaneamidinato)manganese (See, for example, Patent Documents 12 and 13 and Non-Patent Documents 9 and 10), for example.

There have been proposed, as zinc compounds to be used for the formation of thin film, bis(acetylacetonato)zinc (See, for example, Patent Documents 14 and 15), for example.

There have been proposed, as metal compounds to be used for the formation of iron-containing thin film, nickel-containing thin film or lanthanum-containing thin film, bis(N,N'-diisopropylacetoamidinato)iron, bis(N,N'-diisopropylacetoamidinato)nickel and tris(N,N'-diisopropyl-2-t-butylamidinato)lanthanum (See, for example, Patent Document 11), for example.

CITATION LIST

Patent Document

Patent Document 1: JP-A-2002-170993
Patent Document 2: JP-A-2005-298874
Patent Document 3: US 2005/0130417 A1
Patent Document 4: US 2006/0157863 A1
Patent Document 5: WO 2008/111499 A1
Patent Document 6: WO 2004/046417 A1
Patent Document 7: WO 2009/088522 A1
Patent Document 8: JP-A-2010-524264
Patent Document 9: WO 2010/116889 A1
Patent Document 10: WO 2011/037090 A1
Patent Document 11: JP-A-2010-156058
Patent Document 12: WO 2009/117670 A1
Patent Document 13: WO 2011/050073 A1
Patent Document 14: JP-A-2009-277357
Patent Document 15: JP-A-2003-31846

Non-Patent Document

Non-patent Document 1: Eur. J. Solid State Inorg. Chem., p. 241 (1993)
Non-patent Document 2: Tetrahedron Lett., p. 4175 (2004)
Non-patent Document 3: Japanese Journal of Applied Physics, vol. 36, p. 705 (1997)
Non-patent Document 4: Chemistry of Materials, vol. 13, p. 588 (2001)
Non-patent Document 5: Thin Solid Films, vol. 485, p. 95 (2005)
Non-patent Document 6: Japanese Journal of Applied Physics, vol. 46, p. 173 (1997)
Non-patent Document 7: Journal of The Electrochemical Society, vol. 157, D10-D15 (2010)
Non-patent Document 8: Dalton Transactions, p. 2592-2597 (2008)
Non-patent Document 9: Journal of The Electrochemical Society, vol. 157, D341-D345 (2010)
Non-patent Document 10: Journal of The Electrochemical Society, vol. 158, D248-D253 (2011)
Non-patent Document 11: Jpn. J. Appl. Phys. 1114 (2004)

SUMMARY OF THE INVENTION

Problems to be Solved by the Invention

However, the conventional metal compounds to be used for the formation of thin film do not necessarily have optimal properties such as steam pressure, heat stability and reactivity for the formation of metal-containing thin film, and it may be that no metal compounds are adequate for the formation of metal-containing thin film. Accordingly, there is a need for metal compounds having all properties such as steam pressure, heat stability and reactivity satisfying the requirements.

An object of the present invention is to solve the above-mentioned problems, and to provide a metal compound which is suitable for industrial use and from which a metal-containing thin film may be produced on an object by a simple method, and more specifically, a metal compound which is suitable for the formation of metal-containing thin film by a CVD method. Another object of the present invention is to provide a method of producing a metal-containing thin film using the metal compound.

Means for Solving the Problems

The present invention relates to the following items:
[1] An (amide amino alkane) metal compound represented by the formula (1):

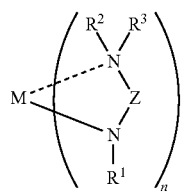

(1)

wherein

M represents a metal atom;

$R^1$ represents a linear, branched or cyclic alkyl group having 1 to 6 carbon atoms;

$R^2$ and $R^3$ may be the same as, or different from each other, and each independently represents a linear or branched alkyl group having 1 to 3 carbon atoms, or $R^2$ and $R^3$ may form a substituted or unsubstituted 5- or 6-membered ring together with the nitrogen atom to which they are bound;

Z represents a linear or branched alkylene group having 1 to 10 carbon atoms (a part of which may optionally form a ring); and n represents a number of the ligands, which is equal to the valence of the metal (M), and represents an integer of from 1 to 3;

with the proviso that the metal compounds in which M is Li (Lithium), Be (Beryllium), Ge (Germanium) or Nd (Neodymium) are excluded;

the metal compounds in which M is Mg (Magnesium) and $R^1$ is methyl group are excluded;

the metal compounds in which M is Zn (Zinc) and $R^1$ is methyl group are excluded;

the metal compounds in which M is Bi (Bismuth) and $R^1$ is t-butyl group are excluded; and in cases where n is two or greater, two or more ligands may be the same as, or different from each other.

[2] The (amide amino alkane) metal compound as described in [1], wherein M is sodium, magnesium, manganese, iron, cobalt, nickel, zinc, yttrium, lanthanum, or indium.

[3] The (amide amino alkane) metal compound as described in [1], wherein Z is a linear or branched alkylene group having 1 to 5 carbon atoms, or a group represented by the formula:

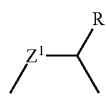

wherein $Z^1$ represents a linear alkylene group having 1 to 3 carbon atoms; and R represents a linear or branched alkyl group having 1 to 6 carbon atoms, or a cycloalkyl group having 3 to 6 carbon atoms.

[4] A method of producing an (amide amino alkane) metal compound as described in [1], which is represented by the formula (1):

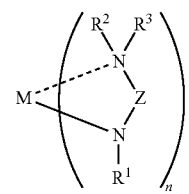

(1)

wherein M, $R^1$, $R^2$, $R^3$, Z and n are defined as above;

comprising a step of:

reacting a mono- or di-alkyl metal compound represented by the formula (2a) or (2b):

$R^4M$ (2a)

$R^4R^5M$ (2b)

wherein

M represents a metal atom; and $R^4$ and $R^5$ may be the same as, or different from each other, and each independently represents a linear or branched alkyl group having 1 to 10 carbon atoms:

with a di-amino alkane compound represented by the formula (3):

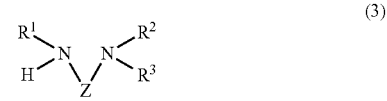

(3)

wherein $R^1$, $R^2$, $R^3$ and Z are defined as above.

[5] A method of producing an (amide amino alkane) metal compound as described in [1], which is represented by the formula (1):

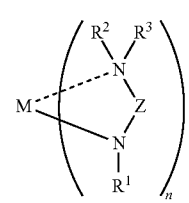

(1)

wherein M, $R^1$—, $R^2$, $R^3$, Z and n are defined as above;

comprising steps of reacting an alkyl alkali metal compound represented by the formula (4a);

$R^4A$ (4a)

wherein $R^4$ represents a linear or branched alkyl group having 1 to 10 carbon atoms; and A represents an alkali metal atom;

or an alkali metal with a di-amino alkane compound represented by the formula (3):

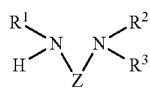
(3)

wherein R¹, R², R³ and Z are defined as above;
to form a (amide amino alkane) alkali metal compound represented by the formula (5):

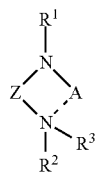
(5)

wherein R¹, R², R³, A and Z are defined as above; and
reacting the (amide amino alkane) alkali metal compound with a metal halide compound represented by the formula (6):

MX$_n$ (6)

wherein
M represents a metal atom;
X represents a halogen atom; and
n represents a number of the halogen atoms, which is equal to the valence of the metal (M), and represents an integer of from 1 to 3.

[6] A method of producing an (amide amino alkane) metal compound as described in [1], which is represented by the formula (1):

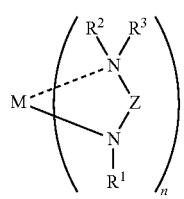
(1)

wherein R¹, R², R³, M, Z and n are defined as above;
comprising a step of:
reacting a metal represented by the formula (7):

M (7)

wherein
M represents a metal atom, and is defined as above;
with a di-amino alkane compound represented by the formula (3):

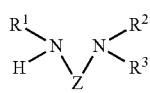
(3)

wherein R¹, R², R³ and Z are defined as above.

[7] A method of producing a metal-containing thin film by a chemical vapor deposition method, wherein an (amide amino alkane) metal compound as described in [1] is used as a source.

[8] A material for forming a metal-containing thin film, comprising an (amide amino alkane) metal compound as described in [1].

Effect of the Invention

According to the present invention, there may be provided a novel (amide amino alkane) metal compound, including bis(amide amino alkane) magnesium compound, bis(amide amino alkane) cobalt compound, bis(amide amino alkane) manganese compound and bis(amide amino alkane) zinc compound, which is particularly suitable for the production/formation of metal-containing thin film by a CVD method. In addition, a metal-containing thin film may be produced with good film-forming performance by a CVD method using the metal compound.

The (amide amino alkane) metal compound, including bis(amide amino alkane) magnesium compound, bis(amide amino alkane) cobalt compound, bis(amide amino alkane) manganese compound and bis(amide amino alkane) zinc compound, is useful as a material for the formation of metal-containing thin film, including magnesium-containing thin film, cobalt-containing thin film, manganese-containing thin film and zinc-containing thin film, respectively, and is useful as a catalyst, and a material for the production of medicines, agricultural chemicals, and the like, for example.

DESCRIPTION OF EMBODIMENTS

Figure 1:
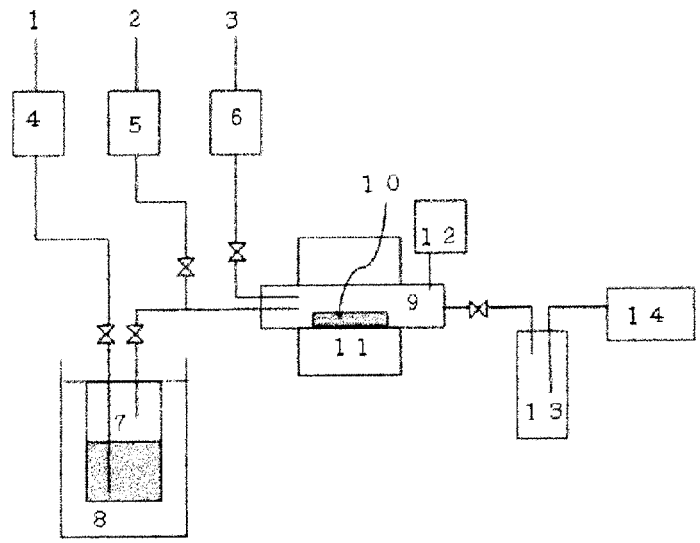
FIG. 1 is a diagram illustrating the construction of the vapor deposition apparatus, which was used in "Examples" for the formation of magnesium-containing thin film using the bis(amide amino alkane) magnesium compound of the present invention.

The (amide amino alkane) metal compound of the present invention is represented by the above formula (1).

In the formula (1), M represents a metal atom (excluding Be (beryllium), Ge (germanium) and Nd (neodymium)), and may be, for example, lithium, sodium, magnesium, manganese, iron, cobalt, nickel, zinc, yttrium, lanthanum, or indium.

R¹ represents a linear, branched or cyclic alkyl group having 1 to 6 carbon atoms such as methyl, ethyl, n-propyl, isopropyl, cyclopropyl, s-butyl, t-butyl, cyclobutyl, t-pentyl, neopentyl, cyclopentyl and cyclohexyl. R¹ may be preferably a linear or branched alkyl group having 1 to 6 carbon atoms, more preferably a linear or branched alkyl group having 1 to 5 carbon atoms. In one embodiment, R¹ may be more preferably a linear or branched alkyl group having 2 to 5 carbon atoms, more preferably a linear or branched alkyl group having 3 to 5 carbon atoms, particularly preferably isopropyl, s-butyl, t-butyl or t-pentyl.

The cases where R¹ is methyl group when M is Mg (magnesium), however, are excluded. The cases where R¹ is methyl group when M is Zn (zinc) are excluded. The cases where R¹ is t-butyl group when M is Bi (bismuth) are excluded.

R² and R³ may be the same as, or different from each other, and each independently represents a linear or branched alkyl group having 1 to 3 carbon atoms such as methyl, ethyl, n-propyl and isopropyl, or $R^2$ and $R^3$ may form a substituted or unsubstituted 5- or 6-membered ring together with the nitrogen atom to which they are bound. $R^2$ and $R^3$ may be preferably an alkyl group having 1 to 2 carbon atoms (methyl, ethyl) and may also preferably form a substituted or unsubstituted 5-membered ring, more preferably a unsubstituted 5-membered ring, together with the nitrogen atom to which they are bound. $R^2$ and $R^3$ may be particularly preferably methyl or ethyl.

Z represents a linear or branched alkylene group having 1 to 10 carbon atoms (a part of which may optionally form a ring). Z may be preferably a linear or branched alkylene group having 1 to 10 carbon atoms which does not contain a cycloalkyl group, although a part of Z may form a ring, that is, Z may contain a cycloalkyl group such as cyclopropyl, cyclobutyl, cyclopentyl and cyclohexyl, Z may be preferably a linear or branched alkylene group having 1 to 5 carbon atoms such as methylene, ethylene, trimethylene, methylethylene, 1,2-dimethylethylene, 1,1-dimethylethylene, tetraethylene, 2-methyltrimethylene and hexamethylene.

In cases where Z is a linear alkylene group, Z may be more preferably an alkylene group having 1 to 3 carbon atoms, particularly preferably an alkylene group having 2 carbon atoms (ethylene).

In cases where Z is a branched alkylene group, Z may be preferably, for example, a group represented by the formula:

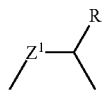

wherein $Z^1$ represents a linear alkylene group having 1 to 3 carbon atoms, and R represents a linear or branched alkyl group having 1 to 6 carbon atoms, or a cycloalkyl group having 3 to 6 carbon atoms.

$Z^1$ represents a linear alkylene group having 1 to 3 carbon atoms such as methylene, ethylene and trimethylene, for example, and may be preferably methylene.

R represents a linear or branched alkyl group having 1 to 6 carbon atoms such as methyl, ethyl, n-propyl, isopropyl, n-butyl, isobutyl, s-butyl, t-butyl, heptyl and hexyl, or a cycloalkyl group having 3 to 6 carbon atoms such as cyclopropyl, cyclobutyl, cyclopentyl and cyclohexyl, for example, and may be preferably a linear or branched alkyl group having 1 to 6 carbon atoms, more preferably a linear or branched alkyl group having 1 to 4 carbon atoms, more preferably a linear alkyl group having 1 to 3 carbon atoms, particularly preferably methyl.

In one preferred embodiment of this type, $Z^1$ may be methylene, and R may be a linear alkyl group having 1 to 3 carbon atoms, more preferably methyl.

Z may be preferably a linear or branched alkylene group having 1 to 10 carbon atoms which does not contain a ring (cycloalkyl group), more preferably a linear or branched alkylene group having 1 to 5 carbon atoms, and may be particularly preferably an alkylene group having 1 to 5 carbon atoms, more preferably having 1 to 3 carbon atoms, more preferably having 2 carbon atoms (linear alkylene group), or an alkylene group having 2 carbon atoms to which one or two alkyl groups having 1 to 3 carbon atoms, more preferably methyl, are bound (branched alkylene group). In the branched alkylene group, two alkyl groups may be bound to one carbon atom in the alkylene group, or may be bound to different carbon atoms, and two alkyl groups may be the same as, or different from each other.

In the formula (1), n represents a number of the ligands, which is equal to the valence of the metal (M), and n is generally an integer of from 1 to 3.

In cases where n is two or greater, two or more ligands may be the same as, or different from each other. In cases where the ligand is a mixture of two or more different types of ligands, a plurality of complexes may be formed.

In one preferred embodiment of the present invention, $R^1$ may be an alkyl group having 2 to 5 carbon atoms, more preferably an alkyl group having 3 to 5 carbon atoms, and $R^2$ and $R^3$ may be an alkyl group having 1 to 2 carbon atoms, and Z may be an alkylene group having 1 to 3 carbon atoms.

In another preferred embodiment of the present invention, $R^1$ may be an alkyl group having 1 to 5 carbon atoms, and $R^2$ and $R^3$ may be an alkyl group having 1 to 2 carbon atoms, and Z may be a group represented by the formula:

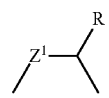

wherein $Z^1$ represents an alkylene group having 1 to 3 carbon atoms, and R represents a linear or branched alkyl group having 1 to 4 carbon atoms.

Specific examples of the (amide amino alkane) metal compound of the present invention include the compounds represented by the following formulas (1) to (498). In the formulas, M represents a metal atom, and n represents a number of the ligands, which is equal to the valence of the metal (M). In addition, o and p represent a number of each of ligands, and the sum (o+p) is equal to the valence of the metal (M).

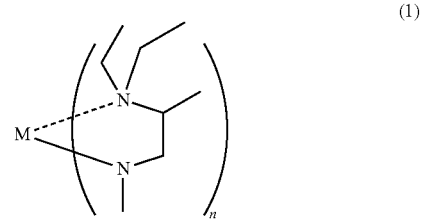

(1)

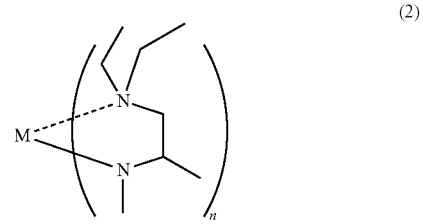

(2)

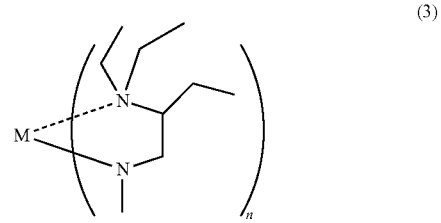

(3)

(4)
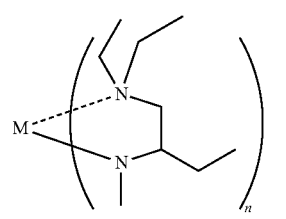
(5)
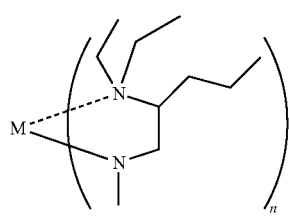
(6)
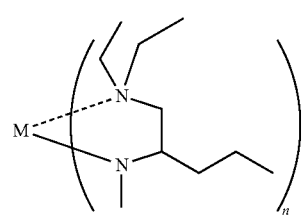
(7)
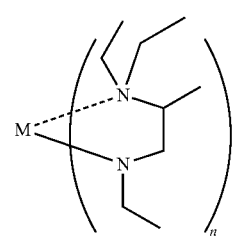
(8)
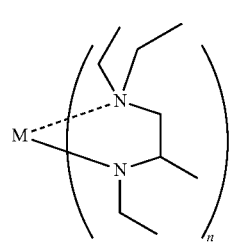
(9)
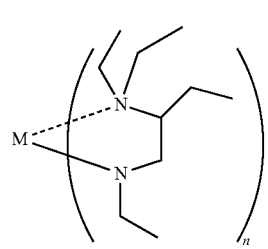
(10)
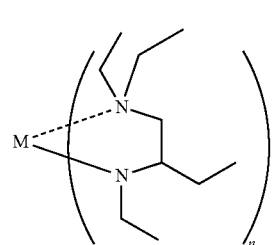
(11)
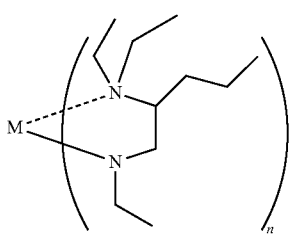
(12)
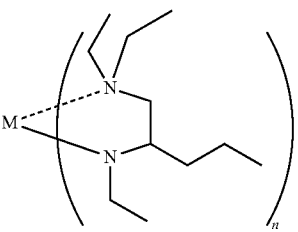
(13)
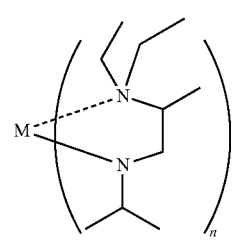
(14)
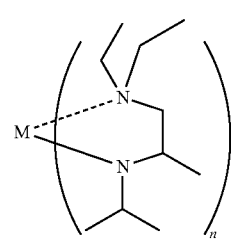
(15)
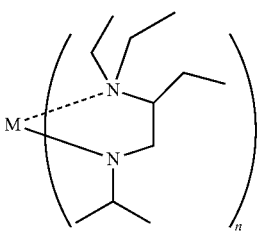
(16)
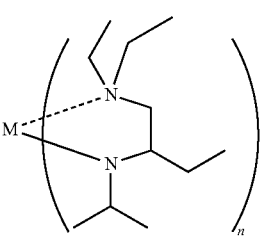

(17) 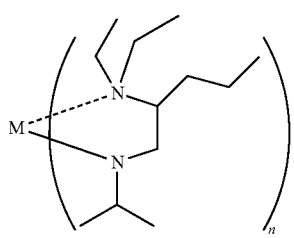
(18) 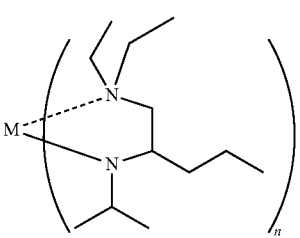
(19) 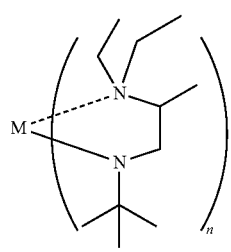
(20) 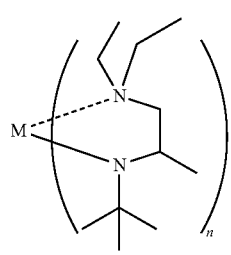
(21) 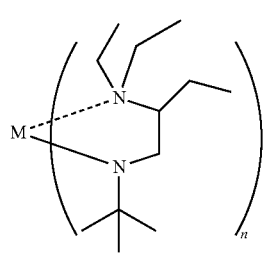
(22) 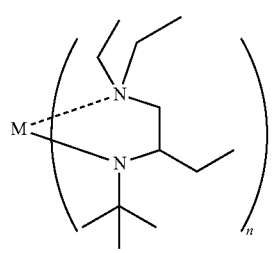
(23) 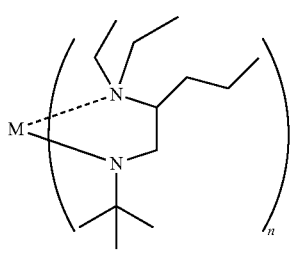
(24) 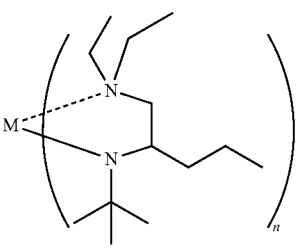
(25) 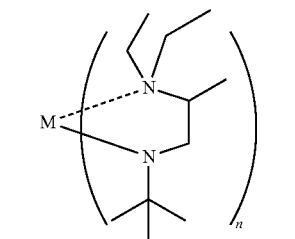
(26) 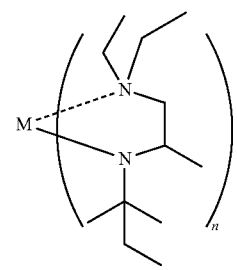
(27) 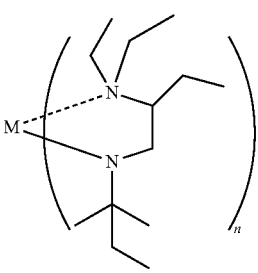
(28) 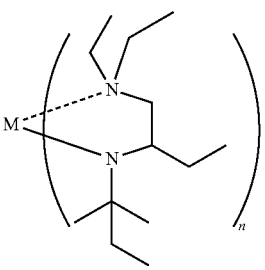

(29)
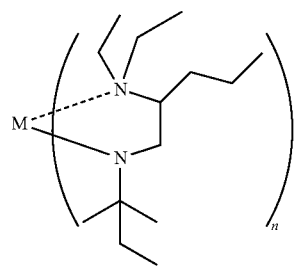
(30)
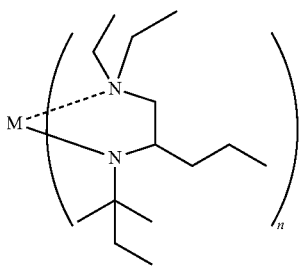
(31)
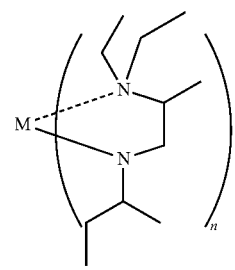
(32)
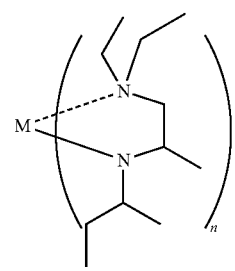
(33)
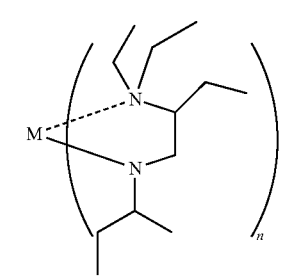
(34)
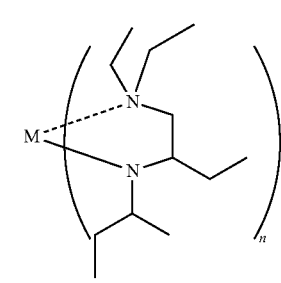
(35)
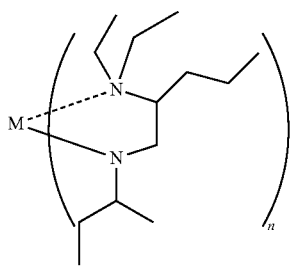
(36)
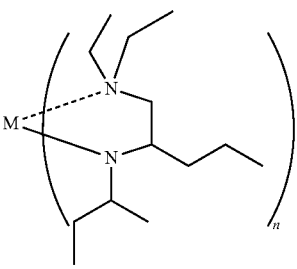
(37)
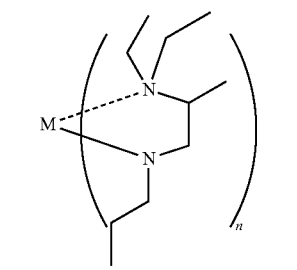
(38)
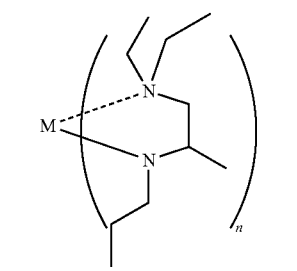
(39)
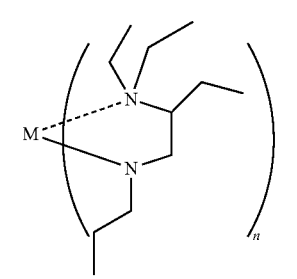
(40)
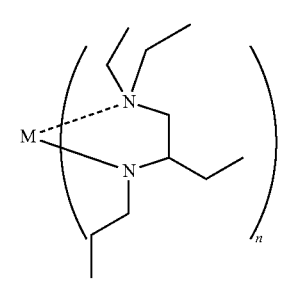

-continued
(41)
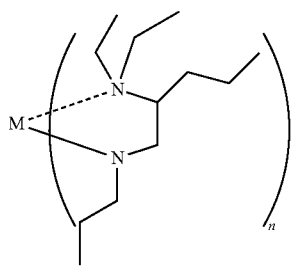
(42)
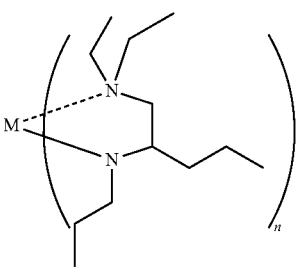
(43)
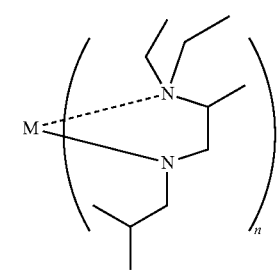
(44)
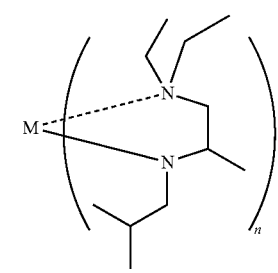
(45)
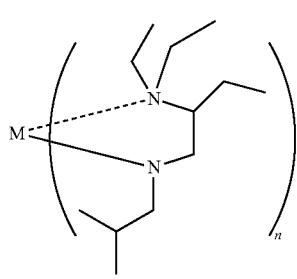
(46)
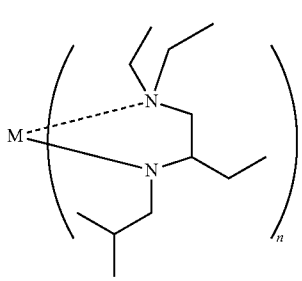
-continued
(47)
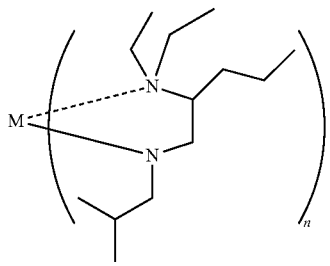
(48)
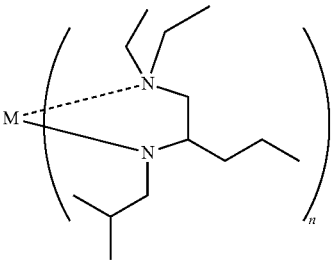
(49)
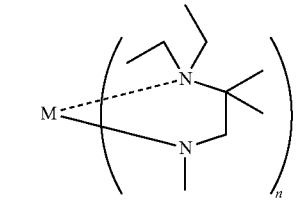
(50)
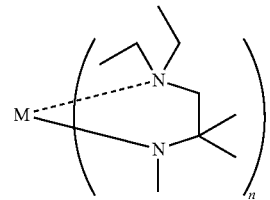
(51)
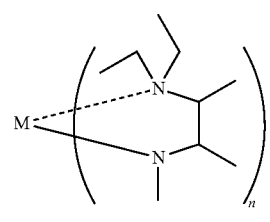
(52)
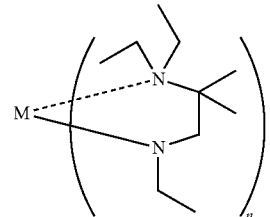
(53)
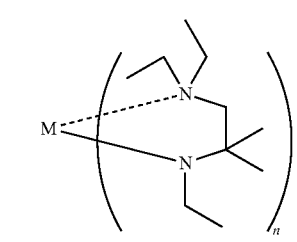

-continued
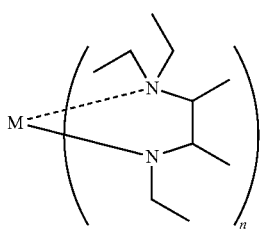
(54)
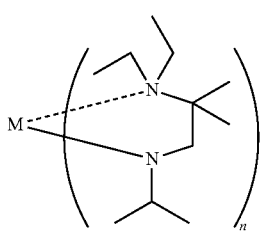
(55)
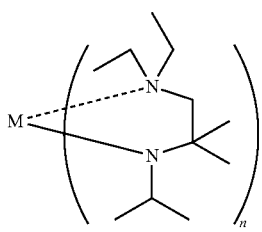
(56)
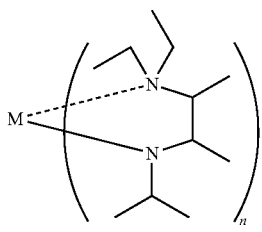
(57)
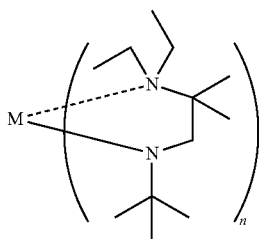
(58)
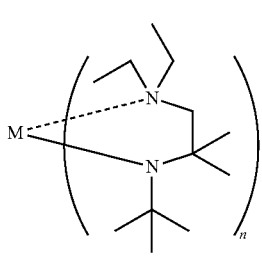
(59)
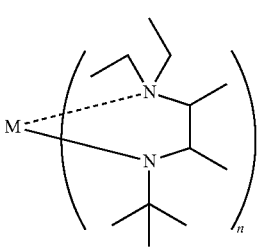
(60)
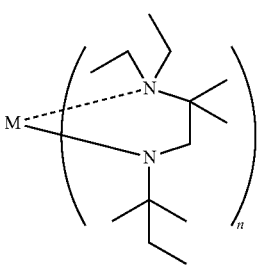
(61)
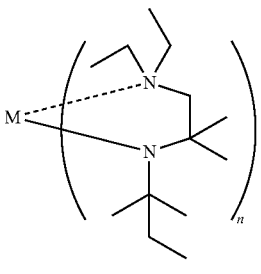
(62)
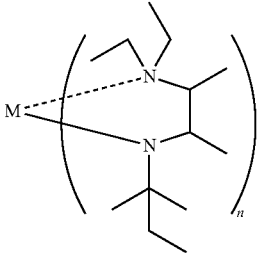
(63)
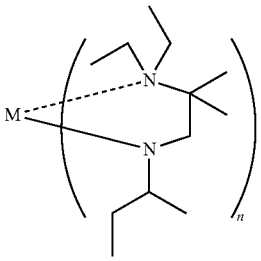
(64)
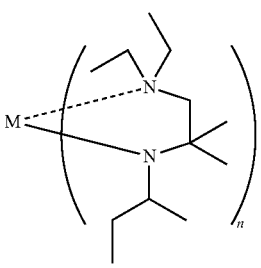
(65)

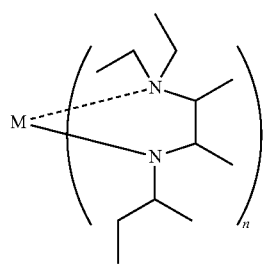
(66)
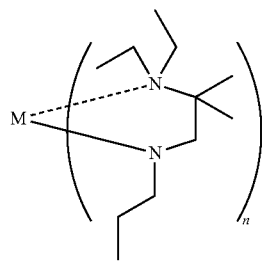
(67)
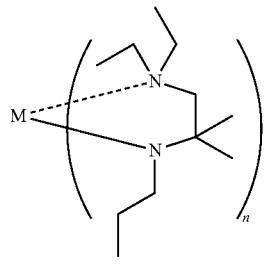
(68)
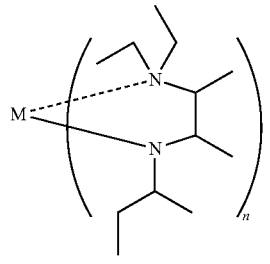
(69)
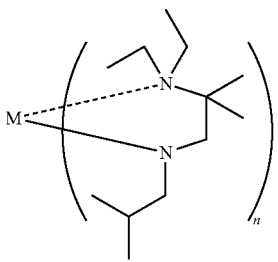
(70)
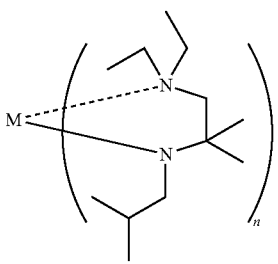
(71)
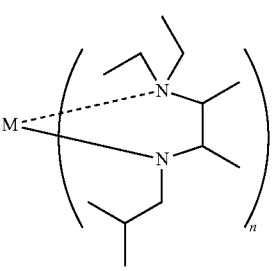
(72)
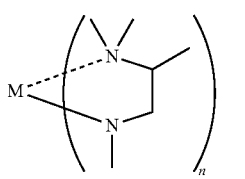
(73)
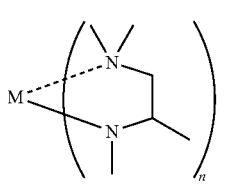
(74)
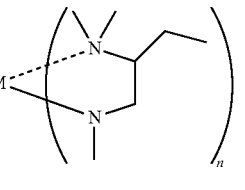
(75)
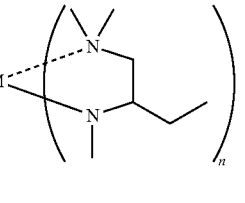
(76)
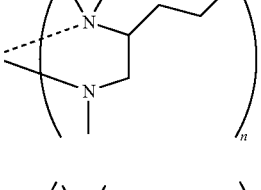
(77)
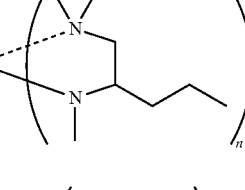
(78)
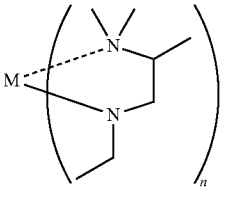
(79)

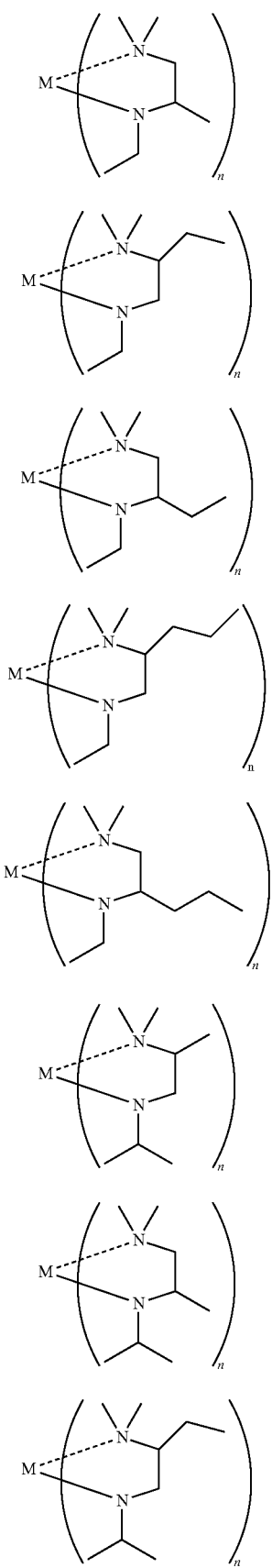
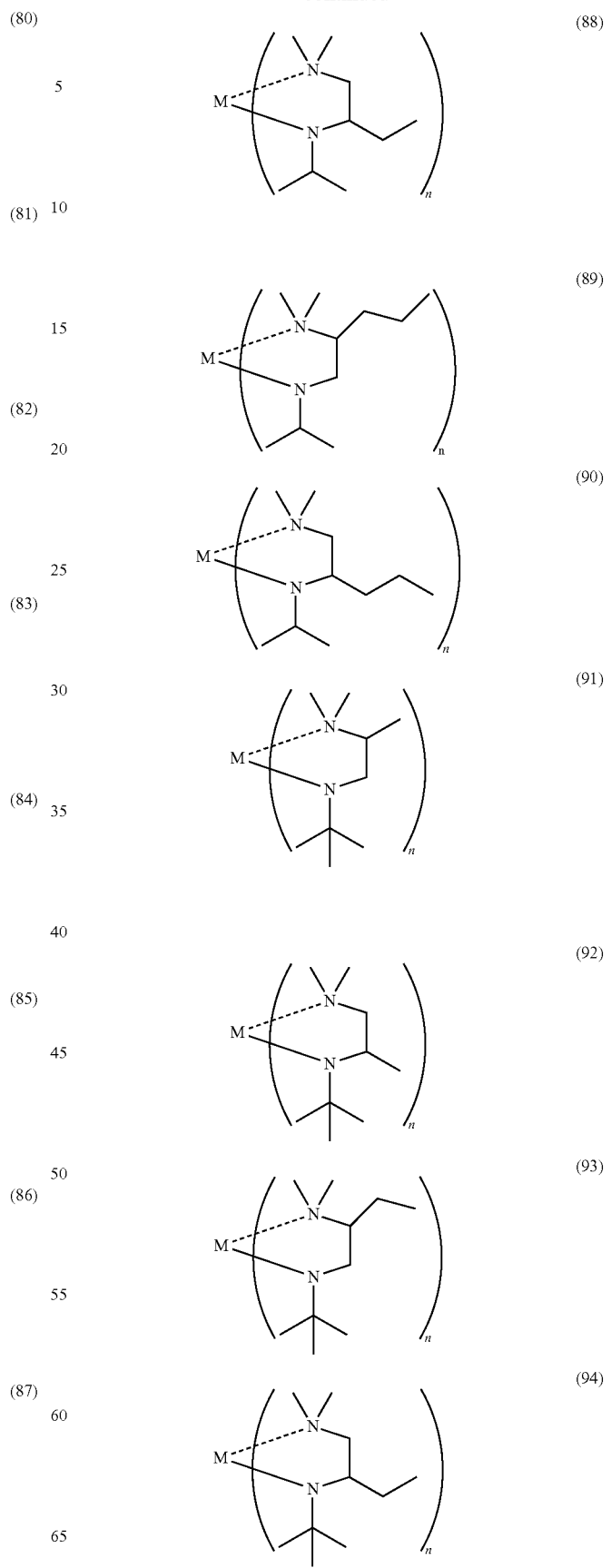

(95) 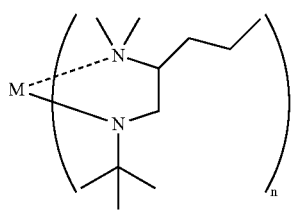
(96) 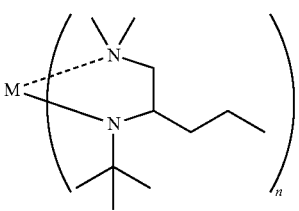
(97) 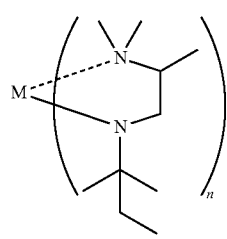
(98) 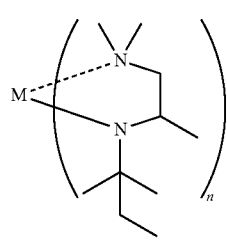
(99) 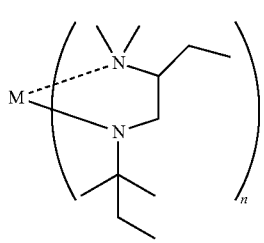
(100) 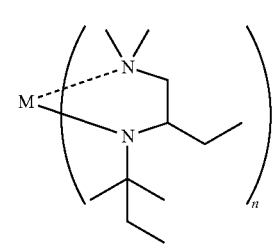
(101) 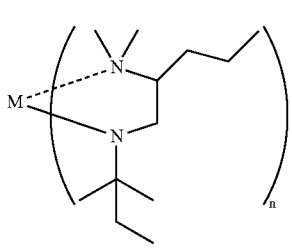
(102) 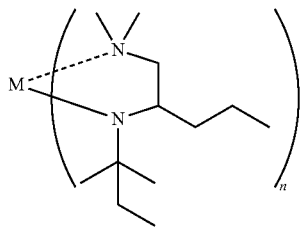
(103) 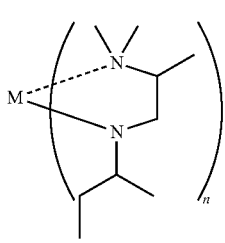
(104) 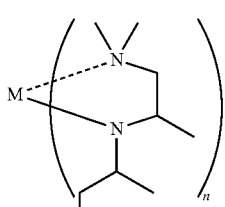
(105) 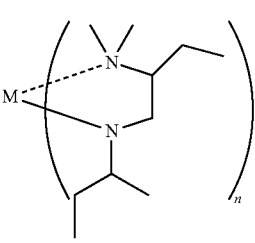
(106) 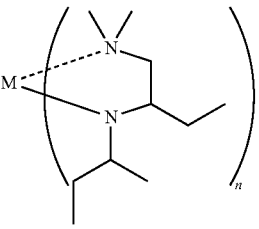
(107) 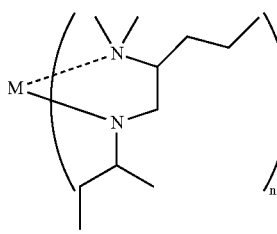
(108) 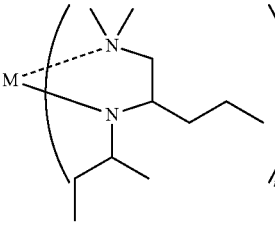

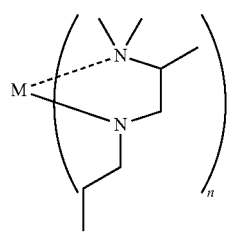
(109)
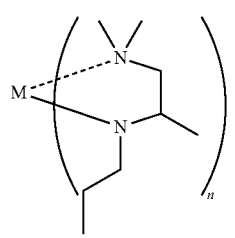
(110)
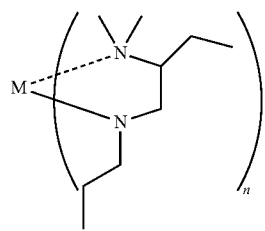
(111)
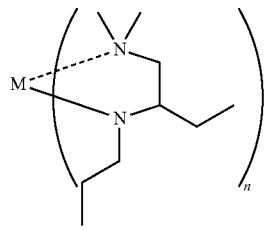
(112)
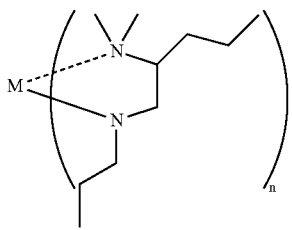
(113)
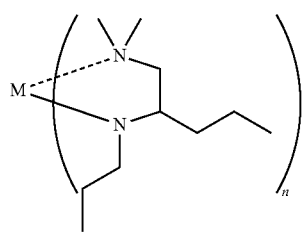
(114)
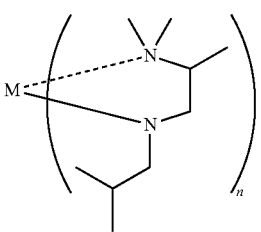
(115)
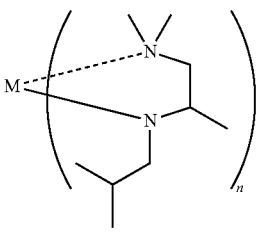
(116)
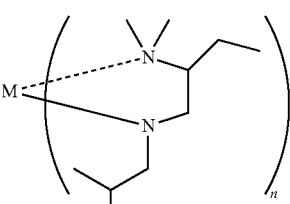
(117)
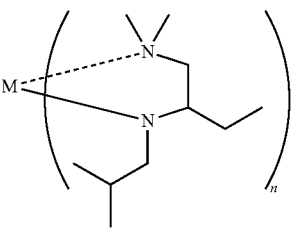
(118)
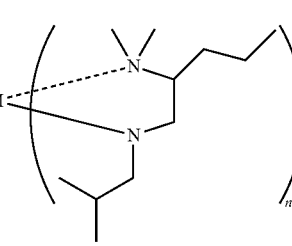
(119)
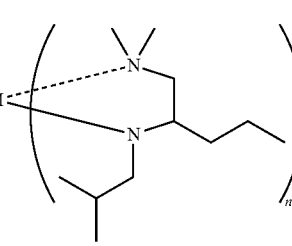
(120)
(121)

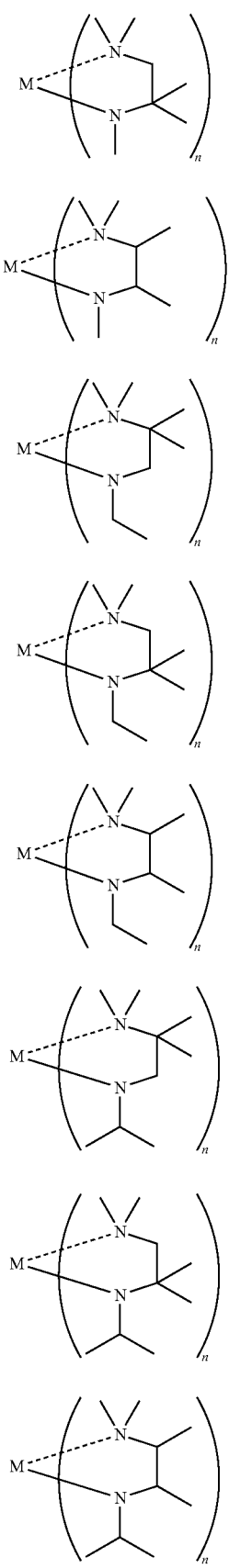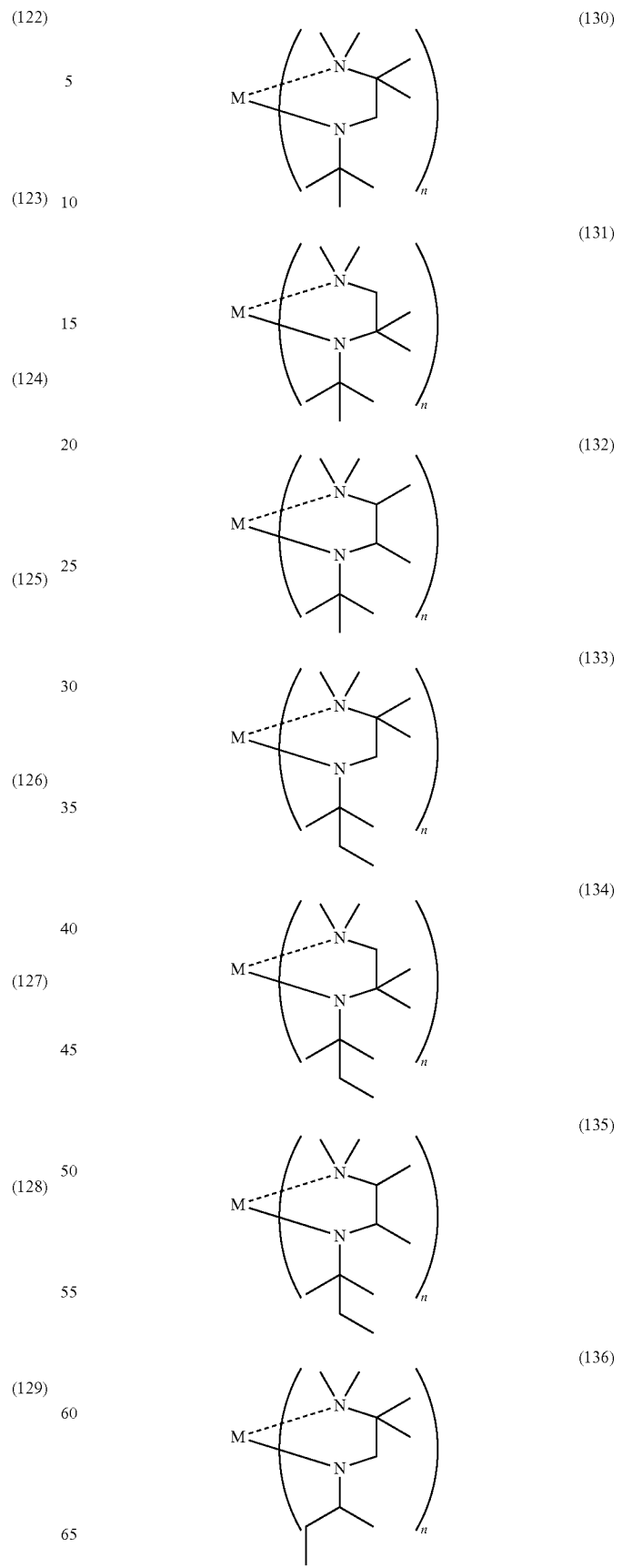

(137)
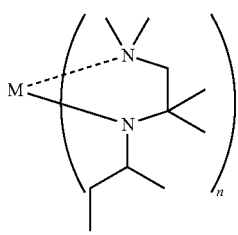
(138)
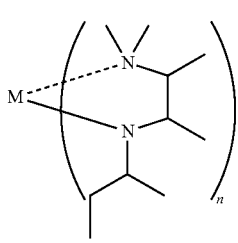
(139)
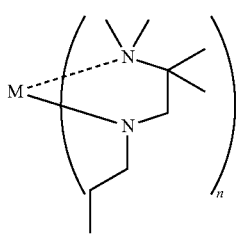
(140)
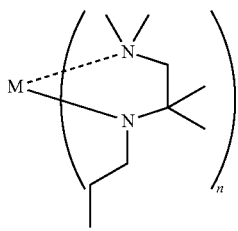
(141)
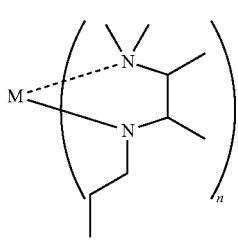
(142)
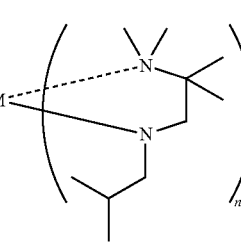
(143)
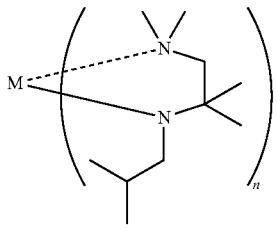
(144)
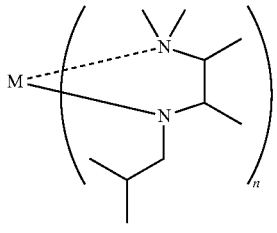
(145)
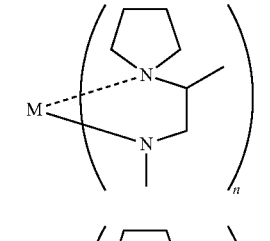
(146)
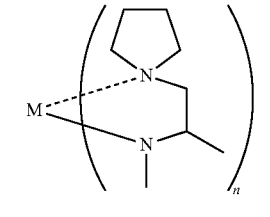
(147)
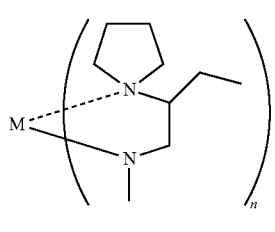
(148)
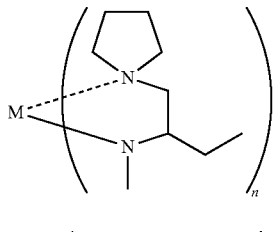
(149)
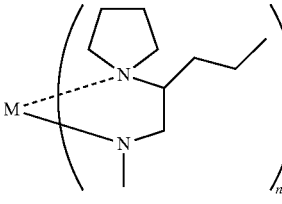

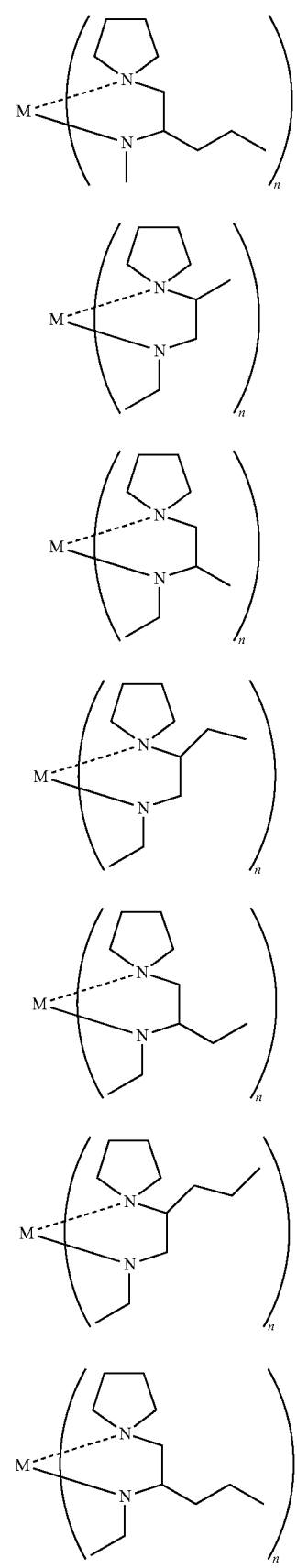
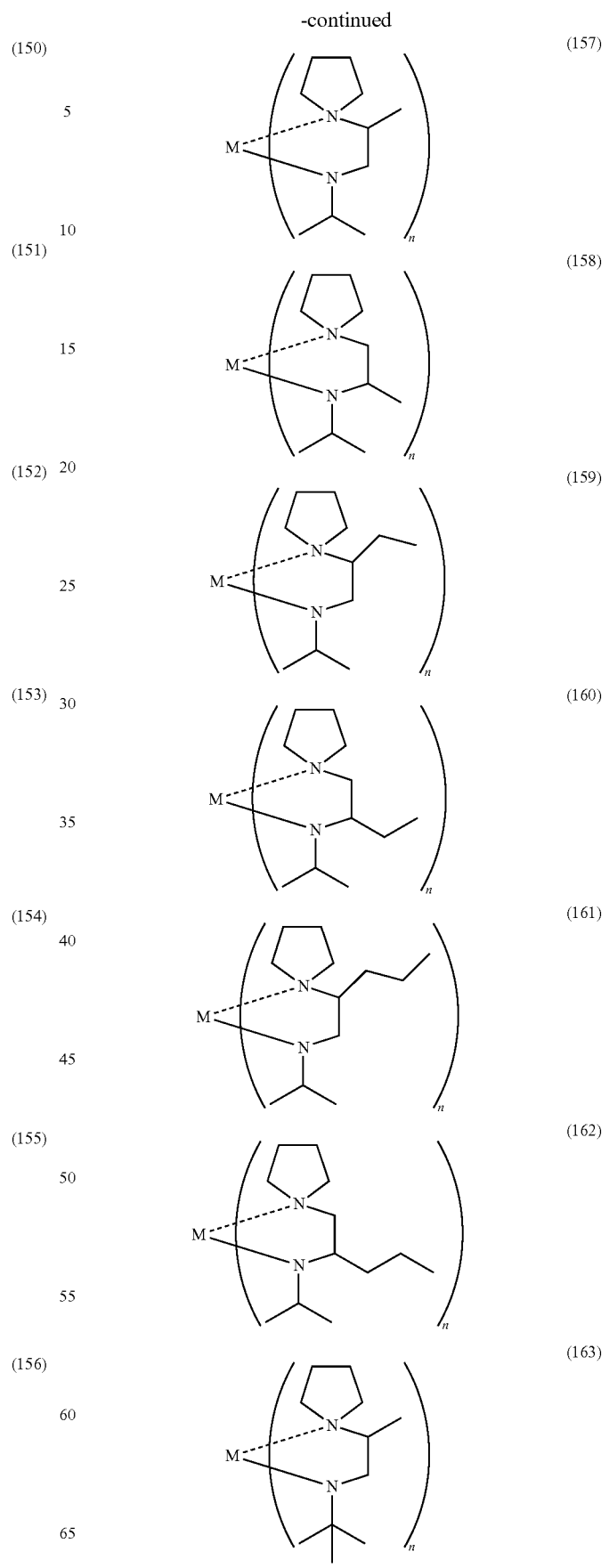

-continued
(164)
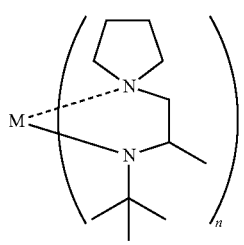
(165)
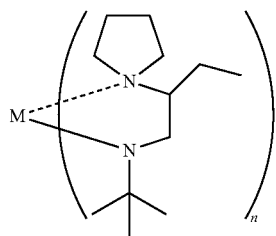
(166)
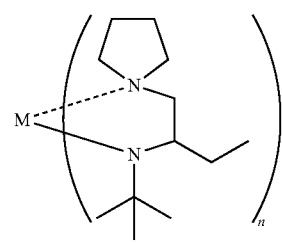
(167)
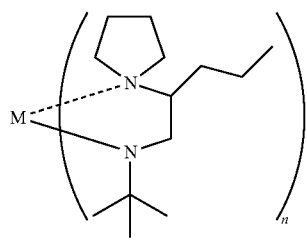
(168)
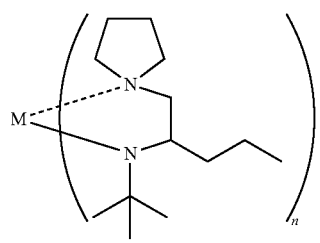
(169)
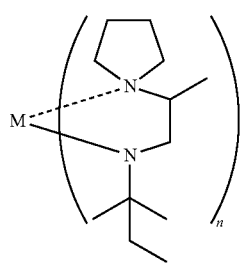
-continued
(170)
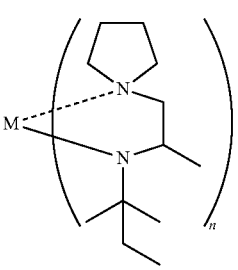
(171)
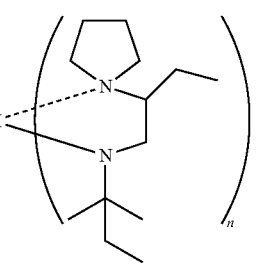
(172)
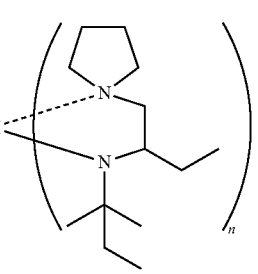
(173)
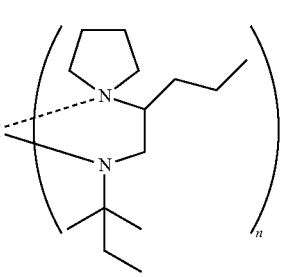
(174)
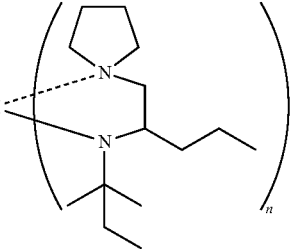
(175)
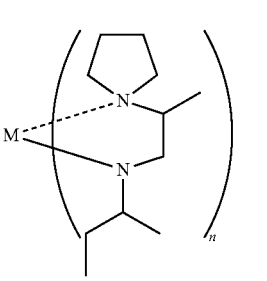

(176) 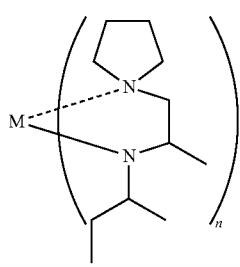
(177) 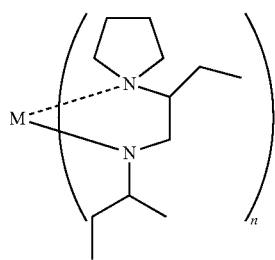
(178) 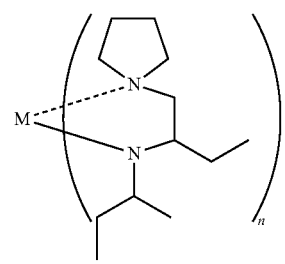
(179) 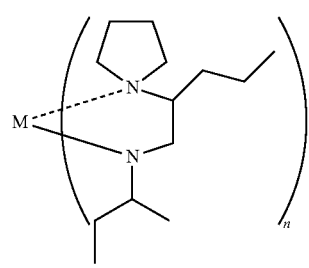
(180) 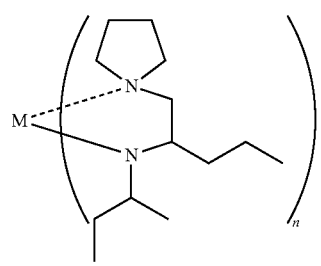
(181) 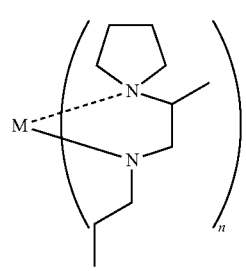
(182) 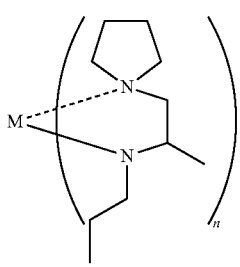
(183) 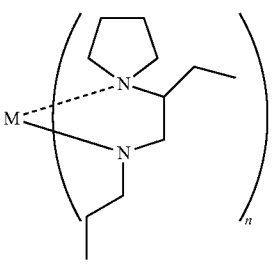
(184) 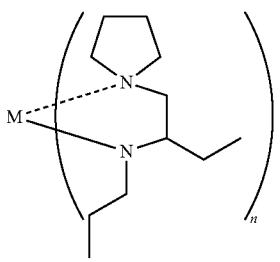
(185) 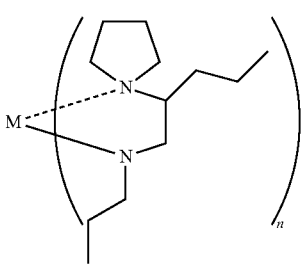
(186) 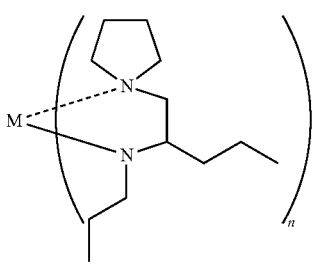
(187) 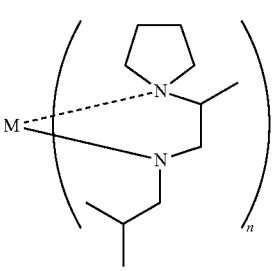

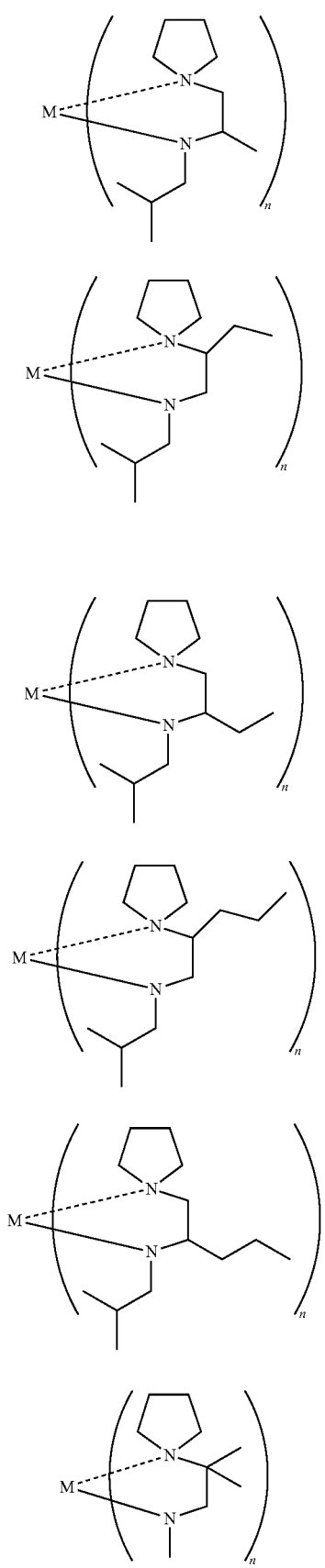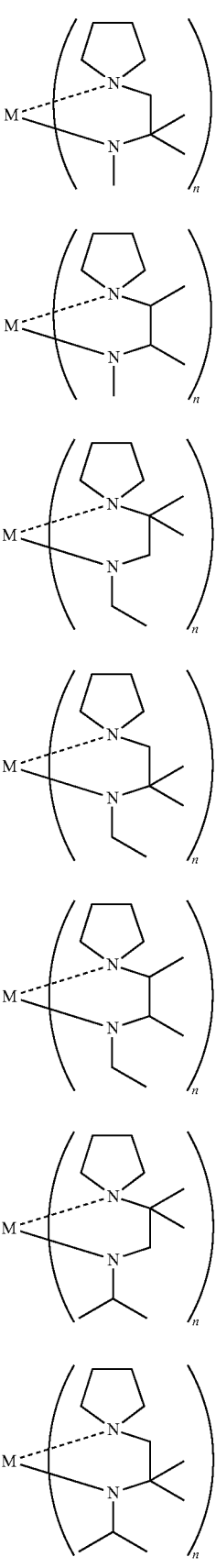

(201) 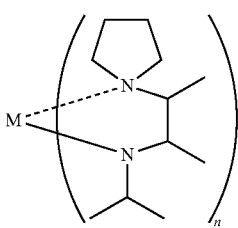
(202) 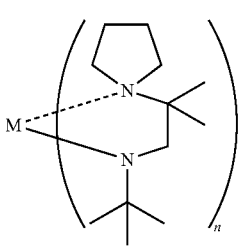
(203) 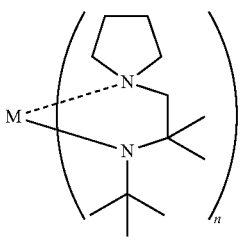
(204) 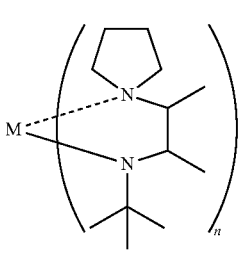
(205) 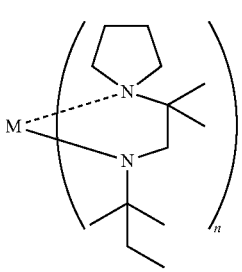
(206) 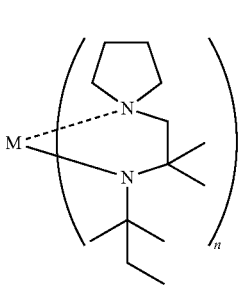
(207) 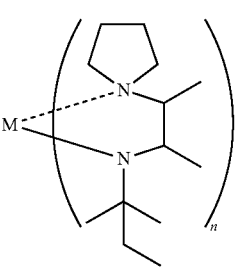
(208) 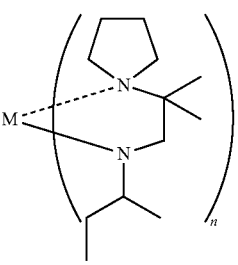
(209) 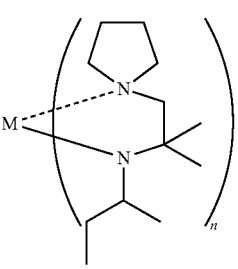
(210) 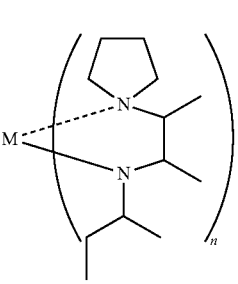
(211) 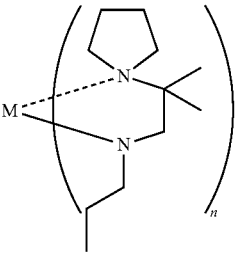
(212) 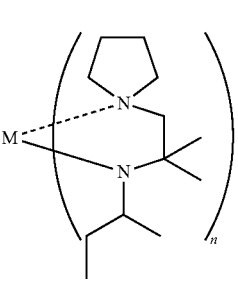

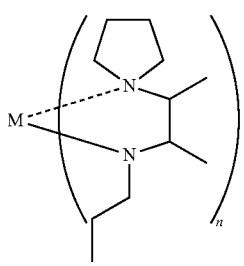
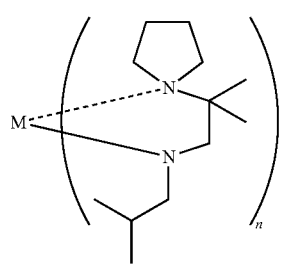
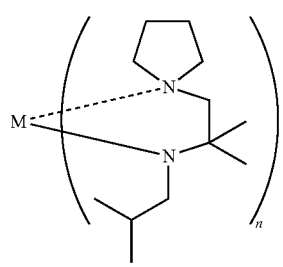
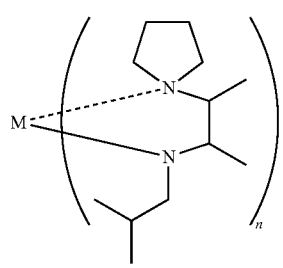
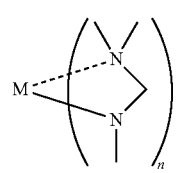
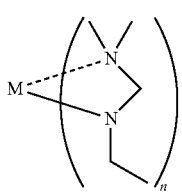
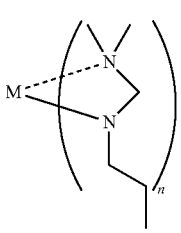

(226)
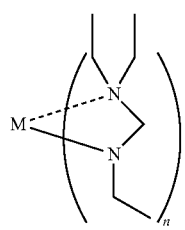
(227)
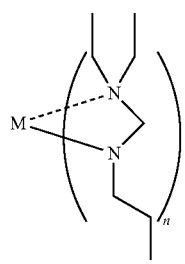
(228)
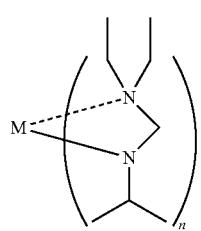
(229)
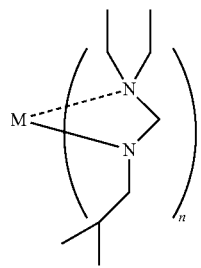
(230)
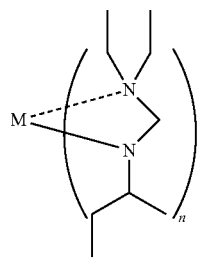
(231)
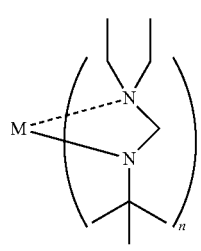
(232)
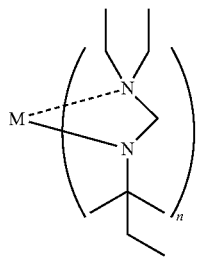
(233)
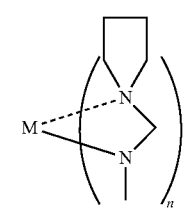
(234)
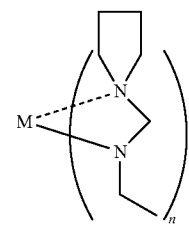
(235)
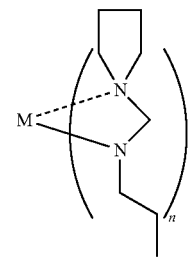
(236)
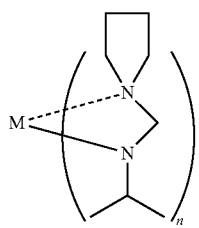
(237)
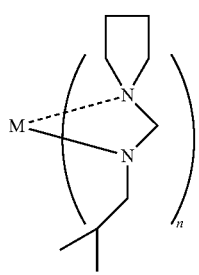

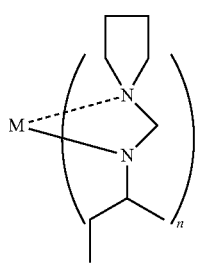 (238)
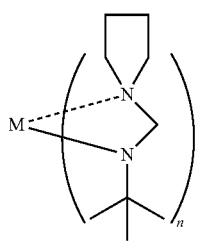 (239)
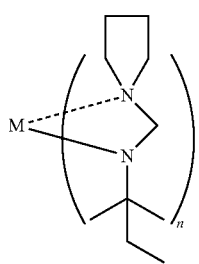 (240)
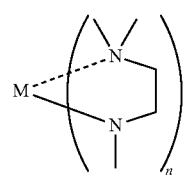 (241)
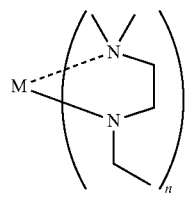 (242)
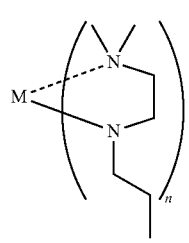 (243)
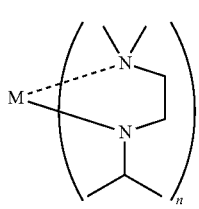 (244)
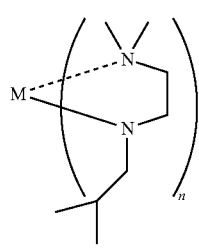 (245)
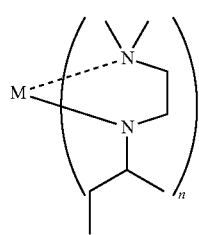 (246)
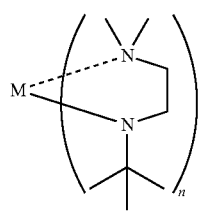 (247)
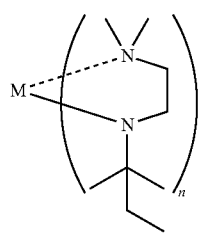 (248)
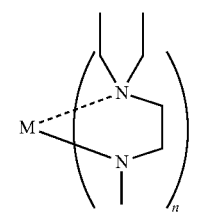 (249)
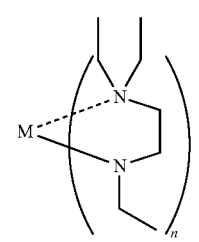 (250)

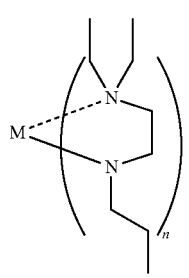 (251)
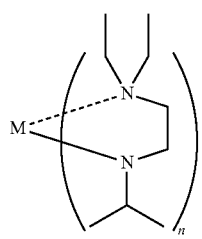 (252)
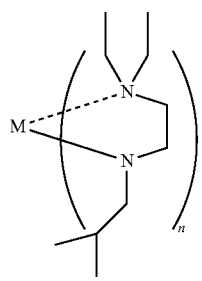 (253)
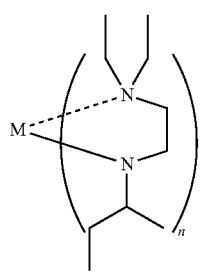 (254)
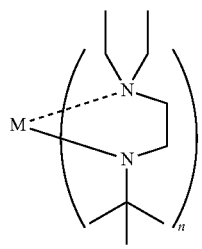 (255)
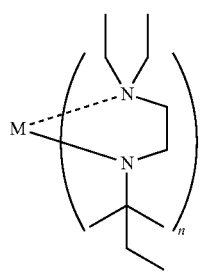 (256)
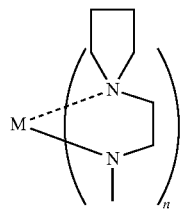 (257)
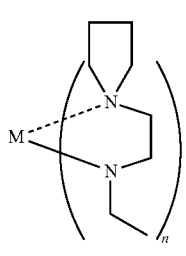 (258)
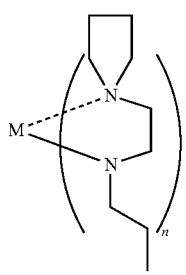 (259)
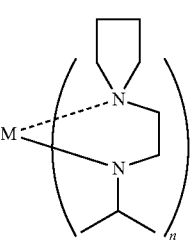 (260)
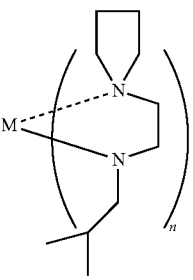 (261)
(262)

(263) 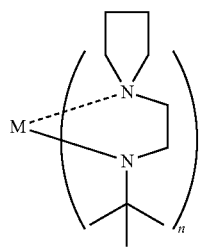
(264) 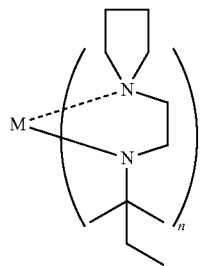
(265) 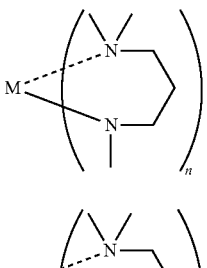
(266) 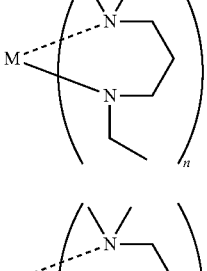
(267) 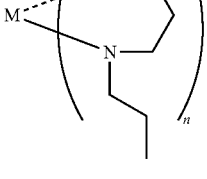
(268) 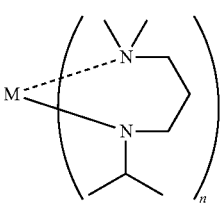
(269) 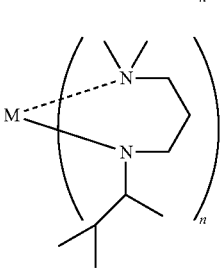
(270) 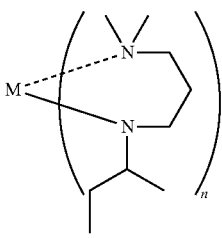
(271) 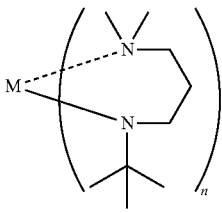
(272) 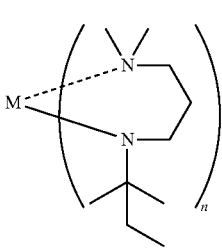
(273) 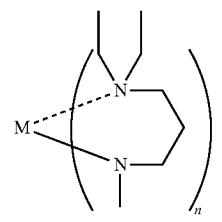
(274) 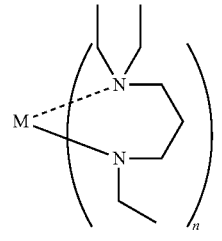
(275) 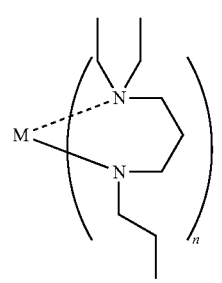

(276) 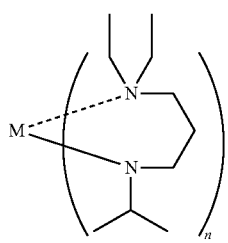
(277) 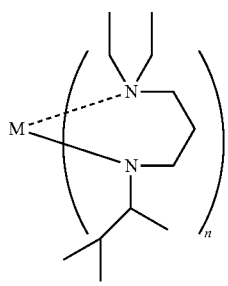
(278) 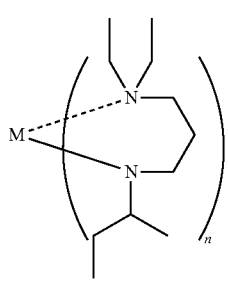
(279) 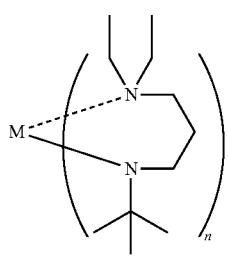
(280) 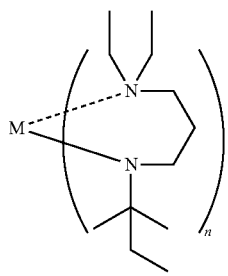
(281) 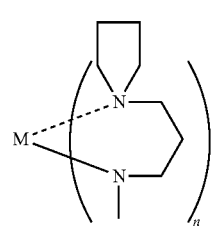
(282) 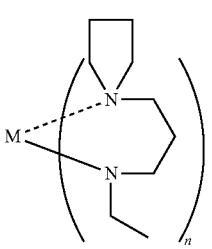
(283) 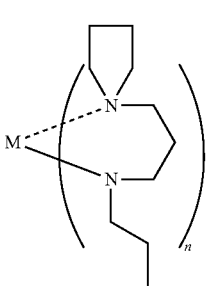
(284) 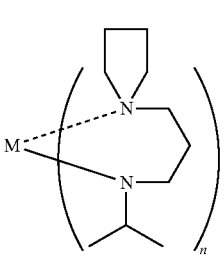
(285) 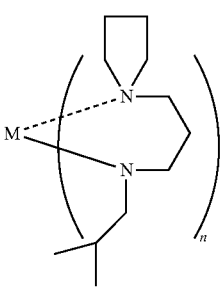
(286) 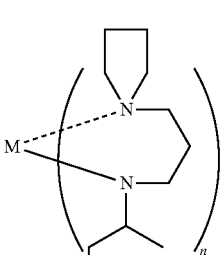
(287) 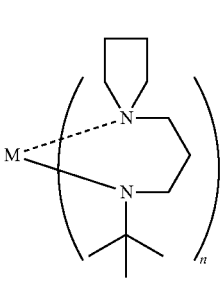

(288)
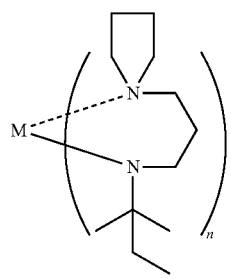
(289)
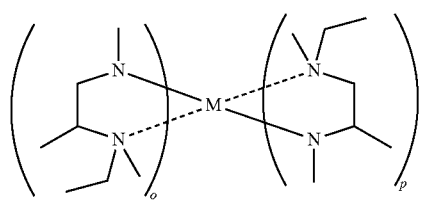
(290)
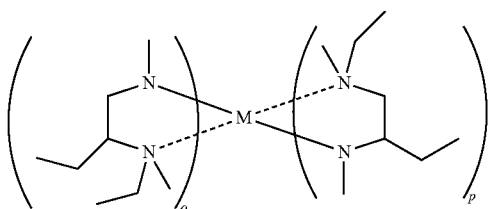
(291)
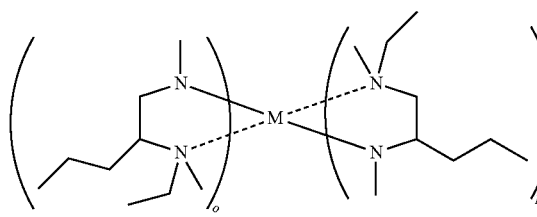
(292)
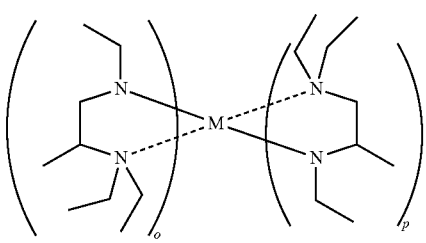
(293)
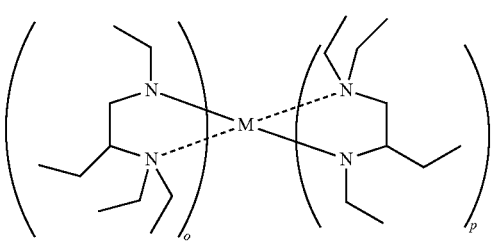
(294)
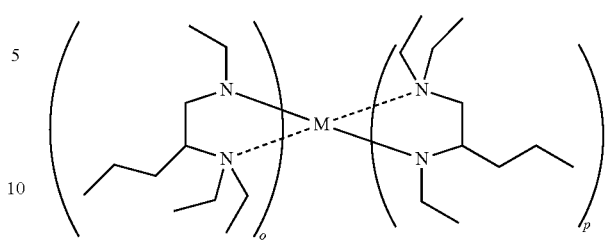
(295)
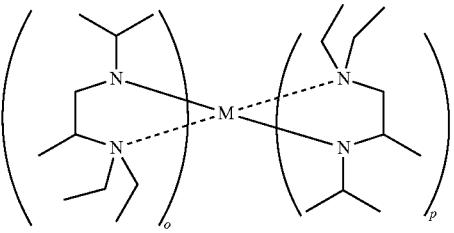
(296)
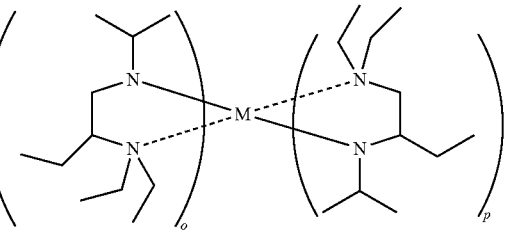
(297)
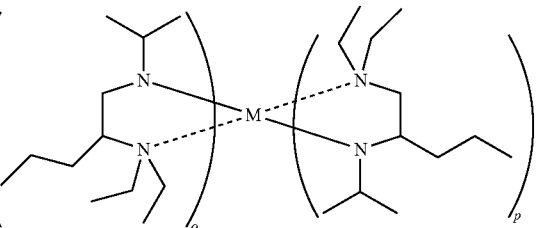
(298)
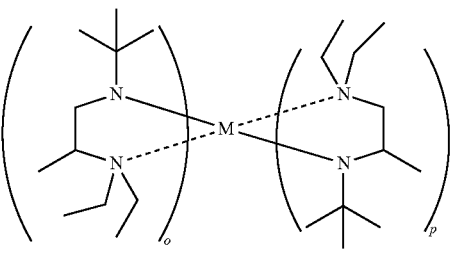
(299)
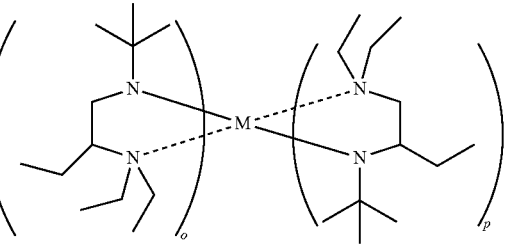

(300)
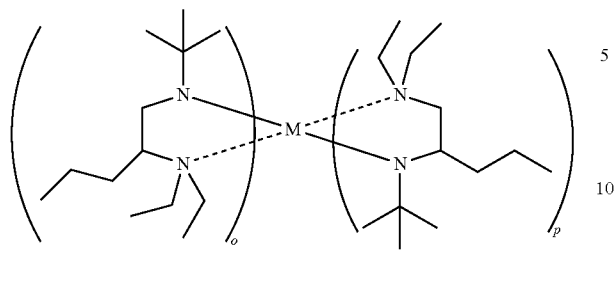
(301)
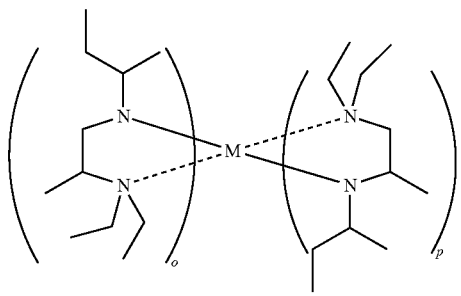
(302)
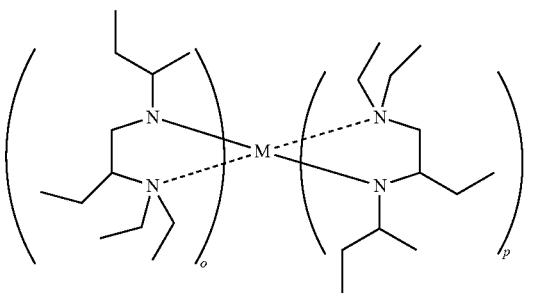
(303)
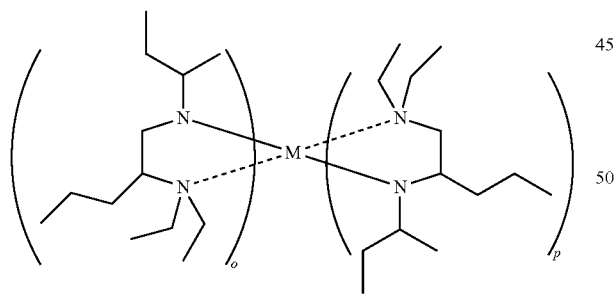
(304)
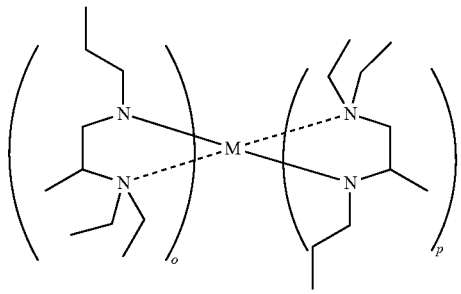
(305)
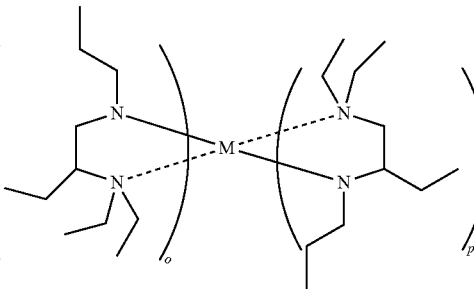
(306)
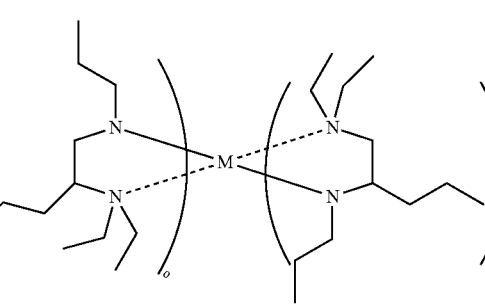
(307)
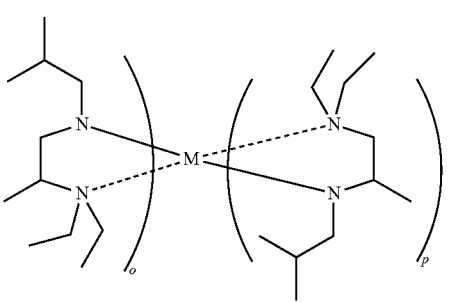
(308)
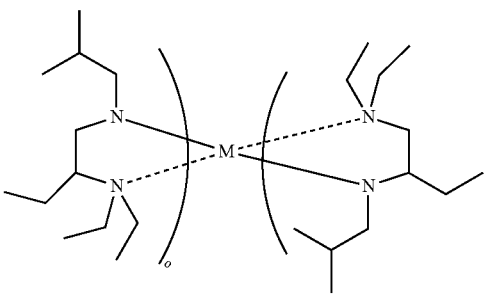
(309)
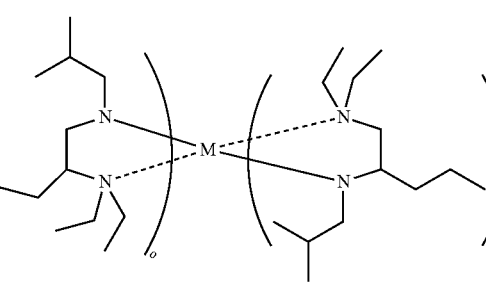

(310)
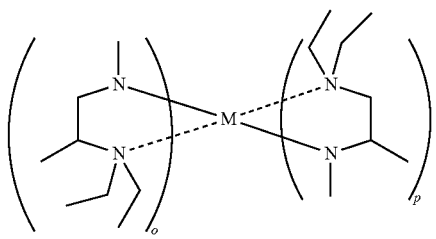
(311)
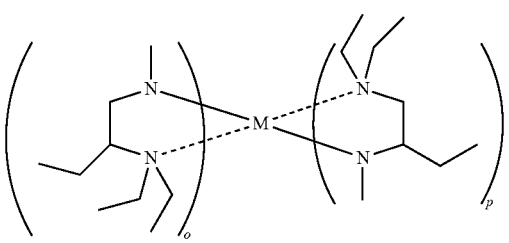
(312)
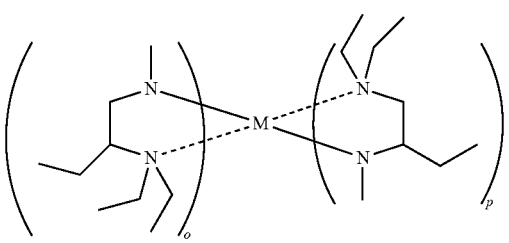
(313)
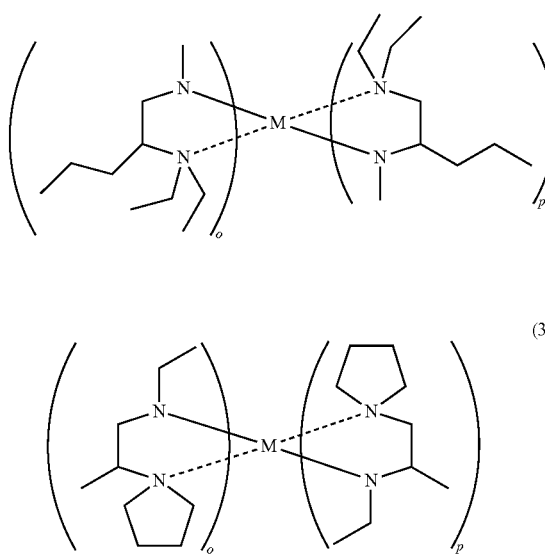
(314)
(315)
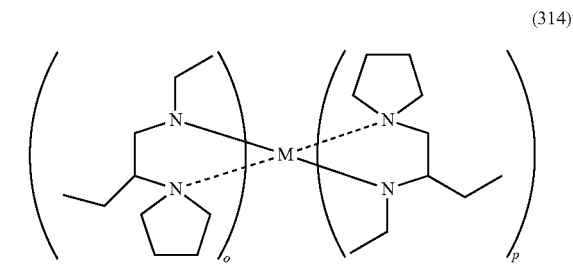
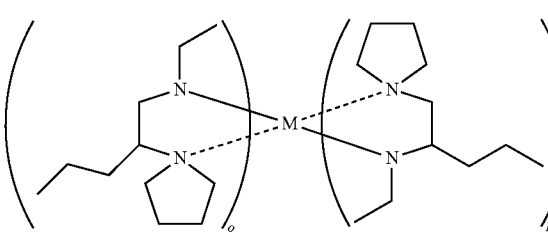
(316)
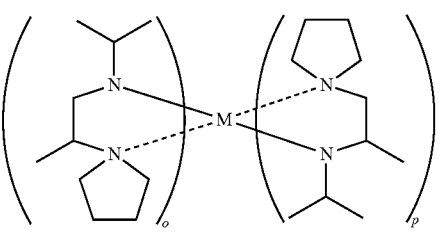
(317)
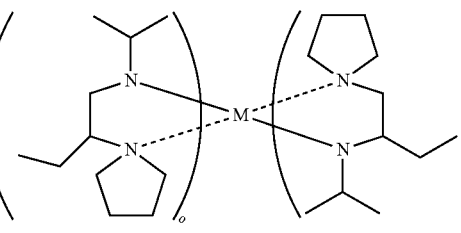
(318)
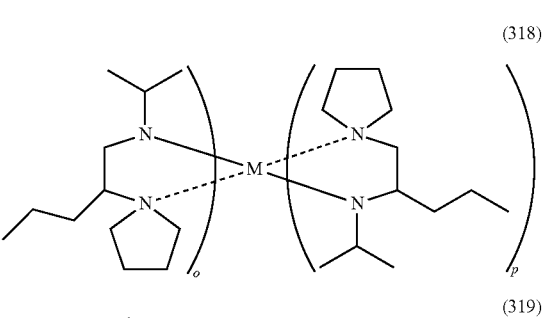
(319)
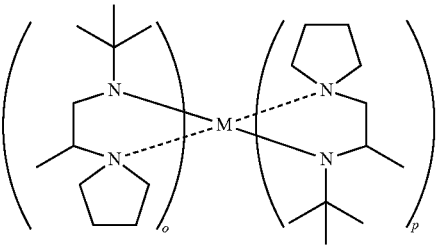
(320)
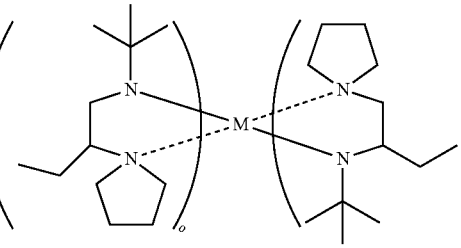
(321)
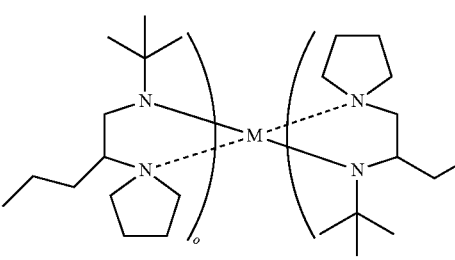

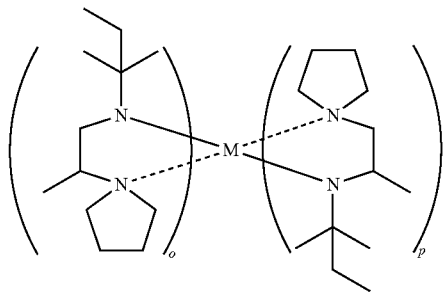
(322)
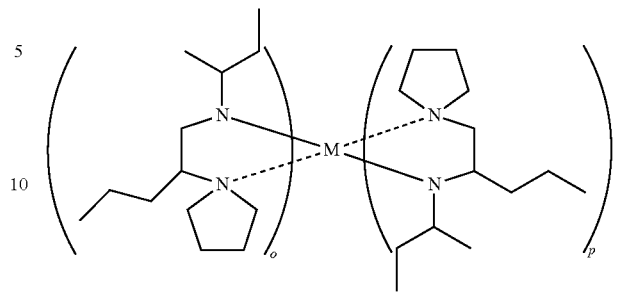
(327)
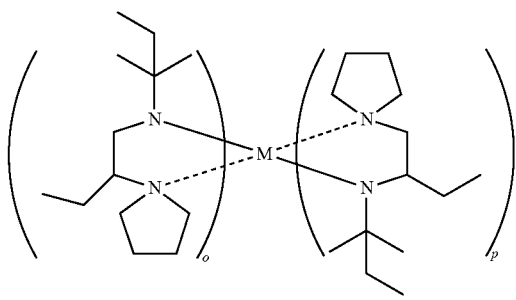
(323)
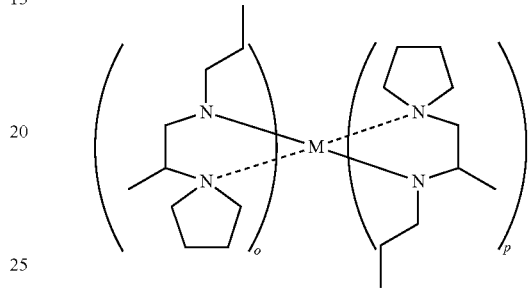
(328)
(324)
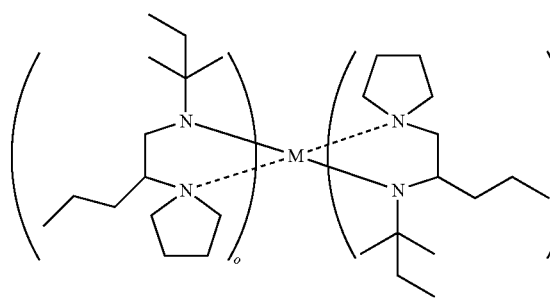
(329)
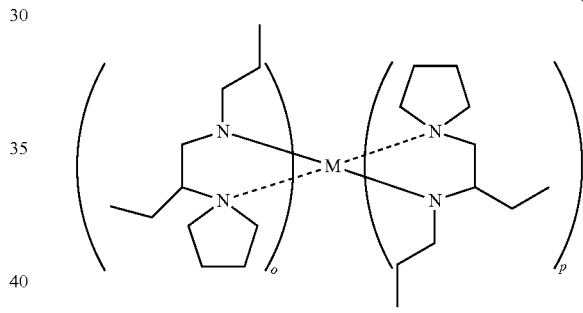
(325)
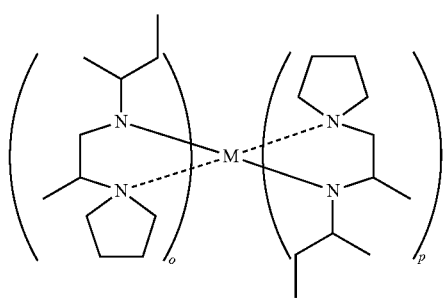
(330)
(326)
(331)
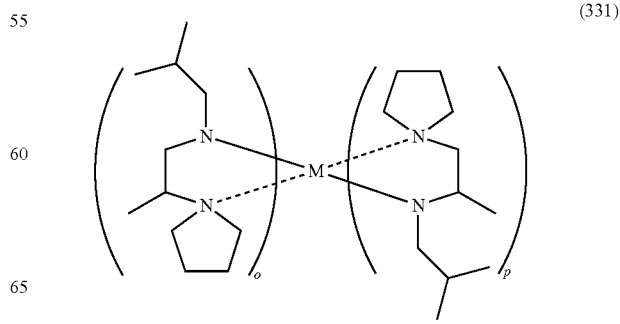

-continued
(332)
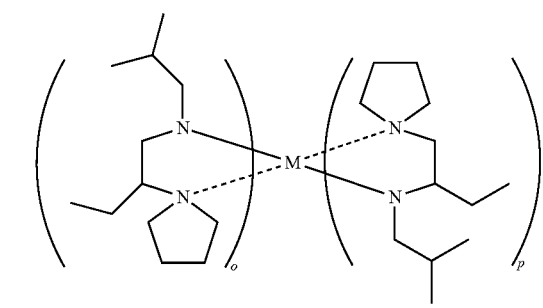
(333)
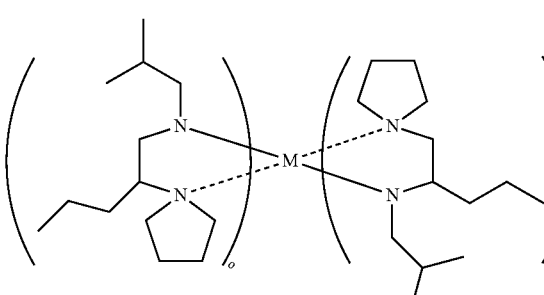
(334)
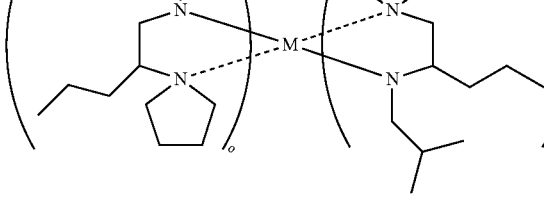
(335)
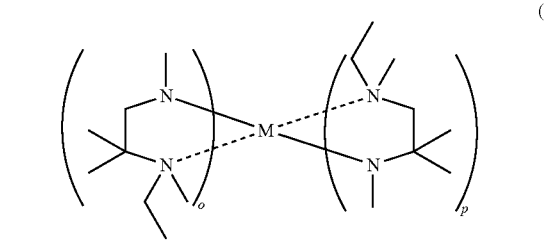
(336)
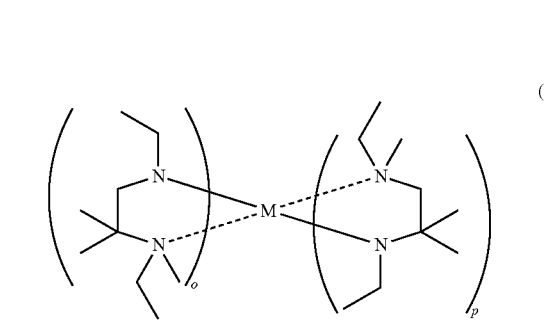
(337)
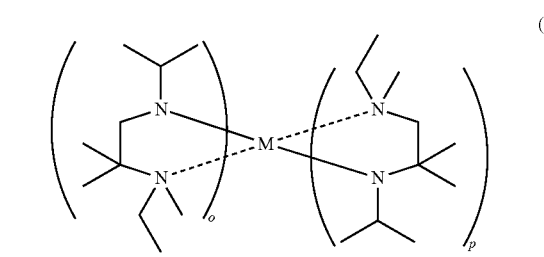
(337)
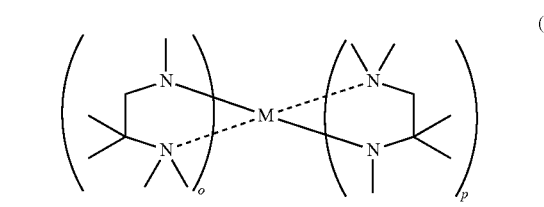
-continued
(338)
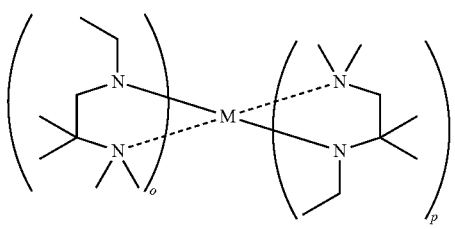
(339)
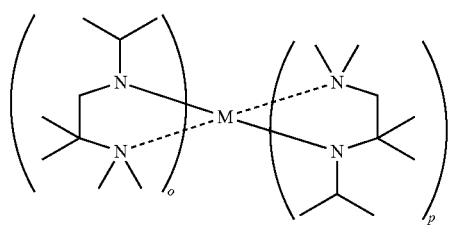
(340)
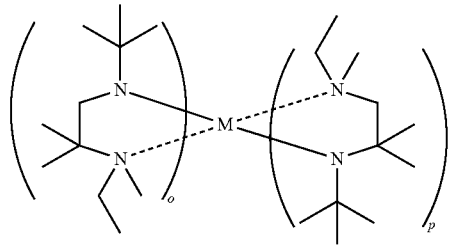
(341)
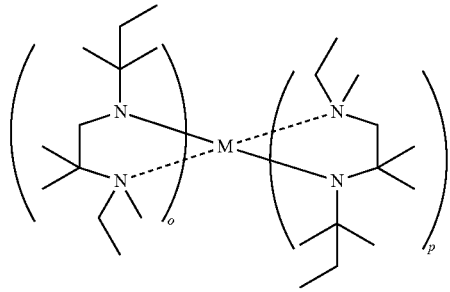
(342)
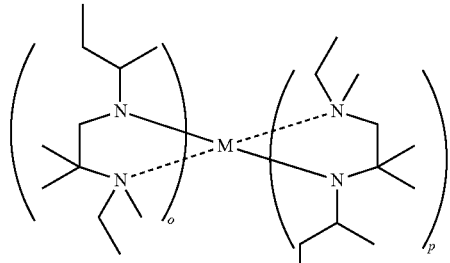
(343)
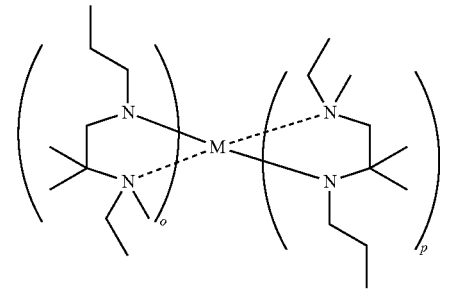

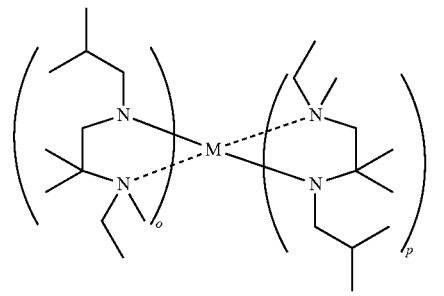
(344)
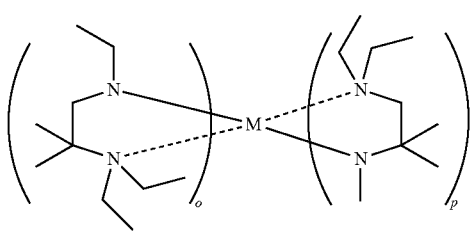
(345)
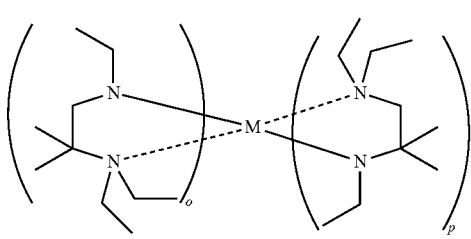
(346)
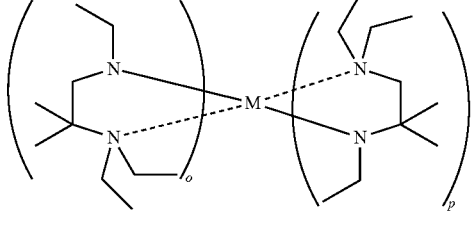
(347)
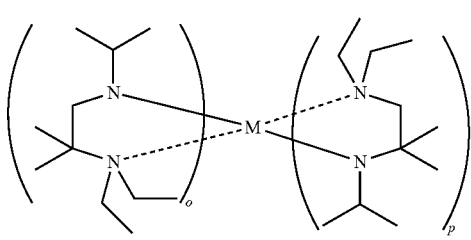
(348)
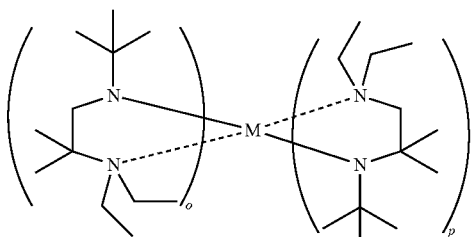
(349)
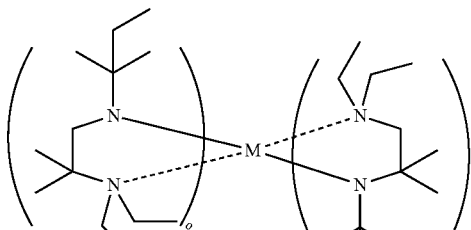
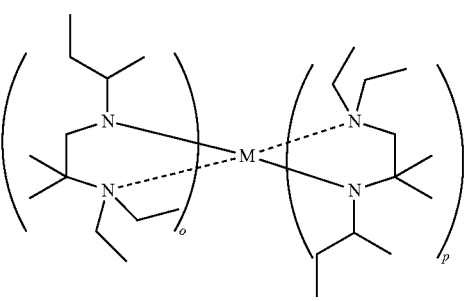
(350)
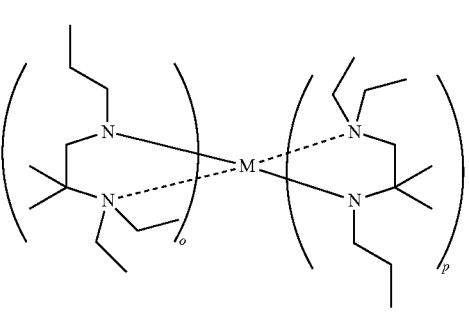
(351)
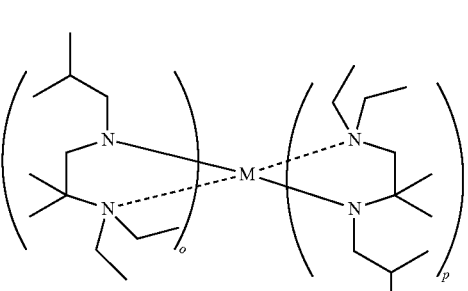
(352)
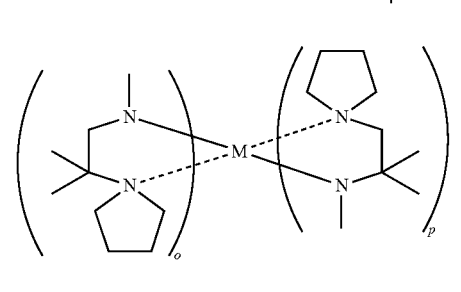
(353)
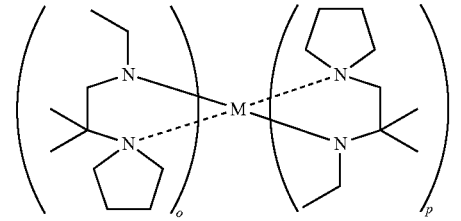
(354)
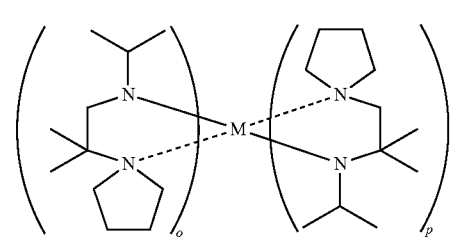
(355)

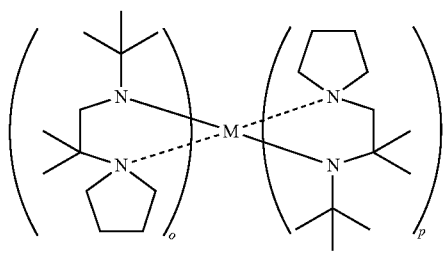
(356)
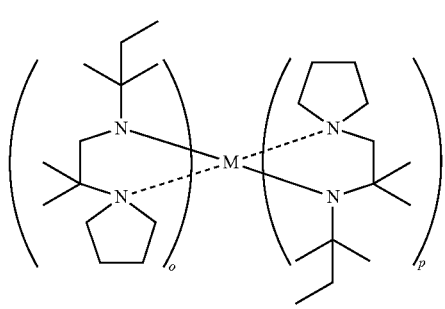
(357)
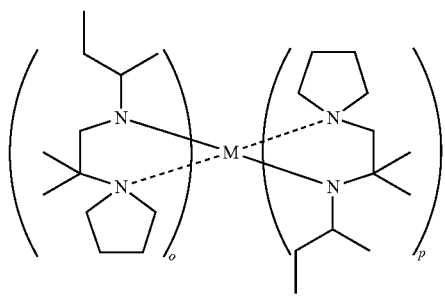
(358)
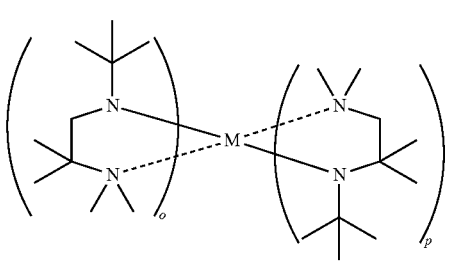
(359)
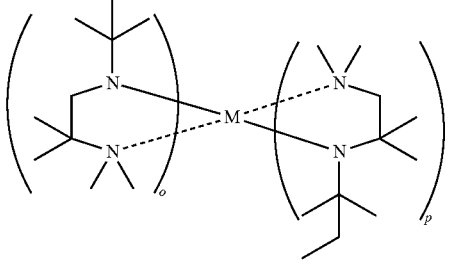
(360)
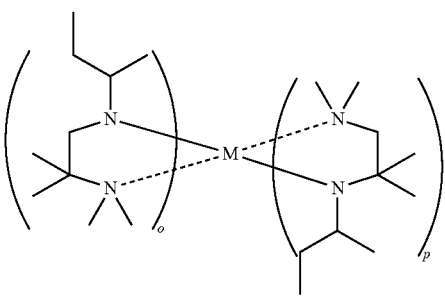
(361)
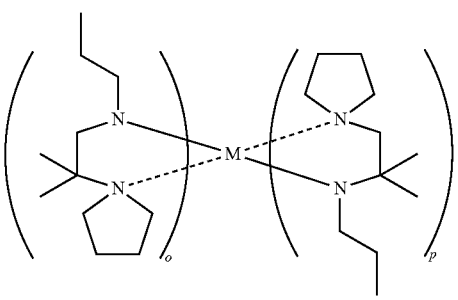
(362)
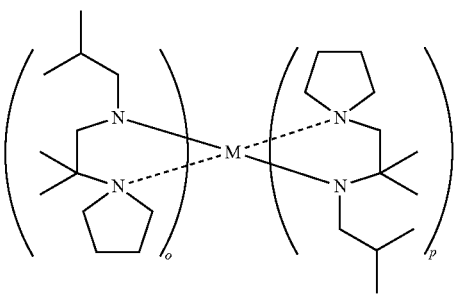
(363)
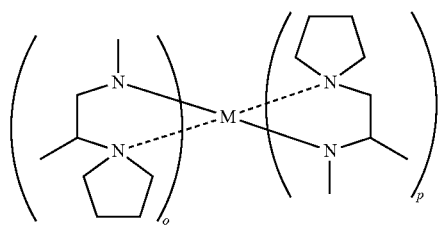
(364)
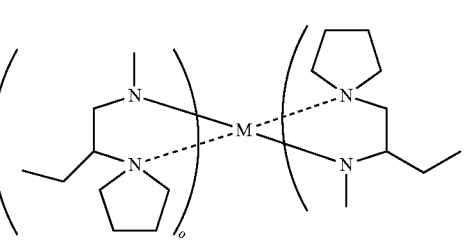
(365)
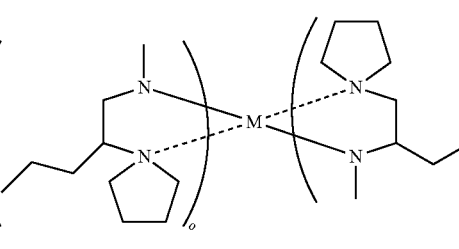
(366)

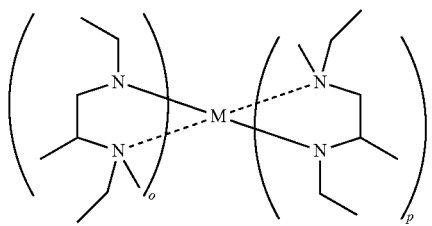
(367)
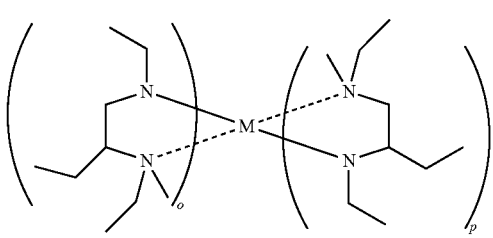
(368)
(369)
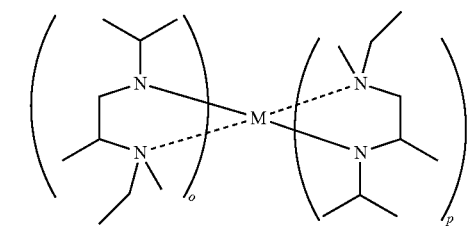
(370)
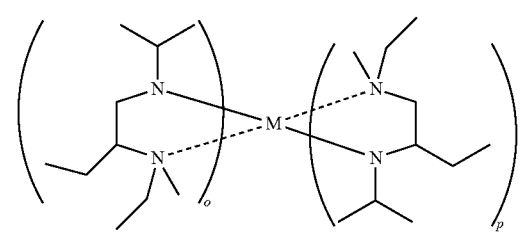
(371)
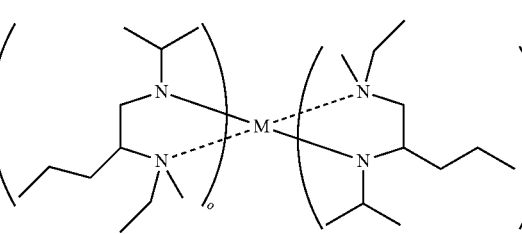
(372)
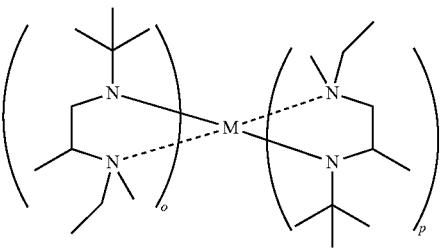
(373)
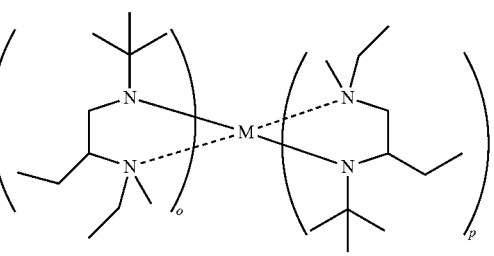
(374)
(375)
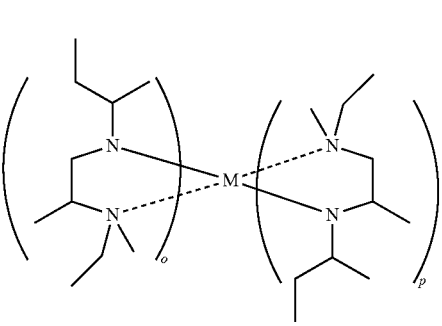
(376)
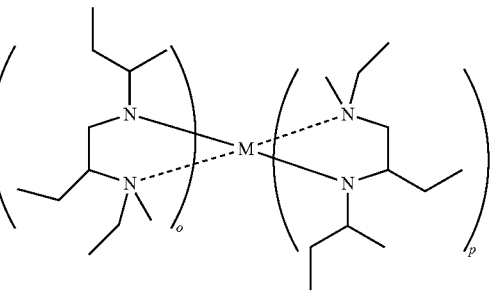
(377)

(378) 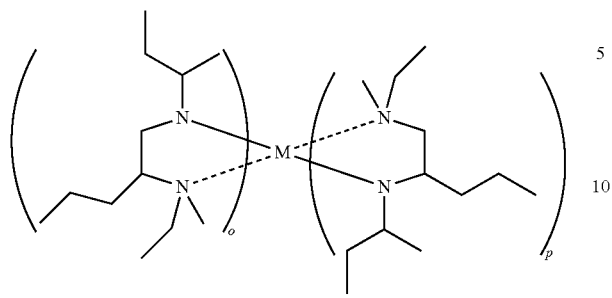
(379) 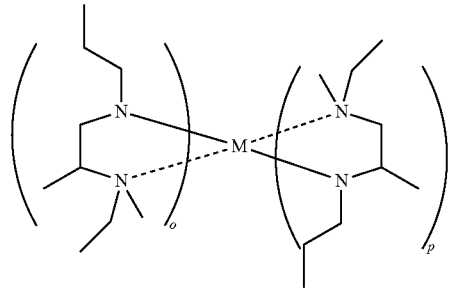
(380) 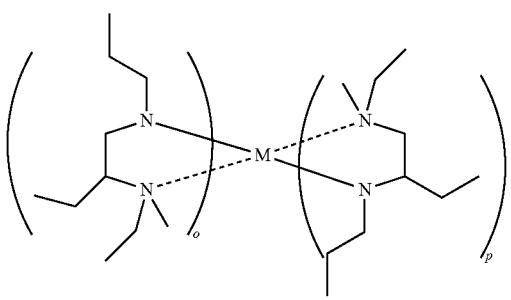
(381) 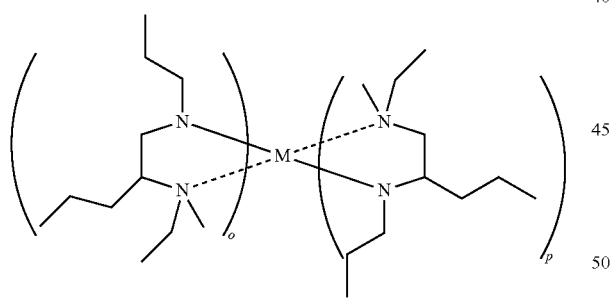
(382) 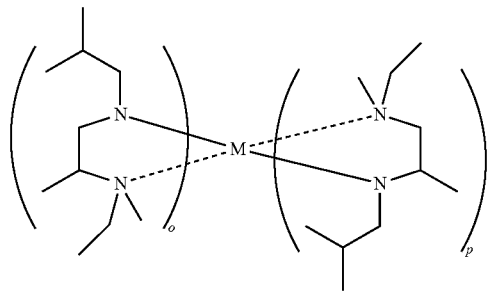
(383) 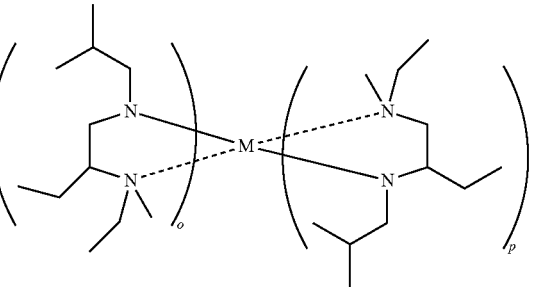
(384) 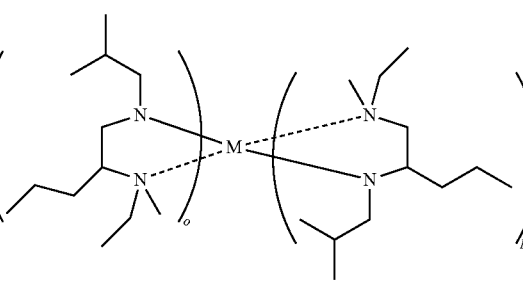
(385) 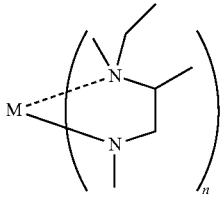
(386) 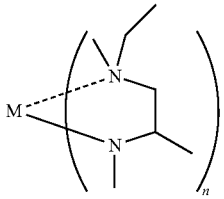
(387) 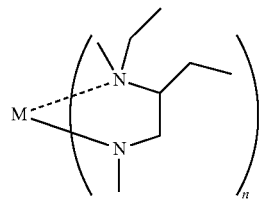
(388) 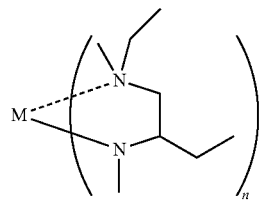

(389)
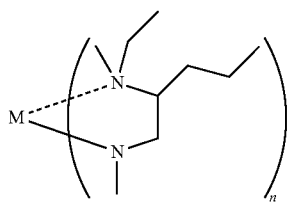
(390)
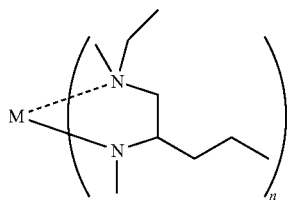
(391)
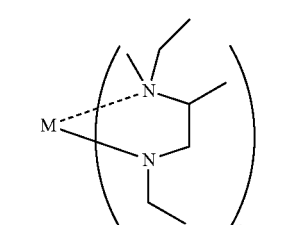
(392)
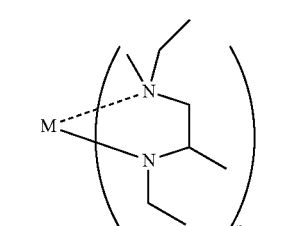
(393)
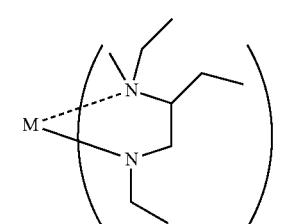
(394)
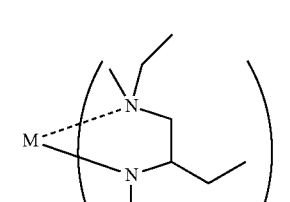
(395)
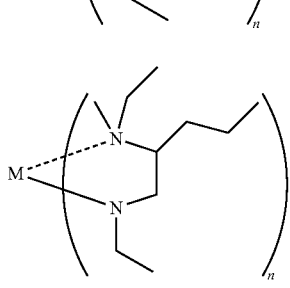
(396)
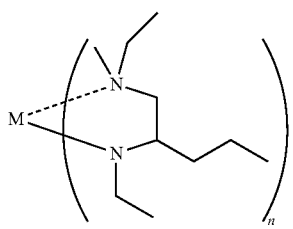
(397)
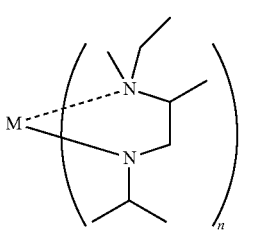
(398)
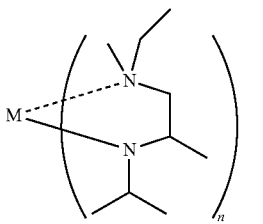
(399)
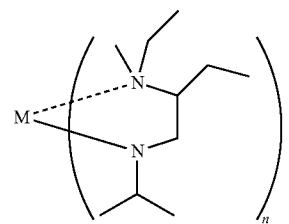
(400)
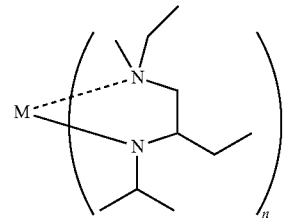
(401)
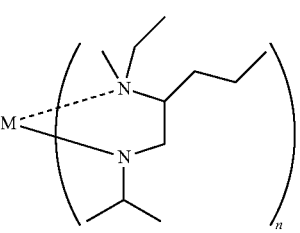
(402)
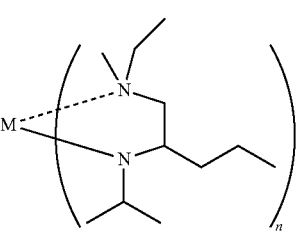

(403)
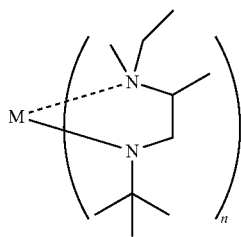
(404)
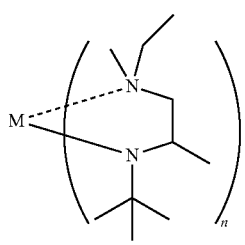
(405)
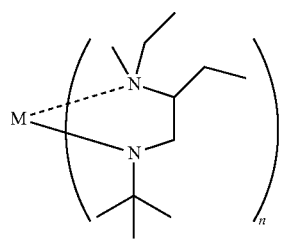
(406)
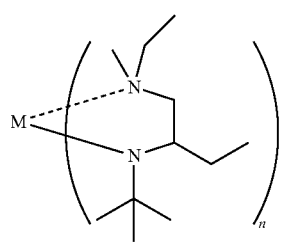
(407)
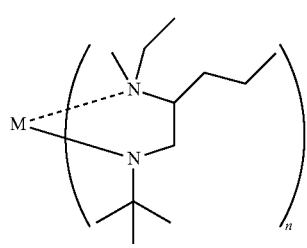
(408)
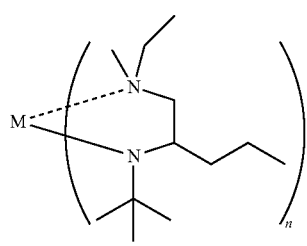
(409)
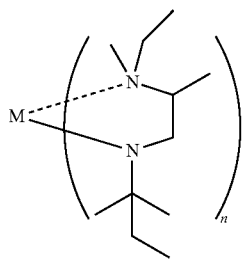
(410)
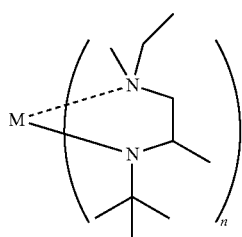
(411)
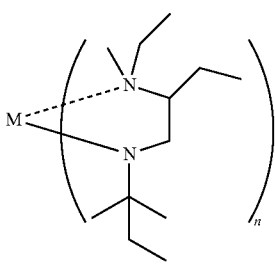
(412)
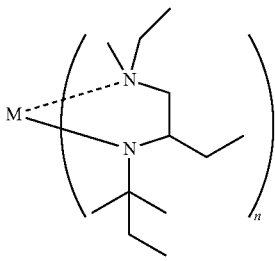
(413)
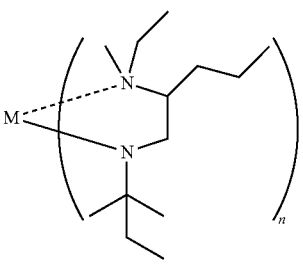
(414)
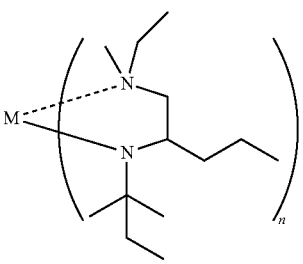

75
-continued
(415)
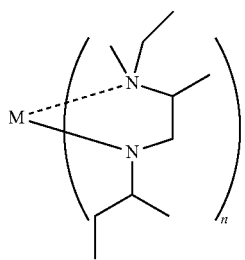
(416)
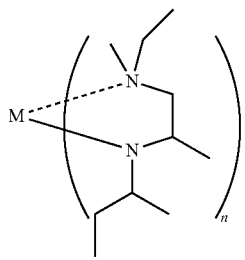
(417)
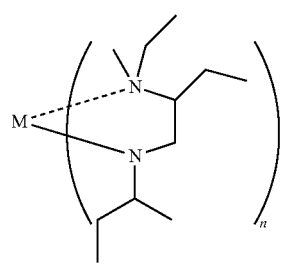
(418)
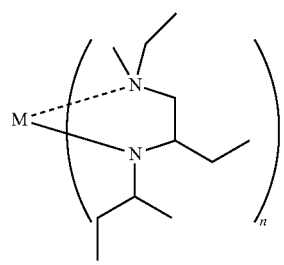
(419)
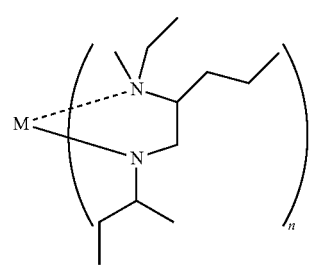
(420)
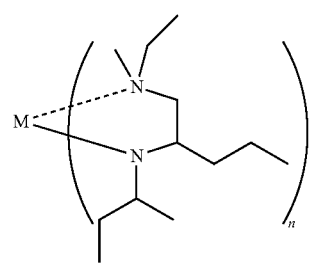
76
-continued
(421)
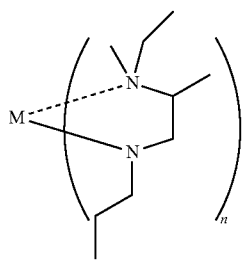
(422)
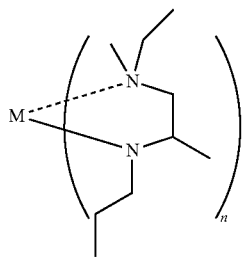
(423)
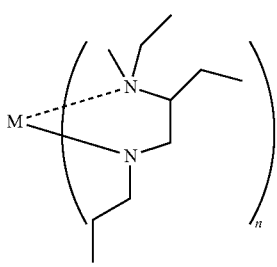
(424)
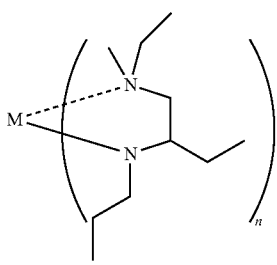
(425)
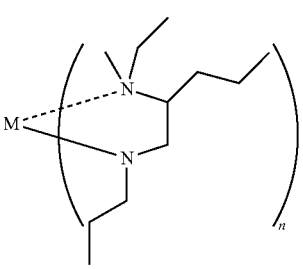
(426)
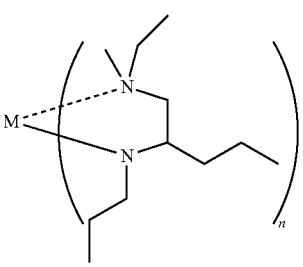

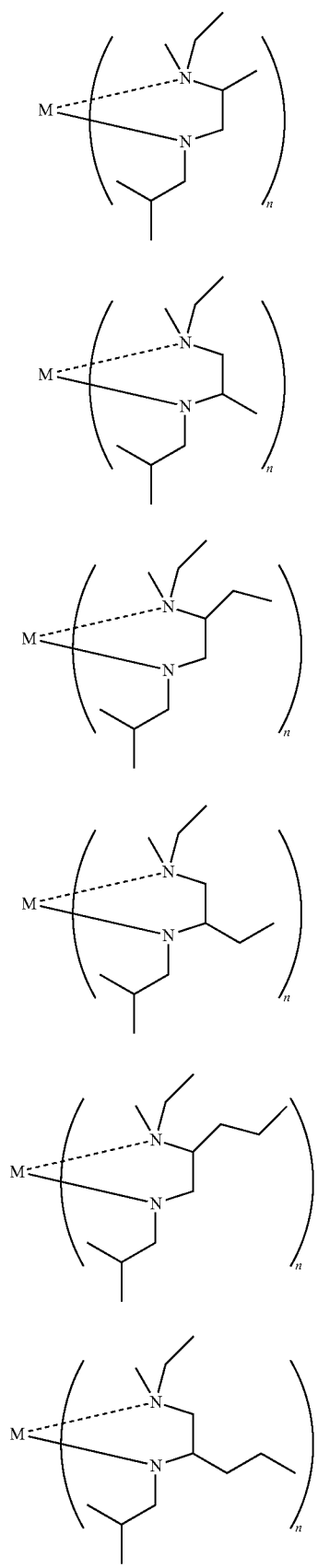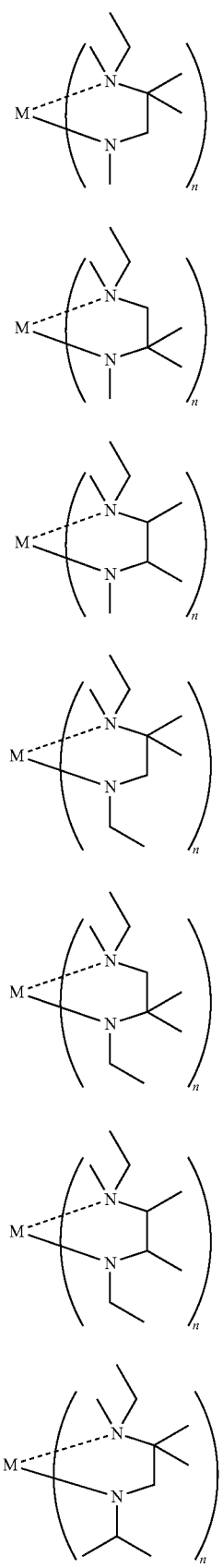

(440) 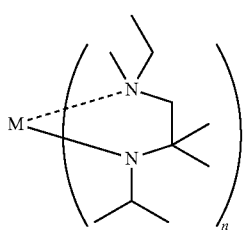
(441) 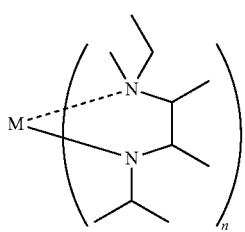
(442) 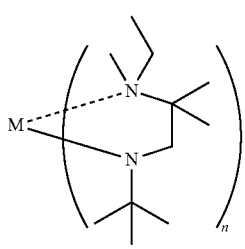
(443) 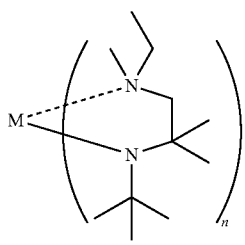
(444) 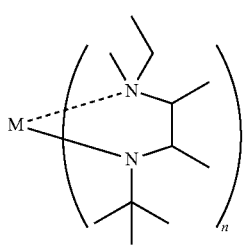
(445) 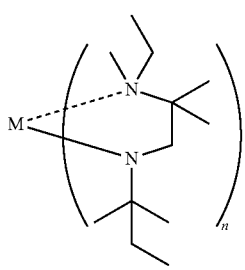
(446) 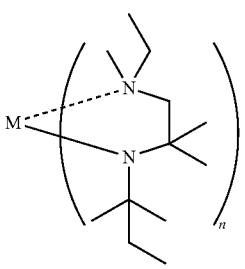
(447) 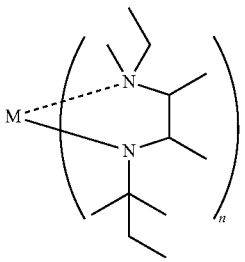
(448) 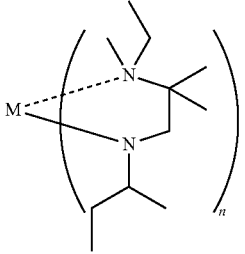
(449) 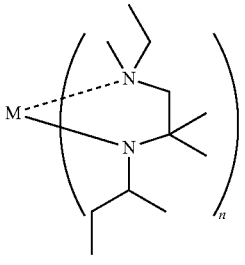
(450) 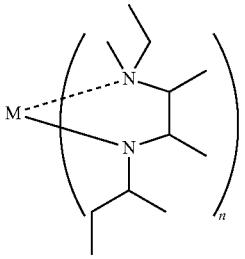
(451)

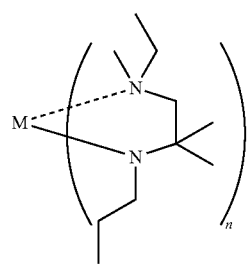
(452)
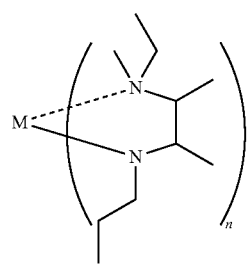
(453)
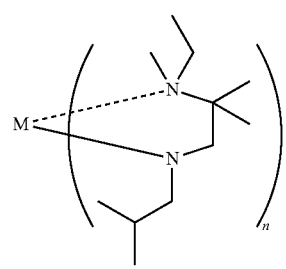
(454)
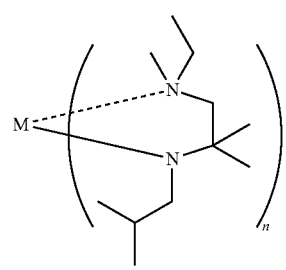
(455)
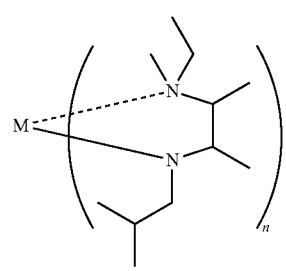
(456)
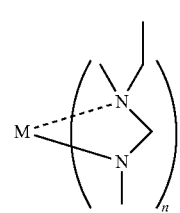
(457)
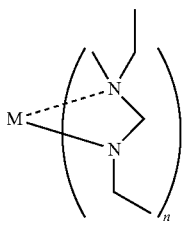
(458)
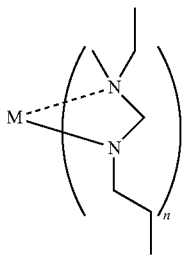
(459)
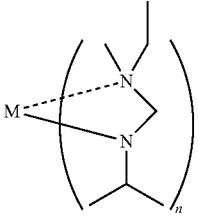
(460)
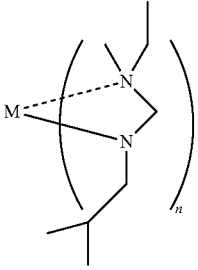
(461)
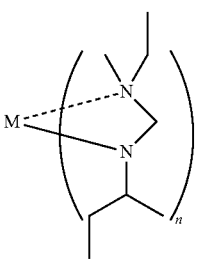
(462)
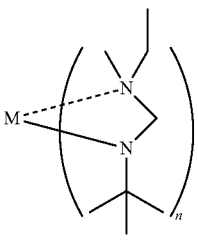
(463)

(464) 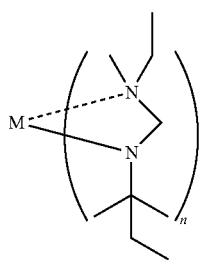
(465) 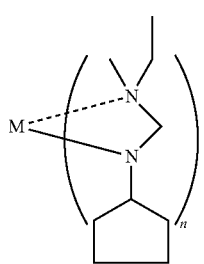
(466) 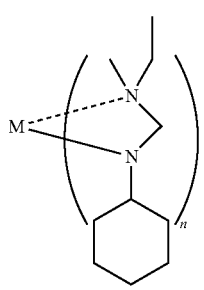
(467) 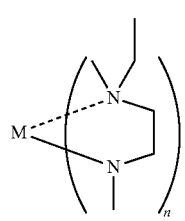
(468) 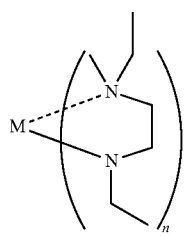
(469) 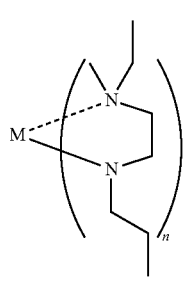
(470) 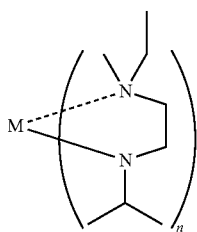
(471) 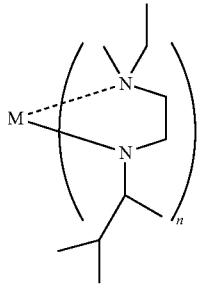
(472) 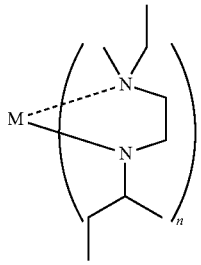
(473) 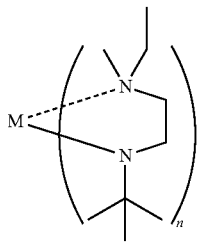
(474) 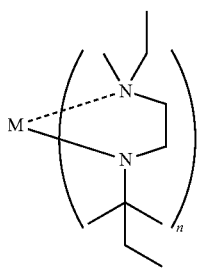
(475) 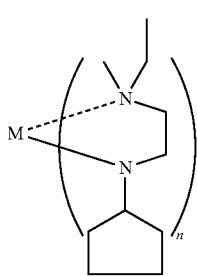

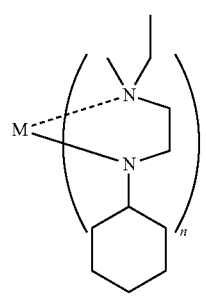
(476)
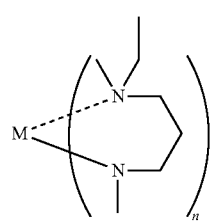
(477)
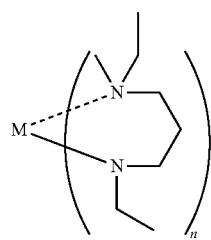
(478)
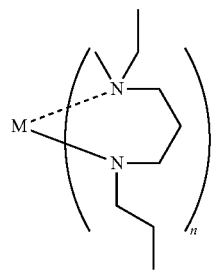
(479)
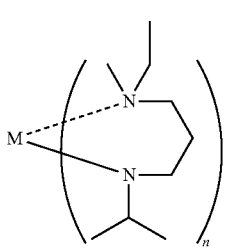
(480)
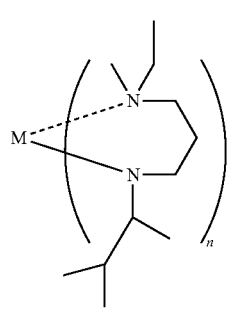
(481)
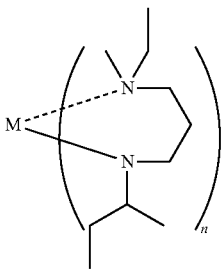
(482)
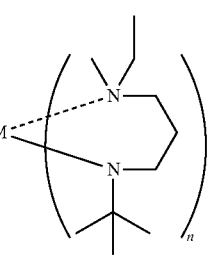
(483)
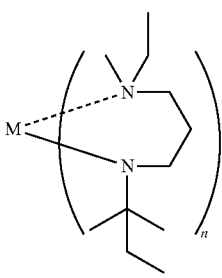
(484)
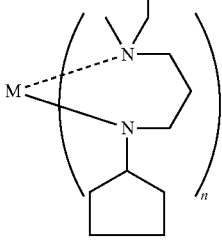
(485)
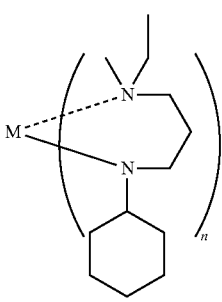
(486)

(487)
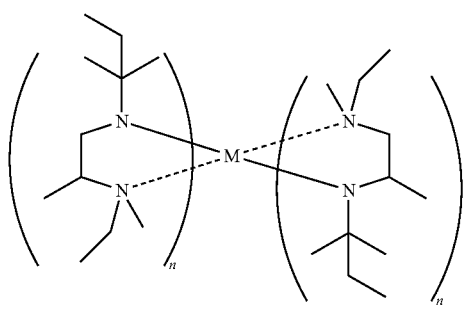
(488)
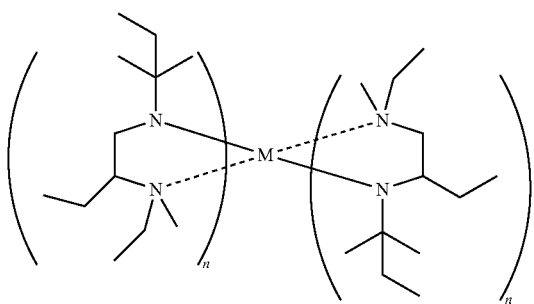
(489)
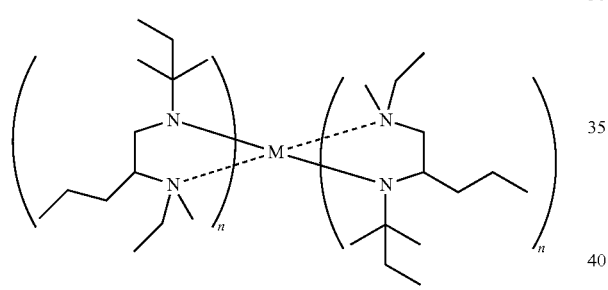
(490)
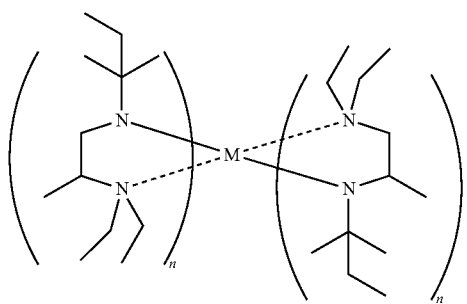
(491)
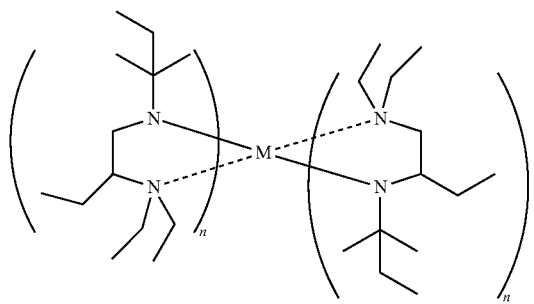
(492)
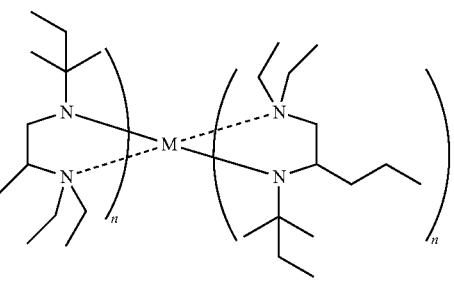
(493)
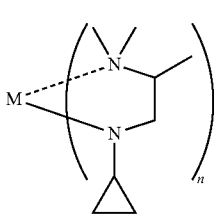
(494)
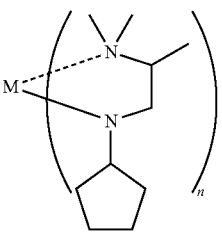
(495)
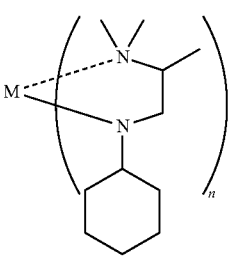
(496)
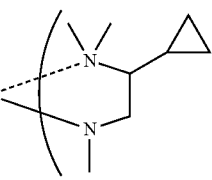
(497)
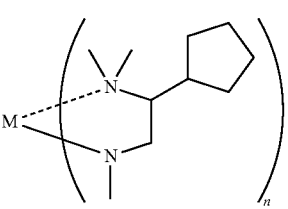

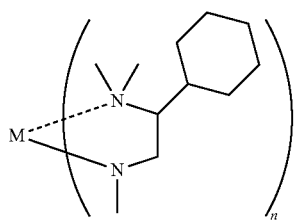
(498)
Specific examples of the bis(amide amino alkane) magnesium compound of the present invention include the compounds represented by the following formulas (4) to (18).
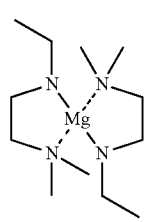
(4)
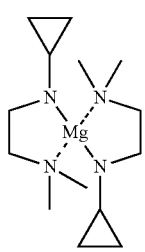
(5)
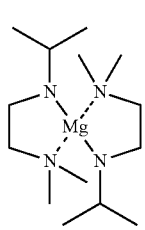
(6)
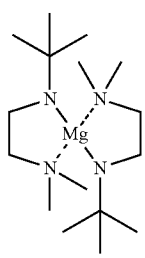
(7)
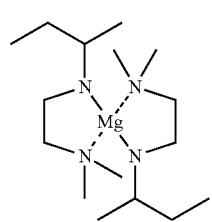
(8)
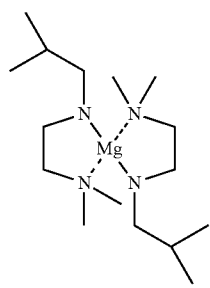
(9)
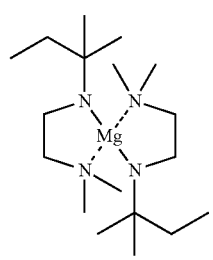
(10)
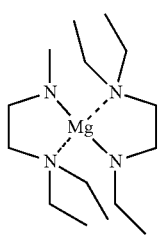
(11)
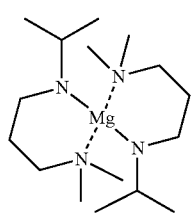
(12)
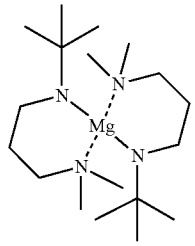
(13)
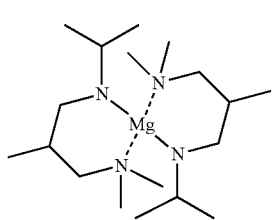
(14)

-continued
(15)
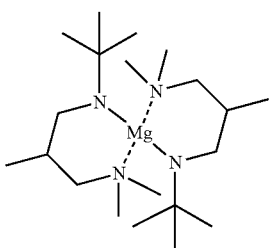
(16)
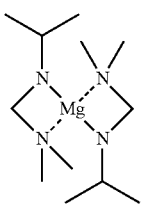
(17)
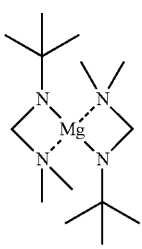
(18)
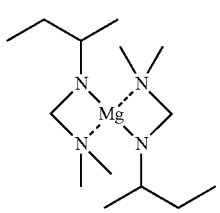
Specific examples of the bis(amide amino alkane) cobalt compound of the present invention include the compounds represented by the following formulas (6) to (20) and (1a) to (1u).
(6)
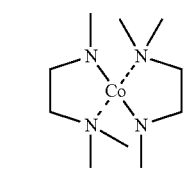
(7)
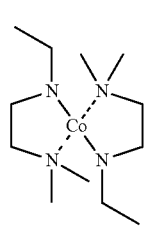
-continued
(8)
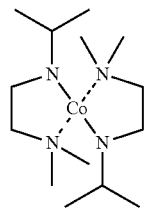
(9)
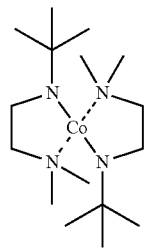
(10)
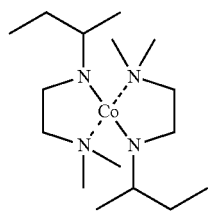
(11)
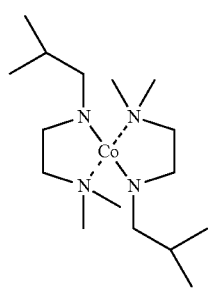
(12)
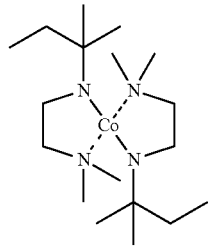
(13)
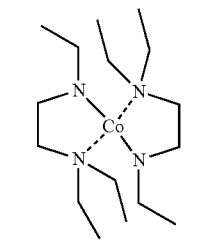

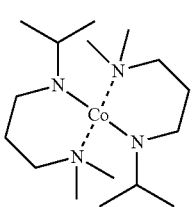
(14)
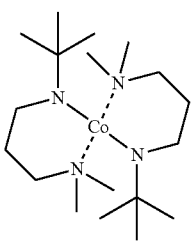
(15)
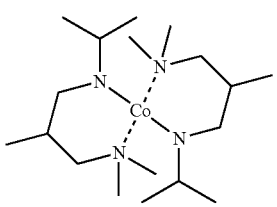
(16)
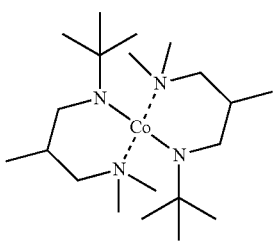
(17)
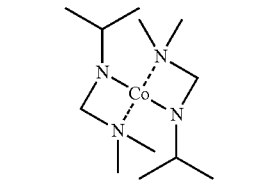
(18)
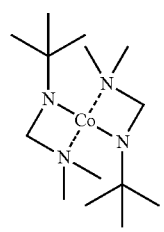
(19)
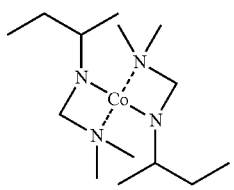
(20)
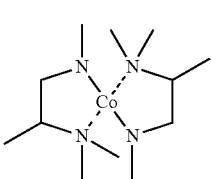
(1a)
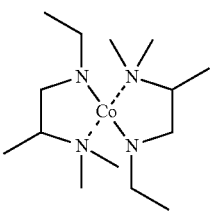
(1b)
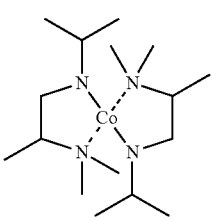
(1c)
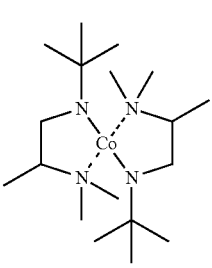
(1d)
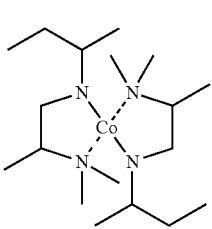
(1e)
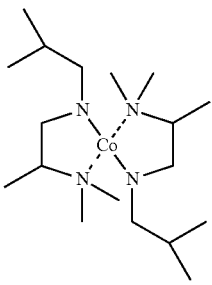
(1f)
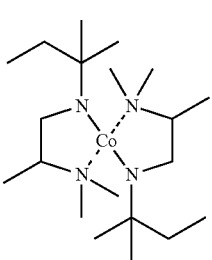
(1g)

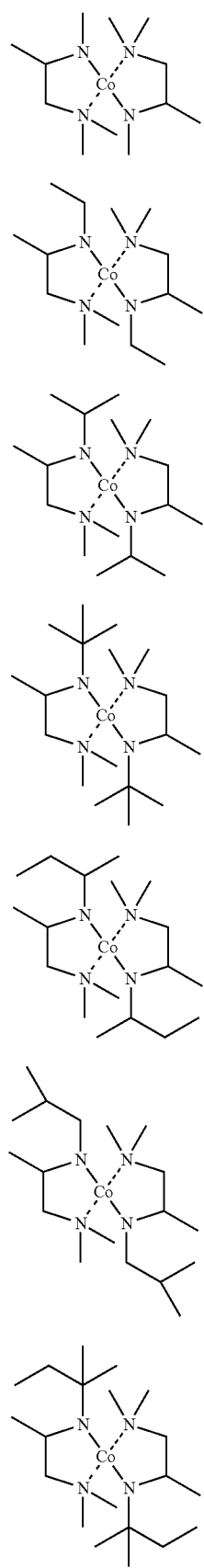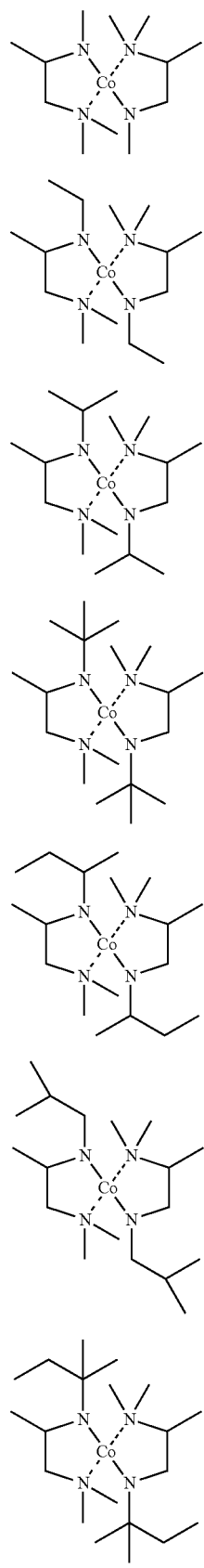

Specific examples of the bis(amide amino alkane) manganese compound of the present invention include the compounds represented by the following formulas (6) to (27).
(6)
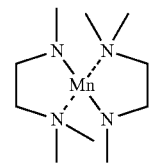
(7)
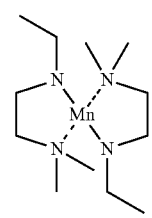
(8)
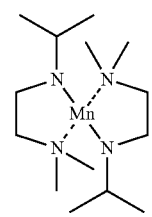
(9)
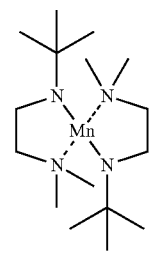
(10)
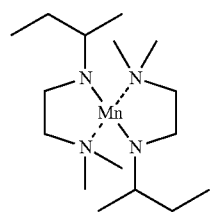
(11)
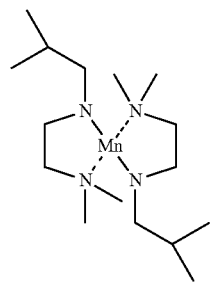
-continued
(12)
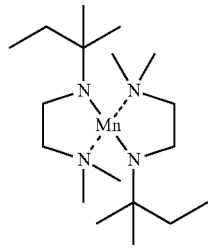
(13)
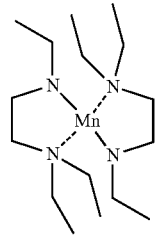
(14)
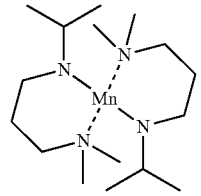
(15)
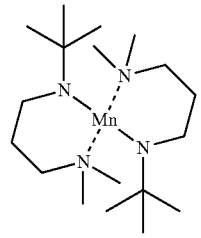
(16)
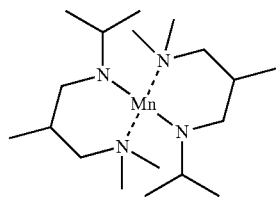
(17)
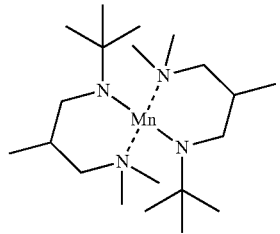
(18)
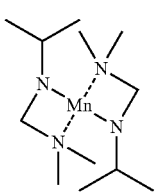

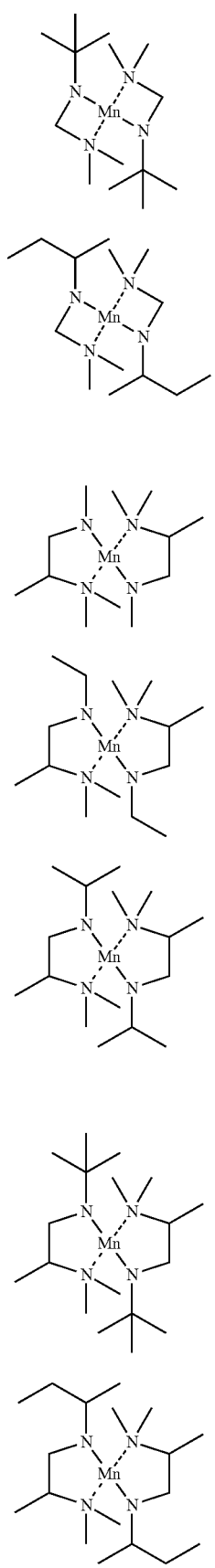

(19)
(20)
(21)
(22)
(23)
(24)
(25)
(26)
(27)

The (amide amino alkane) metal compound of the present invention such as bis(amide amino alkane) magnesium compound and (amide amino alkane) lithium compound, in particular, may be synthesized by a method (hereinafter, sometimes referred to as "Reaction (I) of the present invention") in which an (amide amino alkane) metal compound (1) is synthesized by reacting a mono- or di-alkyl metal compound (2a) or (2b) such as di-alkyl magnesium compound and alkyl lithium compound with a di-amino alkane compound (3) as shown in the following scheme.

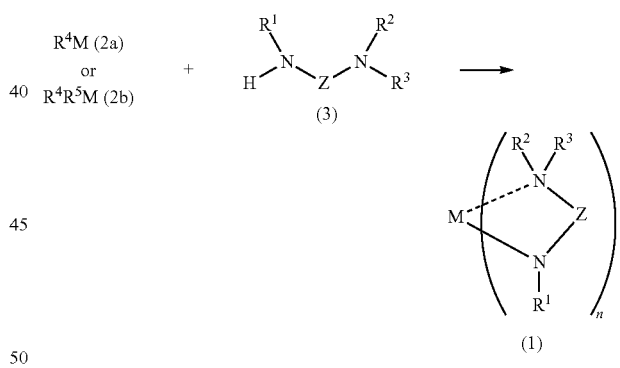

wherein
$R^4$ and $R^5$ may be the same as, or different from each other, and each independently represents a linear or branched alkyl group having 1 to 10 carbon atoms; and
M, $R^1$, $R^2$, $R^3$ and Z are defined as above.

The mono- or di-alkyl metal compound to be used in the Reaction (I) of the present invention is represented by the above formula (2a) or (2b). In the formulas (2a) and (2b), $R^4$ and $R^5$ may be the same as, or different from each other, and each independently represents a linear or branched alkyl group having 1 to 10 carbon atoms such as methyl, ethyl, n-propyl, isopropyl, n-butyl, isobutyl, t-butyl, n-pentyl, t-pentyl, neopentyl and n-decyl.

The mono- or di-alkyl metal compound to be used in the Reaction (I) of the present invention may be a commercially available product, and may be prepared from a metal, simple substance, such as metallic magnesium as a starting material by a known method. A mono- or di-alkyl metal compound represented by the formula (2a) or (2b) in which $R^4$ and $R^5$ are n-butyl or ethyl, including di(n-butyl) magnesium and n-butyl ethyl magnesium, may be suitably used.

The di-amino alkane compound to be used in the Reaction (I) of the present invention is represented by the above formula (3). In the formula (3), $R^1$, $R^2$, $R^3$ and Z correspond to $R^1$, $R^2$, $R^3$ and Z in the formula (1), respectively, and are defined as above.

Accordingly, preferable examples of the di-amino alkane compound to be suitably used in the Reaction (I) of the present invention include 1-isopropylamino-2-dimethylaminoethane, 1-cyclopropylamino-2-dimethylaminoethane, 1-(t-butylamino)-2-dimethylaminoethane, 1-isobutylamino-2-dimethylaminoethane, 1-dimethylamino-2-(t-pentylamino)ethane, 1-isopropylamino-3-dimethylaminopropane, 1-(t-butylamino)-3-dimethylaminopropane, (isopropylamino)(dimethylamino)methane and (t-butylamino)(dimethylamino)methane.

The di-amino alkane compound to be used in the Reaction (I) of the present invention may be a commercially available product, and may be prepared by a combination of known methods. A method in which the compound is prepared by the reduction reaction of hydrochloride of halogenated alkane having mono-alkyl amine and "di-alkyl amino group" in its structure, or the corresponding imine compound, for example, may be preferably employed.

The amount of the di-amino alkane compound to be used may be preferably from 1.5 mole to 3.0 mole, more preferably from 1.8 mole to 2.2 mole, per mole of the mono- or di-alkyl metal compound.

The Reaction (I) of the present invention may be preferably conducted in an organic solvent. The organic solvent to be used is not limited as long as it does not inhibit the reaction. Examples thereof include ethers such as diethyl ether, tetrahydrofuran, dimethoxyethane and dioxane; aliphatic hydrocarbons such as hexane, heptane, octane, cyclohexane, methylcyclohexane and ethylcyclohexane; and aromatic hydrocarbons such as toluene and xylene. An ether, an aliphatic hydrocarbon, or a mixture of an ether and an aliphatic hydrocarbon may be suitably used. These organic solvents may be used alone or in combination of two or more types thereof.

The amount of the organic solvent to be used may be preferably from 1 g to 100 g, more preferably from 1 g to 10 g, per gram (g) of the mono- or di-alkyl metal compound.

The Reaction (I) of the present invention may be conducted, for example, by a method in which the reaction is conducted while mixing and stirring the mono- or di-alkyl metal compound, the di-amino alkane compound and an organic solvent. The reaction temperature may be preferably from −20° C. to 120° C., more preferably from 0° C. to 100° C. There are no particular restrictions to the reaction pressure.

The (amide amino alkane) metal compound, which is the desired product, may be obtained by the Reaction (I) of the present invention. After the completion of the reaction, the synthesized (amide amino alkane) metal compound may be isolated/purified by a known method such as extraction, filtration, concentration, distillation, sublimation, recrystallization and column chromatography.

The (amide amino alkane) metal compound, which is the desired product of the present invention, and the di-alkyl magnesium compound, which is the starting material, are often unstable to moisture and oxygen in the atmosphere. Accordingly, the reaction operation, the post-treatment of the reaction solution, and the like may be preferably conducted under anhydrous conditions or under inert gas atmosphere.

The (amide amino alkane) metal compound of the present invention may be synthesized by reacting a metal with a di-amino alkane compound in the same way as in the above-described process in which the mono- or di-alkyl metal compound is used, except that the metal is used instead of the mono- or di-alkyl metal compound.

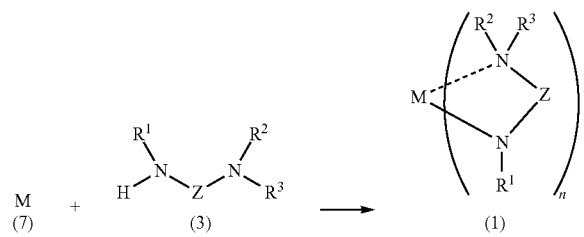

wherein M, $R^1$, $R^2$, $R^3$ and Z are defined as above.

The (amide amino alkane) metal compound of the present invention such as bis(amide amino alkane) cobalt compound, bis(amide amino alkane) manganese compound, bis(amide amino alkane) zinc compound, bis(amide amino alkane) iron compound, bis(amide amino alkane) nickel compound, tris(amide amino alkane) indium compound, tris(amide amino alkane) yttrium compound and tris(amide amino alkane) lanthanum compound, in particular, may be synthesized by a method as shown in the following scheme, and more specifically, a method in which an (amide amino alkane) metal compound (1) is prepared by reacting an alkyl alkali metal compound (4a) or an alkali metal (4b) with a di-amino alkane compound (3) to form an (amide amino alkane) alkali metal compound (5) (hereinafter, sometimes referred to as "Reaction (A)"), and then reacting this compound with a metal halide compound (6) such as di-halogeno cobalt compound and di-halogeno manganese compound (hereinafter, sometimes referred to as "Reaction (B)"). Hereinafter, the combination of the Reaction (A) and the Reaction (B) is sometimes referred to as "Reaction (II) of the present invention".

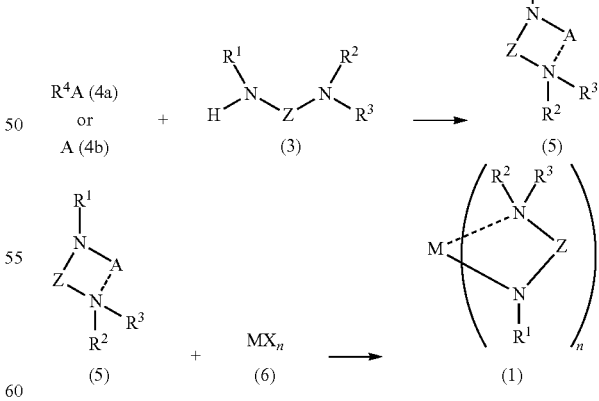

wherein
$R^4$ represents a linear or branched alkyl group having 1 to 10 carbon atoms;
A represents an alkali metal atom;
X represents a halogen atom; and
M, $R^1$, $R^2$, $R^3$ and Z are defined as above.

(Reaction (A): Synthesis of (amide amino alkane) Alkali Metal Compound (5))

The alkyl alkali metal compound to be used in the Reaction (A) of the present invention is represented by the above formula (4a). In the formula (4a), $R^4$ represents a linear or branched alkyl group having 1 to 10 carbon atoms such as methyl, ethyl, n-propyl, isopropyl, n-butyl, isobutyl, t-butyl, n-pentyl, t-pentyl, neopentyl and n-decyl, and A represents an alkali metal such as lithium atom, sodium atom and potassium atom. These alkyl alkali metal compounds may be used alone or in combination of two or more types thereof.

As the alkyl alkali metal compound, lithium methyl or lithium n-butyl may be suitably used.

In addition, an alkali metal (4b) may be used instead of the alkyl alkali metal compound (4a).

The di-amino alkane compound to be used in the Reaction (A) of the present invention is represented by the above formula (3). In the formula (3), $R^1$, $R^2$, $R^3$ and Z correspond to $R^1$, $R^2$, $R^3$ and Z in the formula (1), respectively, and are defined as above.

Accordingly, specific examples of the di-amino alkane compound to be suitably used in the Reaction (A) of the present invention include 1-ethylamino-2-dimethylaminoethane, 1-isopropylamino-2-dimethylaminoethane, 1-(t-butylamino)-2-dimethylaminoethane, 1-isobutylamino-2-dimethylaminoethane, 1-dimethylamino-2-(t-pentylamino)ethane, 1-isopropylamino-3-dimethylaminopropane, 1-(t-butylamino)-3-dimethylaminopropane, (isopropylamino)(dimethylamino)methane, (t-butylamino)(dimethylamino)methane, 1-methylamino-2-dimethylaminopropane, 1-ethylamino-2-dimethylaminopropane, 1-isopropylamino-2-dimethylaminopropane, 1-(t-butylamino)-2-dimethylaminopropane, 1-(s-butylamino)-2-dimethylaminopropane, 1-isobutylamino-2-dimethylaminopropane and 1-(t-pentylamino)-2-dimethylaminopropane.

The di-amino alkane compound to be used in the Reaction (A) of the present invention may be a commercially available product, and may be prepared by a combination of known methods. A method in which the compound is prepared by the reduction reaction of hydrochloride of halogenated alkane having mono-alkyl amine and "di-alkyl amino group" in its structure, or the corresponding imine compound, for example, may be preferably employed.

The amount of the di-amino alkane compound to be used may be preferably from 1.5 mole to 3.0 mole, more preferably from 1.8 mole to 2.2 mole, per mole of the alkyl alkali metal compound or the alkali metal.

The Reaction (A) of the present invention may be preferably conducted in an organic solvent. The organic solvent to be used is not limited as long as it does not inhibit the reaction. Examples thereof include ethers such as diethyl ether, tetrahydrofuran, dimethoxyethane and dioxane; aliphatic hydrocarbons such as hexane, heptane, octane, cyclohexane, methylcyclohexane and ethylcyclohexane; and aromatic hydrocarbons such as toluene and xylene. An ether, an aliphatic hydrocarbon, or a mixture of an ether and an aliphatic hydrocarbon may be suitably used. These organic solvents may be used alone or in combination of two or more types thereof.

The amount of the organic solvent to be used may be preferably from 1 g to 100 g, more preferably from 1 g to 10 g, per gram (g) of the alkyl alkali metal compound or the alkali metal.

The Reaction (A) of the present invention may be conducted, for example, by a method in which the reaction is conducted while stirring a mixture of the di-amino alkane compound and an organic solvent, to which a solution (which may be a suspension) of the alkyl alkali metal compound or alkali metal in an organic solvent is added. The reaction temperature may be preferably from −78° C. to 120° C., more preferably from −20° C. to 60° C. There are no particular restrictions to the reaction pressure.

(Reaction (B): Synthesis of (amide amino alkane) Metal Compound (1))

The metal halide compound to be used in the Reaction (B) of the present invention, including di-halogeno cobalt compound, di-halogeno manganese compound, di-halogeno zinc compound, di-halogeno iron compound, di-halogeno nickel compound, tri-halogeno indium compound, tri-halogeno yttrium compound and tri-halogeno lanthanum compound, is represented by the above formula (6). In the formula (6), X represents a halogen atom such as fluorine atom, chlorine atom, bromine atom and iodine atom.

Preferable examples of the metal halide compound to be suitably used include metal chloride such as cobalt(II) chloride, manganese(II) chloride, zinc(II) chloride, iron(II) chloride, nickel(II) chloride, indium(III) chloride, yttrium(III) chloride and lanthanum(III) chloride; metal bromide such as cobalt(II) bromide, manganese(II) bromide, zinc(II) bromide, iron(II) bromide, nickel(II) bromide, indium(III) bromide, yttrium(III) bromide and lanthanum(III) bromide; and metal iodide such as cobalt(II) iodide, manganese(II) iodide, zinc(II) iodide, iron(II) iodide, nickel(II) iodide, indium(III) iodide, yttrium(III) iodide and lanthanum(III) iodide.

The amount of the metal halide compound to be used may be preferably from 0.25 mole to 0.75 mole, more preferably from 0.4 mole to 0.6 mole, per mole of the (amide amino alkane) alkali metal compound.

The Reaction (B) of the present invention may be preferably conducted in an organic solvent. The organic solvent to be used is not limited as long as it does not inhibit the reaction. Examples thereof include ethers such as diethyl ether, tetrahydrofuran, dimethoxyethane and dioxane; aliphatic hydrocarbons such as hexane, heptane, octane, cyclohexane, methylcyclohexane and ethylcyclohexane; and aromatic hydrocarbons such as toluene and xylene. An ether, an aliphatic hydrocarbon, or a mixture of an ether and an aliphatic hydrocarbon may be suitably used. These organic solvents may be used alone or in combination of two or more types thereof.

The amount of the organic solvent to be used may be preferably from 1 g to 100 g, more preferably from 1 g to 10 g, per gram (g) of the (amide amino alkane) alkali metal compound.

The Reaction (B) of the present invention may be conducted, for example, by a method in which the reaction is conducted while stirring a mixture of the metal halide compound and an organic solvent, to which a solution of the (amide amino alkane) alkali metal compound, which is prepared by the Reaction (A), in an organic solvent is added. The reaction temperature may be preferably from −78° C. to 120° C., more preferably from −20° C. to 60° C. There are no particular restrictions to the reaction pressure.

The (amide amino alkane) metal compound, which is the desired product, may be obtained by the Reaction (B) of the present invention. After the completion of the reaction, the synthesized (amide amino alkane) metal compound may be isolated/purified by a known method such as extraction, filtration, concentration, distillation, sublimation, recrystallization and column chromatography, for example.

The same solvent may be used for conducting the Reactions (A) and (B) of the present invention, for example. The reaction solution obtained by the Reaction (A) may be used for the Reaction (B) without any treatment, or without isolating/purifying the (amide amino alkane) alkali metal compound (5) produced as a result of the Reaction (A), to continuously synthesize the (amide amino alkane) metal compound.

The (amide amino alkane) metal compound, which is the desired product, the alkyl alkali metal compound, which is the starting material, and the (amide amino alkane) alkali metal compound, which is the synthetic intermediate, are often unstable to moisture and oxygen in the atmosphere. Accordingly, the reaction operation, the post-treatment of the reaction solution, and the like may be preferably conducted under anhydrous conditions or under inert gas atmosphere. In addition, the starting material, solvent, and the like may be preferably dehydrated or dried prior to being used.

A metal-containing thin film may be formed with good film-forming performance by a CVD method, for example, using the (amide amino alkane) metal compound of the present invention.

A metal-containing thin film may be vapor-deposited on an object by a known CVD method and atomic layer deposition method (ALD method). A metal-containing thin film may be vapor-deposited on an object, for example, by feeding the vapor of the (amide amino alkane) metal compound onto the heated object under atmospheric or reduced pressure, together with a hydrogen source (a reducing gas such as hydrogen, ammonia, and the like, for example), a nitrogen source (nitrogen, ammonia, and the like, for example) or an oxygen source (for example, an oxidizing gas such as oxygen, ozone, and the like; water; alcohols such as methanol, ethanol, n-propyl alcohol, isopropyl alcohol, n-butyl alcohol, and the like). The gas (including a vaporized liquid) may be diluted with an inert gas, and the like. A metal-containing thin film may be also vapor-deposited by a plasma CVD method in which the similar material is fed.

In the CVD method, the (amide amino alkane) metal compound needs to be vaporized for the formation of thin film. A method of vaporizing the (amide amino alkane) metal compound to be employed in the present invention may be, for example, a method in which the (amide amino alkane) metal compound is filled or fed into a vaporizing chamber, and then vaporized therein, or alternatively, a method (solution method) in which a solution prepared by diluting the (amide amino alkane) metal compound with a suitable solvent (Examples thereof include aliphatic hydrocarbons such as hexane, cyclohexane, methylcyclohexane, ethylcyclohexane, heptane and octane; aromatic hydrocarbons such as toluene, ethyl benzene and xylene; and ethers such as glyme, diglyme, triglyme, dioxane and tetrahydrofuran) is fed into a vaporizing chamber with a liquid feed pump, and then vaporized therein.

As for the vapor-deposition conditions in the case where a metal-containing thin film is vapor-deposited using the (amide amino alkane) metal compound of the present invention, for example, the pressure in the reaction system may be preferably from 1 Pa to 200 kPa, the temperature of the object on which the film is formed may be preferably from 50° C. to 900° C., more preferably from 100° C. to 600° C., and the temperature at which the (amide amino alkane) metal compound is vaporized may be preferably from 0° C. to 250° C., more preferably from 30° C. to 200° C.

When a metal-containing thin film is vapor-deposited, the percentage of an oxygen source (an oxidizing gas, water vapor or alcohol vapor, or a mixture thereof, for example), a nitrogen source (nitrogen gas, ammonia gas, or a mixture thereof, for example) or a reducing gas (hydrogen gas or ammonia gas, or a mixture thereof, for example) to the total amount of the gases may be preferably from 3 vol % to 99 vol %, more preferably from 5 vol % to 98 vol %.

EXAMPLES

The present invention will be more specifically described below with reference to the Examples. However, the scope of the present invention should not be limited to these Examples.

Reference Example A1

Synthesis of dibutyl magnesium

Under argon atmosphere, into a 100 mL-volume flask equipped with a stirrer, a thermometer and a dropping funnel were placed 5.5 g (0.23 mol) of metallic magnesium and 20 ml of diethyl ether. And then, 3.0 g (21 mmol) of bromobutane was slowly dropped into the flask. Subsequently, 180 ml of diethyl ether and 25 g (0.18 mol) of bromobutane were slowly dropped into the flask, and the mixture was reacted while stirring at 40° C. for 2 hours. And then, 55 g (0.62 mol) of dioxane was added to the reaction solution, and the mixture was reacted while stirring at 40° C. for 2 hours. After the completion of the reaction, under argon atmosphere, the reaction solution was filtrated, and the filtrate was concentrated under reduced pressure. The resultant concentrate was heated and dried under vacuum, to provide 22 g of dibutyl magnesium. (Isolation yield: 80%)

Reference Example A2

Synthesis of 1-isopropylamino-2-dimethylaminoethane

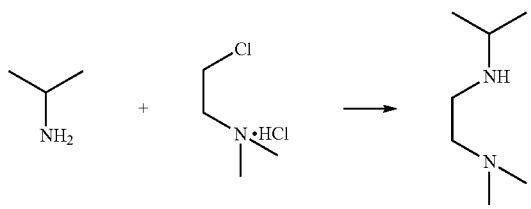

Into a 50 mL-volume flask equipped with a stirrer, a thermometer and a dropping funnel were placed 6.0 g (0.10 mol) of isopropylamine and 5 ml of water. And then, while maintaining the solution temperature within a range of from 30° C. to 50° C., 10 ml of aqueous solution of 5.0 g (35 mmol) of 2-(dimethylamino)ethyl chloride hydrochloride was slowly dropped into the flask, and the mixture was stirred for 2 hours. Subsequently, 10 ml of aqueous solution of 2.8 g (70 mmol) of sodium hydroxide was slowly dropped into the flask in an ice bath, and the mixture was reacted for 10 minutes. After the completion of the reaction, the reaction solution was subjected to extraction with 25 ml of hexane twice, and the hexane layer was concentrated under reduced pressure. The resultant concentrate was distilled under reduced pressure (65° C., 4.0 kPa), to provide 1.4 g of 1-isopropylamino-2-dimethylaminoethane. (Isolation yield: 31%)

Reference Example A3

Synthesis of 1-(t-butylamino)-2-dimethylaminoethane

The reaction was conducted in the same way as in Reference Example A2, except that 7.3 g (0.10 mol) of t-butylamine was used instead of isopropylamine. Then, the reaction solution was concentrated, and the resultant concentrate was distilled under reduced pressure (60° C., 2.4 kPa), to provide 1.8 g of 1-(t-butylamino)-2-dimethylaminoethane. (Isolation yield: 36%)

Reference Example A4

Synthesis of 1-(s-butylamino)-2-dimethylaminoethane

The reaction was conducted in the same way as in Reference Example A2, except that 7.3 g (0.10 mol) of s-butylamine was used instead of isopropylamine. Then, the reaction solution was concentrated, and the resultant concentrate was distilled under reduced pressure (65° C., 2.0 kPa), to provide 1.7 g of 1-(s-butylamino)-2-dimethylaminoethane. (Isolation yield: 34%)

Reference Example A5

Synthesis of (t-butyl)(3-(dimethylamino)propylamine

The reaction was conducted in the same way as in Reference Example A2, except that 5.5 g (35 mmol) of 3-(dimethylamino)propyl chloride hydrochloride was used instead of 5.0 g (35 mmol) of 2-(dimethylamino)ethyl chloride hydrochloride. Then, the reaction solution was concentrated, and the resultant concentrate was distilled under reduced pressure (60° C., 0.80 kPa), to provide 2.2 g of (t-butyl)(3-(dimethylamino)propylamine. (Isolation yield: 40%)

Reference Example A6

Synthesis of 1-(t-butylamino)-2-dimethylaminoethane

Into a 50 mL-volume flask equipped with a stirrer, a thermometer and a dropping funnel were placed 16 g (0.22 mol) of t-butylamine, 5.0 g (35 mmol) of 2-(dimethylamino)ethyl chloride hydrochloride and 1 ml of water. And then, the mixture was reacted at 70° C. for 10 hours. After the completion of the reaction, the reaction solution was subjected to extraction with 25 ml of hexane twice, and the hexane layer was concentrated under reduced pressure. The resultant concentrate was distilled under reduced pressure (60° C., 2.4 kPa), to provide 3.0 g of 1-(t-butylamino)-2-dimethylaminoethane. (Isolation yield: 60%)

Example A1

Synthesis of bis(1-isopropylamide-2-dimethylaminoethane-N,N') magnesium (Magnesium Compound (6)

Under argon atmosphere, into a 25 mL-volume flask equipped with a stirrer, a thermometer and a dropping funnel were placed 0.69 g (5.0 mmol) of dibutyl magnesium prepared in Reference Example A1 and 10 ml of heptane. And then, 1.3 g (10 mmol) of 1-isopropylamino-2-dimethylaminoethane prepared in Reference Example A2 was slowly dropped into the flask, and the mixture was reacted while stirring at 90° C. for 6 hours. After the completion of the reaction, the reaction solution was concentrated, and the resultant concentrate was distilled under reduced pressure (80° C., 13 Pa), to provide 1.3 g of bis(1-isopropylamide-2-dimethylaminoethane-N,N') magnesium as a colorless and transparent liquid. (Isolation yield: 92%) The compound was maintained at 25° C. for several hours, to change into a white solid.

Additionally, bis(1-isopropylamide-2-dimethylaminoethane-N,N') magnesium was a novel compound, which had the following properties:

$^1$H-NMR (tetrahydrofuran-$d_8$, δ (ppm)); 2.99 (4H, t, 5.8 Hz), 2.85 (2H, sept, 6.3 Hz), 2.61 (4H, t, 5.8 Hz), 2.35 (12H, s), 1.01 (12H, d, 6.3 Hz)

Melting point; 53-55° C.

Example A2

Synthesis of bis(1-(t-butylamide)-2-dimethylaminoethane-N,N') magnesium (Magnesium Compound (7)

The reaction was conducted in the same way as in Example A1, except that 1.4 g (10 mmol) of 1-(t-butylamino)-2-dimethylaminoethane prepared in Reference Example A3 was used instead of 1-isopropylamino-2-dimethylaminoethane. Then, the reaction solution was concentrated, and the resultant concentrate was sublimed under reduced pressure (90° C., 13 Pa), to provide 1.2 g of bis(1-(t-butylamide)-2-dimethylaminoethane-N,N') magnesium as a white solid. (Isolation yield: 77%)

Additionally, bis(1-(t-butylamide)-2-dimethylaminoethane-N,N') magnesium was a novel compound, which had the following properties:

$^1$H-NMR (tetrahydrofuran-$d_8$, δ (ppm)); 3.00 (4H, t, 5.8 Hz), 2.58 (4H, t, 5.8 Hz), 2.34 (12H, s), 1.08 (18H, s)

Melting point; 90-93° C.

Example A3

Synthesis of bis(1-(s-butylamide)-2-dimethylaminoethane-N,N') magnesium (Magnesium Compound (8)

The reaction was conducted in the same way as in Example A1, except that 1.4 g (10 mmol) of 1-(s-butylamino)-2-dimethylaminoethane prepared in Reference Example A4 was used instead of 1-isopropylamino-2-dimethylaminoethane. Then, the reaction solution was concentrated, and the resultant concentrate was distilled under reduced pressure (90° C., 13 Pa), to provide 1.4 g of bis(1-(s-butylamide)-2-dimethylaminoethane-N,N') magnesium as a colorless and transparent liquid. (Isolation yield: 90%)

Additionally, bis(1-(s-butylamide)-2-dimethylaminoethane-N,N') magnesium was a novel compound, which had the following properties:

$^1$H-NMR (tetrahydrofuran-$d_8$, δ (ppm)); 2.98 (6H, m), 2.60 (4H, m), 2.35 (12H, s), 1.53 (2H, m), 1.16 (2H, m), 1.00 (6H, m), 0.85 (6H, m)

Example A4

Synthesis of bis(1-ethylamide-2-dimethylaminoethane-N,N') magnesium (Magnesium Compound (4)

The reaction was conducted in the same way as in Example A1, except that 1.2 g (10 mmol) of 1-ethylamino-2-dimethylaminoethane (commercially available product) was used instead of 1-isopropylamino-2-dimethylaminoethane. Then, the reaction solution was concentrated, and the resultant concentrate was distilled under reduced pressure (110° C., 13 Pa), to provide 0.90 g of bis(1-ethylamide-2-dimethylaminoethane-N,N') magnesium as a colorless and transparent liquid. (Isolation yield: 71%)

Additionally, bis(1-ethylamide-2-dimethylaminoethane-N,N') magnesium was a novel compound, which had the following properties:

$^1$H-NMR (tetrahydrofuran-$d_8$, δ (ppm)); 2.93 (4H, br), 2.90 (4H, br), 2.63 (4H, br), 2.15 (12H, br), 1.00 (6H, br)

Example A5

Synthesis of bis(1-ethylamide-2-diethylaminoethane-N,N') magnesium (Magnesium Compound (11)

The reaction was conducted in the same way as in Example A1, except that 1.4 g (10 mmol) of 1-ethylamino-2-diethylaminoethane (commercially available product) was used instead of 1-isopropylamino-2-dimethylaminoethane. Then, the reaction solution was concentrated, and the resultant concentrate was distilled under reduced pressure (130° C., 13 Pa), to provide 1.0 g of bis(1-ethylamide-2-diethylaminoethane-N,N') magnesium as a colorless and transparent liquid. (Isolation yield: 60%)

Additionally, bis(1-ethylamide-2-diethylaminoethane-N,N') magnesium was a novel compound, which had the following properties:

$^1$H-NMR (tetrahydrofuran-$d_8$, δ (ppm)); 2.97 (4H, br), 2.78 (8H, br), 2.45 (8H, br), 1.10 (6H, br), 0.96 (12H, br)

Example A6

Synthesis of bis(1-(t-butylamide)-3-dimethylaminopropane-N,N') magnesium (Magnesium Compound (13)

The reaction was conducted in the same way as in Example A1, except that 1.6 g (10 mmol) of (t-butyl)(3-(dimethylamino)propylamine prepared in Reference Example A5 was used instead of 1-isopropylamino-2-dimethylaminoethane. Then, the reaction solution was concentrated, and the resultant concentrate was distilled under reduced pressure (90° C., 13 Pa), to provide 1.4 g of bis(1-(t-butylamide)-3-dimethylaminopropane-N,N') magnesium as a colorless and transparent liquid. (Isolation yield: 76%)

Additionally, bis(1-(t-butylamide)-3-dimethylaminopropane-N,N') magnesium was a novel compound, which had the following properties:

$^1$H-NMR (tetrahydrofuran-$d_8$, δ (ppm)); 3.04 (4H, t, 5.8 Hz), 2.51 (4H, t, 5.8 Hz), 2.39 (12H, s), 1.60 (4H, m), 1.10 (18H, s)

Melting point; 110-114° C.

Example A7

Vapor-deposition Test; Formation of Magnesium-containing Thin Film

The vapor-deposition tests were conducted by the CVD method, using bis(1-isopropylamide-2-dimethylaminoethane-N,N')magnesium (magnesium compound (6)) obtained in Example A1, to evaluate the film-forming performance.

The apparatus shown in FIG. 1 was used to conduct the vapor-deposition tests. The apparatus shown in FIG. 1 has the following construction. The magnesium compound in a container for magnesium raw material (vaporizer) 7, which is maintained at a constant temperature by means of a thermostatic bath 8, is heated and vaporized, and discharged from the container for raw material 7, together with a helium gas which is fed via a mass flow controller 4. The gas discharged from the container for raw material 7 is fed into a reactor 9, together with a helium gas which is fed via a mass flow controller 5. Meanwhile, an oxygen gas, which is a reactive gas, is fed into the reactor 9 via a mass flow controller 6. The pressure in the reaction system is monitored by a pressure gauge 12, and is controlled to a predetermined pressure by opening and closing a valve, which is provided upstream of a vacuum pump 14. The central part of the reactor 9 can be heated by a heater 11. The magnesium compound, which is fed into the reactor 9, is oxidized and thermally-decomposed on a surface of a substrate 10 which is placed in the central part of the reactor and heated to a predetermined temperature by the heater 11, to form a magnesium-containing thin film on the substrate 10. The gas discharged from the reactor 9 is exhausted to the atmosphere via a trap 13 and the vacuum pump 14.

The vapor-deposition conditions and the film properties were as follows.

(Vapor-deposition Conditions)
Magnesium raw material; bis(1-isopropylamide-2-dimethylaminoethane-N,N')magnesium (magnesium compound (6))
Vaporization temperature; 40° C.
He carrier gas flow rate; 100 sccm
Oxygen gas flow rate; 10 sccm
Substrate material; $SiO_2$/Si
Substrate temperature; 300° C.
Pressure in the reaction system; 1.33 kPa
Vapor-deposition time; 30 min.
(Film Properties (XPS-Depth Measurement))
Film thickness; 50 nm or more
XPS analysis; magnesium oxide film
Carbon content; Not detected
Nitrogen content; Not detected Comparative Example A1

(Vapor-deposition Test; Formation of Magnesium-Containing Thin Film)

The vapor-deposition tests were conducted by the CVD method in the same way as in Example A7, using bis(cyclopentadienyl)magnesium, to evaluate the film-forming performance. The vapor-deposition conditions and the film properties were as follows. The vapor-deposition tests were conducted under the conditions where the amount of the raw material fed was equal to the amount of the raw material fed in Example A7 by adjusting the various conditions.

(Vapor-deposition Conditions)
Magnesium raw material; bis(cyclopentadienyl)magnesium
Vaporization temperature; 30° C.
He carrier gas flow rate; 10 sccm
Diluting He gas flow rate; 90 sccm
Oxygen gas flow rate; 10 sccm
Substrate material; $SiO_2$/Si
Substrate temperature; 300° C.
Pressure in the reaction system; 10 Torr (about 1.33 kPa)
Vapor-deposition time; 30 min.
(Film Properties (XPS-Depth Measurement))
Film thickness; 50 nm or more
XPS analysis; magnesium oxide film
Carbon content; 30% (in terms of carbon atom)
Nitrogen content; Not detected (the raw material does not contain a nitrogen atom at all.)

The results revealed that a high-quality magnesium-containing thin film (magnesium oxide film), which does not contain impurities such as carbon atom and nitrogen atom, might be formed using the bis(amide amino alkane) magnesium compound of the present invention.

Reference Example B1

Synthesis of (1-isopropylamide-2-dimethylaminoethane-N,N') lithium

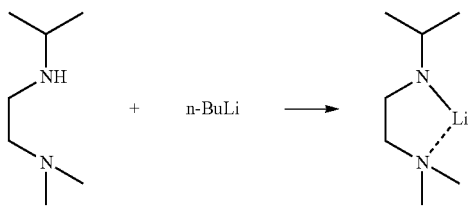

Under argon atmosphere, into a 50 mL-volume flask equipped with a stirrer, a thermometer and a dropping funnel were placed 2.15 g (16.5 mmol) of 1-isopropylamino-2-dimethylaminoethane and 15 ml of hexane. And then, while maintaining the solution temperature at 0° C., 10 ml (16.5 mmol) of 1.65 mol/l n-butyl lithium/hexane solution was slowly dropped into the flask, and the mixture was reacted while stirring at the same temperature for 30 minutes and at 20° C. for 2 hours. After the completion of the reaction, the reaction solution was concentrated under reduced pressure. The resultant concentrate was dried under vacuum, to provide 2.13 g of (1-isopropylamide-2-dimethylaminoethane-N,N') lithium. (Isolation yield: 95%)

Additionally, (1-isopropylamide-2-dimethylaminoethane-N,N') lithium had the following properties:
$^1$H-NMR (tetrahydrofuran-$d_8$, δ (ppm)); 2.95 (2H, t, 6.0 Hz), 2.91 (1H, quint, 6.2 Hz), 2.44 (2H, t, 6.0 Hz), 2.18 (6H, s), 0.99 (6H, d, 6.2 Hz)

Example B1

Synthesis of bis(1-isopropylamide-2-dimethylaminoethane-N,N') cobalt(II) (Cobalt Compound (8)

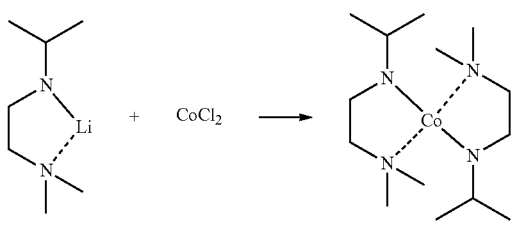

Under argon atmosphere, into a 50 mL-volume flask equipped with a stirrer, a thermometer and a dropping funnel were placed 0.500 g (3.85 mmol) of cobalt(II) chloride (pre-dried anhydride) and 10 ml of tetrahydrofuran. And then, these were mixed and the mixture was stirred for 2 hours. Subsequently, while maintaining the solution temperature at 0° C., 10 ml of solution of 1.05 g (7.71 mmol) of 1-isopropylamide-2-dimethylaminoethane-N,N') lithium, which was prepared in the same way as in Reference Example B1, in tetrahydrofuran was slowly dropped into the flask. And then, the mixture was reacted while stirring at 20° C. for 6 hours. After the completion of the reaction, the reaction solution was concentrated under reduced pressure. To the resultant concentrate was added 50 ml of hexane. And then, the mixture was stirred. The mixture was filtrated, and the filtrate was concentrated under reduced pressure. And then, the resultant concentrate was distilled under reduced pressure (80° C., 13.3 Pa), to provide 1.0 g of (bis(1-isopropylamide-2-dimethylaminoethane-N,N') cobalt(II) as a dark green solid. (Isolation yield: 80%)

Additionally, bis(1-isopropylamide-2-dimethylaminoethane-N,N') cobalt(II) was a novel compound, which had the following properties:
Melting point; 68-69° C.
Cobalt content determined by inductively coupled plasma (ICP) analysis; 19.2 wt % (calculated value; 18.6 wt %)

Reference Example B2

Synthesis of (1-s-butylamide-2-dimethylaminoethane-N,N')lithium

Under argon atmosphere, into a 50 mL-volume flask equipped with a stirrer, a thermometer and a dropping funnel were placed 2.59 g (16.5 mmol) of 1-s-butylamino-2-dimethylaminoethane prepared in Reference Example A4 and 15 ml of hexane. And then, while maintaining the mixture solution at 0° C., 10 ml (16.5 mmol) of 1.65 mold n-butyl lithium/hexane solution was slowly dropped into the flask. After the dropping, the mixture solution was stirred at 0° C. for 30 minutes, and then the mixture was reacted while stirring at 20° C. for 2 hours. After the completion of the reaction, the reaction solution was concentrated under reduced pressure. The resultant concentrate was dried under vacuum, to provide 1-s-butylamide-2-dimethylaminoethane-N,N') lithium. Additionally, 1-s-butylamide-2-dimethylaminoethane-N,N') lithium was used for the subsequent reaction without any purification.

Reference Example B3

Synthesis of (1-t-pentylamino-2-dimethylaminoethane)

Into a 300 mL-volume flask equipped with a stirrer and a thermometer were placed 20.6 g (143 mmol) of 2-(dimethylamino)ethane chloride hydrochloride and 74.0 g (859 mmol) of t-pentylamine. And then, the mixture was heated to reflux for 8 hours. After the completion of the reaction, the reaction mixture was filtrated and washed with 100 ml of hexane twice, and the hexane layer was concentrated under reduced pressure. The resultant concentrate was distilled under reduced pressure (120° C., 11.0 kPa), to provide 13.5 g of 1-t-pentylamino-2-dimethylaminoethane. (Isolation yield: 60%)

Example B2

Synthesis of bis(1-s-butylamide-2-dimethylaminoethane-N,N')cobalt (Cobalt Compound (10)

Under argon atmosphere, into a 100 mL-volume flask equipped with a stirrer, a thermometer and a dropping funnel were placed 1.07 g (8.25 mmol) of anhydrous cobalt(II) chloride and 20 ml of tetrahydrofuran. And then, the mixture was stirred for 2 hours. Subsequently, while maintaining the solution temperature at 0° C., 20 ml of solution of 1-s-butylamide-2-dimethylaminoethane-N,N') lithium, which was prepared in Reference Example B2, in tetrahydrofuran was slowly dropped into the flask. And then, the mixture was reacted while stirring at 20° C. for 6 hours. After the completion of the reaction, the reaction solution was concentrated under reduced pressure. To the resultant concentrate was added 100 ml of hexane. And then, the mixture was stirred. The mixture was filtrated, and the filtrate was concentrated under reduced pressure. And then, the resultant concentrate was distilled under reduced pressure (90° C., 13.3 Pa), to provide 0.8 g of (bis(1-s-butylamide-2-dimethylaminoethane-N,N')cobalt as a dark green liquid. (Isolation yield: 27%)

Additionally, bis(1-s-butylamide-2-dimethylaminoethane-N,N') cobalt was a novel compound, which had the following properties:
Co content determined by ICP analysis; 16.03 wt % (calculated value; 17.06 wt %)

Reference Example B4

Synthesis of (1-t-pentylamide-2-dimethylaminoethane-N,N') lithium

Under argon atmosphere, into a 50 mL-volume flask equipped with a stirrer, a thermometer and a dropping funnel were placed 2.69 g (16.5 mmol) of 1-t-pentylamino-2-dimethylaminoethane prepared in Reference Example B3 and 15 ml of hexane. And then, while maintaining the mixture solution at 0° C., 10 ml (16.5 mmol) of 1.65 mol/l n-butyl lithium/hexane solution was slowly dropped into the flask. After the dropping, the mixture solution was stirred at 0° C. for 30 minutes, and then the mixture was reacted while stirring at 20° C. for 2 hours. After the completion of the reaction, the reaction solution was concentrated under reduced pressure. The resultant concentrate was dried under vacuum, to provide 1-t-pentylamide-2-dimethylaminoethane-N,N' lithium. Additionally, 1-t-pentylamide-2-dimethylaminoethane-N,N' lithium was used for the subsequent reaction without any purification.

Example B3

Synthesis of bis(1-t-pentylamide-2-dimethylaminoethane-N,N') cobalt (Cobalt Compound (12))

Under argon atmosphere, into a 100 mL-volume flask equipped with a stirrer, a thermometer and a dropping funnel were placed 1.07 g (8.25 mmol) of anhydrous cobalt(II) chloride and 20 ml of tetrahydrofuran. And then, the mixture was stirred for 2 hours. Subsequently, while maintaining the solution temperature at 0° C., 20 ml of solution of 1-t-pentylamide-2-dimethylaminoethane-N,N') lithium, which was prepared in Reference Example B4, in tetrahydrofuran was slowly dropped into the flask. And then, the mixture was reacted while stirring at 20° C. for 6 hours. After the completion of the reaction, the reaction solution was concentrated under reduced pressure. To the resultant concentrate was added 100 ml of hexane. And then, the mixture was stirred. The mixture was filtrated, and the filtrate was concentrated under reduced pressure. And then, the resultant concentrate was distilled under reduced pressure (100° C., 13.3 Pa), to provide 1.45 g of (bis(1-t-pentylamide-2-dimethylaminoethane-N,N')cobalt as a dark green liquid. (Isolation yield: 47%)

Additionally, bis(1-t-pentylamide-2-dimethylaminoethane-N,N') cobalt was a novel compound, which had the following properties:
Co content determined by ICP analysis; 15.80 wt % (calculated value; 15.80 wt %)

Example B4

Synthesis of bis(1-t-butylamide-2-dimethylaminoethane-N,N')cobalt (Cobalt Compound (9))

Under argon atmosphere, into a 100 mL-volume flask equipped with a stirrer, a thermometer and a dropping funnel were placed 1.07 g (8.25 mmol) of anhydrous cobalt(II) chloride and 20 ml of tetrahydrofuran. And then, the mixture was stirred for 2 hours. Subsequently, while maintaining the solution temperature at 0° C., 20 ml of solution of 1-t-butylamide-2-dimethylaminoethane-N,N') lithium, which was prepared in Reference Example D3, in tetrahydrofuran was slowly dropped into the flask. And then, the mixture was reacted while stirring at 20° C. for 6 hours. After the completion of the reaction, the reaction solution was concentrated under reduced pressure. To the resultant concentrate was added 100 ml of hexane. And then, the mixture was stirred. The mixture was filtrated, and the filtrate was concentrated under reduced pressure. And then, the resultant concentrate was distilled under reduced pressure (95° C., 13.3 Pa), to provide 1.2 g of (bis(1-t-butylamide-2-dimethylaminoethane-N,N') cobalt as a dark green solid. (Isolation yield: 42%)

Additionally, bis(1-t-butylamide-2-dimethylaminoethane-N,N') cobalt was a novel compound, which had the following properties:
Co content determined by ICP analysis; 16.5 wt % (calculated value; 17.1 wt %)

Example B5

Vapor-deposition Test; Formation of Cobalt-containing Thin Film

The vapor-deposition tests were conducted by the CVD method, using bis(1-isopropylamide-2-dimethylaminoethane-N,N')cobalt(II) (cobalt compound (8)) obtained in Example B1, to evaluate the film-forming performance.

Figure 2:
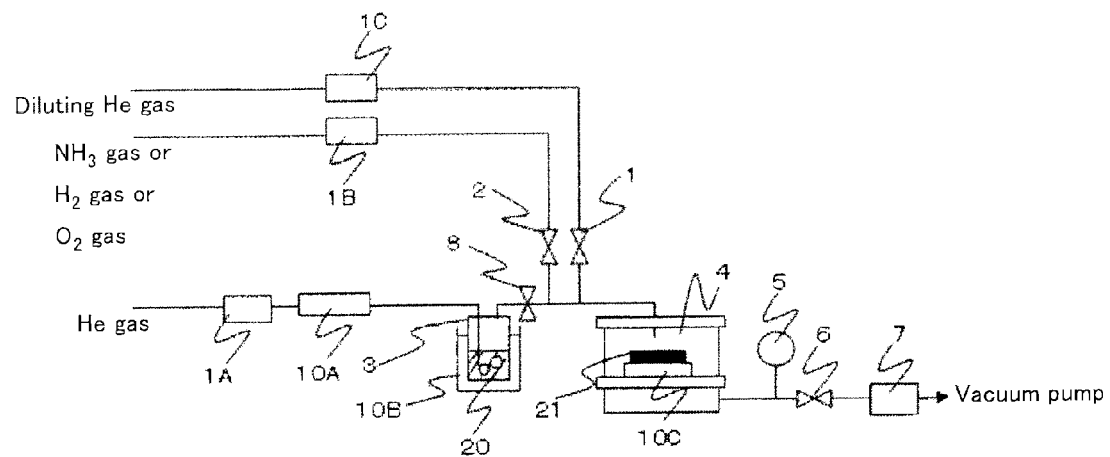
FIG. 2 is a diagram illustrating the construction of the vapor deposition apparatus, which was used in "Examples" for the formation of metal-containing thin film using the (amide amino alkane) metal compound of the present invention, except bis(amide amino alkane) magnesium compound.

The apparatus shown in FIG. 2 was used to conduct the evaluation tests. The cobalt compound 20 in a vaporizer (glass ampule) 3 is heated by means of a heater 10B and vaporized, and discharged from the vaporizer 3, together with a helium gas which is fed via a mass flow controller 1A after pre-heating by a pre-heater 10A. The gas discharged from the vaporizer 3 is fed into a reactor 4, together with a reactive gas such as an ammonia gas or a hydrogen gas and an oxygen gas, which is fed via a mass flow controller 1B and a stop valve 2. The pressure in the reaction system is controlled to a predetermined pressure by opening and closing a valve 6, which is provided upstream of a vacuum pump, and is monitored by a pressure gauge 5. The central part of the reactor can be heated by a heater 10C. The cobalt compound, which is fed into the reactor, is reduced, or oxidized and thermally-decomposed on a surface of a substrate 21 which is placed in the central part of the reactor and heated to a predetermined temperature by the heater 10C, to deposit a cobalt-containing thin film on the substrate 21. The gas discharged from the reactor 4 is exhausted to the atmosphere via a trap 7 and the vacuum pump.

The vapor-deposition conditions and the film properties were as follows. The rectangular substrate of 6 mm×20 mm was used as the substrate on which the film was vapor-deposited.

(Vapor-deposition Conditions)
Cobalt raw material; bis(1-isopropylamide-2-dimethylaminoethane-N,N') cobalt(II) (cobalt compound (8))
Vaporization temperature; 90° C.
He carrier gas flow rate; 10 sccm
Ammonia gas flow rate; 10 sccm
Substrate material; $SiO_2$/Si wafer
Substrate temperature; 200° C.
Pressure in the reaction system; 0.67 kPa
Vapor-deposition time; 5 min.
(Film Properties (SEM and XPS-Depth Measurement))
Film thickness; 400 nm
XPS analysis; cobalt film
Carbon content; Not detected
Nitrogen content; Not detected Example B6

Vapor-deposition Test; Formation of Cobalt-containing Thin Film

The vapor-deposition tests were conducted by the CVD method in the same way as in Example B5, using bis(1-s-butylamide-2-dimethylaminoethane-N,N') cobalt(II) (cobalt compound (10)) obtained in Example B2, to evaluate the film-forming performance. The vapor-deposition conditions and the film properties were as follows.

(Vapor-deposition Conditions)
Cobalt raw material; bis(1-s-butylamide-2-dimethylaminoethane-N,N') cobalt (cobalt compound (10))
Vaporization temperature; 80° C.
He carrier gas flow rate; 30 sccm
Ammonia gas flow rate; 20 sccm
Substrate material; $SiO_2$/Si wafer
Substrate temperature; 200° C.
Pressure in the reaction system; 0.67 kPa
Vapor-deposition time; 5 min.
(Film Properties (SEM and XPS-Depth Measurement))
Film thickness; 200 nm
XPS analysis; cobalt film
Carbon content; Not detected
Nitrogen content; Not detected Comparative Example B1

(Vapor-deposition Test; Formation of Cobalt-containing Thin Film)
The vapor-deposition tests were conducted by the CVD method in the same way as in Example B5, using bis(N-t-butyl-N'-ethylpropionamidinato) cobalt (the compound disclosed in Patent Document 8), to evaluate the film-forming performance. The vapor-deposition conditions and the film properties were as follows.

(Vapor-deposition Conditions)
Vaporization temperature; 90° C.
He carrier gas flow rate; 10 sccm
Ammonia gas flow rate; 10 sccm
Substrate material; $SiO_2$/Si wafer
Substrate temperature; 200° C.
Pressure in the reaction system; 0.67 kPa
Vapor-deposition time; 5 min.
(Film Properties (SEM and XPS-Depth Measurement))
Film thickness; 40 nm
XPS analysis; cobalt film
Carbon content; 3% (in terms of carbon atom)
Nitrogen content; 7% (in terms of nitrogen atom)

The results revealed that the bis(amide amino alkane) cobalt compound of the present invention might be a material from which a cobalt-containing thin film might be formed in a short time (high film-forming rate), and from which a high-quality cobalt-containing thin film, which does not contain impurities such as carbon atom and nitrogen atom, might be formed.

Reference Example C1

Synthesis of a Mixture of
1-isopropylamino-2-dimethylaminopropane and
2-isopropylamino-1-dimethylaminopropane Into a 300 mL-volume flask equipped with a stirrer and a thermometer were placed 25.0 g (158 mmol) of 2-(dimethylamino)propane chloride hydrochloride, 56.1 g (949 mmol) of isopropylamine and 3 ml of water. And then, the mixture was reacted while stirring at 40-50° C. for 10 hours. After the completion of the reaction, the reaction mixture was filtrated and washed with 200 ml of hexane, and the hexane layer was concentrated under reduced pressure. The resultant concentrate was distilled under reduced pressure (105° C., 13.3 kPa), to provide 18.2 g of a mixture of 1-isopropylamino-2-dimethylaminopropane and 2-isopropylamino-1-dimethylaminopropane (mixture ratio 8:2). (Isolation yield: 82%)

Additionally, the mixture of 1-isopropylamino-2-dimethylaminopropane and 2-isopropylamino-1-dimethylaminopropane had the following properties:

$^1$H-NMR (CDCl$_3$, δ (ppm)); 0.89 (3H, s, for major isomer), 0.97 (3H, s, for minor isomer), 1.05, 1.07 (each 3H, each d, J=6.3 Hz, for major isomer), 1.05, 1.10 (each 3H, each d, J=6.3 Hz, for minor isomer), 1.52 (1H, drs), 2.19 (6H, s, for minor isomer), 2.20 (6H, s, for major isomer), 2.48 (2H, d, J=6.8 Hz, for major isomer), 2.50 (2H, d, J=6.8 Hz, for minor isomer), 2.68-2.89 (2H, m)

Reference Example C2

Synthesis of a Mixture of 1-isopropylamide-2-dimethylaminoethane-N,N') lithium and 2-isopropylamide-1-dimethylaminoethane-N,N')lithium Under argon atmosphere, into a 50 mL-volume flask equipped with a stirrer, a thermometer and a dropping funnel were placed 2.15 g (16.5 mmol) of the mixture of 1-isopropylamino-2-dimethylaminopropane and 2-isopropylamino-1-dimethylaminopropane (mixture ratio 8:2) prepared in Reference Example C1, and 15 ml of hexane. And then, while maintaining the mixture solution at 0° C., 10 ml (16.5 mmol) of 1.65 mol/l n-butyl lithium/hexane solution was slowly dropped into the flask. After the dropping, the mixture solution was stirred at 0° C. for 30 minutes, and then the mixture was reacted while stirring at 20° C. for 2 hours. After the completion of the reaction, the reaction solution was concentrated under reduced pressure. The resultant concentrate was dried under vacuum, to provide a mixture of 1-isopropylamide-2-dimethylaminoethane-N,N') lithium and 2-isopropylamide-1-dimethylaminoethane-N,N')lithium.

Additionally, the mixture of 1-isopropylamide-2-dimethylaminoethane-N,N') lithium and 2-isopropylamide-1-dimethylaminoethane-N,N')lithium was used for the subsequent reaction without any treatment.

Example C1

Synthesis of a Mixture of bis(1-isopropylamide-2-dimethylaminopropane-N,N')cobalt (Cobalt Compound (1c)), bis(2-isopropylamide-1-dimethylaminopropane-N,N')cobalt (Cobalt Compound (1j)) and (1-isopropylamide-2-dimethylaminopropane-N,N')(2-isopropylamide-1-dimethylaminopropane-N,N')cobalt (Cobalt Compound (1q)

Under argon atmosphere, into a 100 mL-volume flask equipped with a stirrer, a thermometer and a dropping funnel were placed 1.07 g (8.25 mmol) of anhydrous cobalt(II) chloride and 20 ml of tetrahydrofuran. And then, the mixture was stirred for 2 hours. Subsequently, while maintaining the solution temperature at 0° C., 20 ml of solution of the mixture of 1-isopropylamide-2-dimethylaminoethane-N,N') lithium and 2-isopropylamide-1-dimethylaminoethane-N,N') lithium, which was prepared in Reference Example C2, in tetrahydrofuran was slowly dropped into the flask. And then, the mixture was reacted while stirring at 20° C. for 6 hours. After the completion of the reaction, the reaction solution was concentrated under reduced pressure. To the resultant concentrate was added 100 ml of hexane. And then, the mixture was stirred. The mixture was filtrated, and the filtrate was concentrated under reduced pressure. And then, the resultant concentrate was distilled under reduced pressure (95° C., 13.3 Pa), to provide 1.9 g of a mixture of bis(1-isopropylamide-2-dimethylaminopropane-N,N') cobalt, bis(2-isopropylamide-1-dimethylaminopropane-N,N') cobalt and (1-isopropylamide-2-dimethylaminopropane-N,N')(2-isopropylamide-1-dimethylaminopropane-N,N') cobalt as a dark brown solid. (Isolation yield: 67%)

Additionally, the mixture of bis(1-isopropylamide-2-dimethylaminopropane-N,N') cobalt, bis(2-isopropylamide-1-dimethylaminopropane-N,N') cobalt and (1-isopropylamide-2-dimethylaminopropane-N,N')(2-isopropylamide-1-dimethylaminopropane-N,N') cobalt was a novel compound, which had the following properties:

Melting point; 90° C.

Cobalt content determined by inductively coupled plasma (ICP) analysis; 16.4 wt % (calculated value; 17.06 wt %)

Reference Example C3

Synthesis of 1-isopropylamino-2-dimethylaminopropane

Into a 200 mL-volume flask equipped with a stirrer, a thermometer and a dropping funnel were placed 12.0 g (75.9 mmol) of the mixture of 1-isopropylamino-2-dimethylaminopropane and 2-isopropylamino-1-dimethylaminopropane (mixture ratio 8:2) prepared in Reference Example C1, and 50 ml of methanol. And then, the mixture was stirred and heated to 60-70° C. Subsequently, a solution of 13.7 g (151.8 mmol) of oxalic acid and 60 ml of methanol was slowly dropped into the flask, and then the mixture was reacted while stirring at 20° C. for 1 hour. The reaction mixture solution was filtrated, and the filtrate was concentrated under reduced pressure. To the resultant concentrate were added 100 ml of water and 17.0 g (303.6 mmol) of potassium hydroxide. And then, the mixture was subjected to extraction with 50 ml of chloroform three times, and the extract was concentrated under reduced pressure. The resultant concentrate was distilled under reduced pressure (105° C., 13.3 kPa), to provide 7.6 g of 1-isopropylamino-2-dimethylaminopropane. (Isolation yield: 76%)

Additionally, 1-isopropylamino-2-dimethylaminopropane had the following properties. The purity was 100%©, determined by $^1$H-NMR.

$^1$H-NMR (CDCl$_3$, δ (ppm)); 0.89 (3H, s), 1.05, 1.07 (each 3H, each d, J=6.3 Hz), 1.75 (1H, drs), 2.20 (6H, s), 2.49 (2, d, J=6.8 Hz), 2.68-2.83 (2H, m)

Reference Example C4

Synthesis of (1-isopropylamide-2-dimethylaminopropane-N,N') lithium

Under argon atmosphere, into a 50 mL-volume flask equipped with a stirrer, a thermometer and a dropping funnel were placed 2.15 g (16.5 mmol) of 1-isopropylamino-2-dimethylaminopropane prepared in Reference Example C3, and 15 ml of hexane. And then, while maintaining the mixture solution at 0° C., 10 ml (16.5 mmol) of 1.65 mold n-butyl lithium/hexane solution was slowly dropped into the flask. After the dropping, the mixture solution was stirred at 0° C. for 30 minutes, and then the mixture was reacted while stirring at 20° C. for 2 hours. After the completion of the reaction, the reaction solution was concentrated under reduced pressure. The resultant concentrate was dried under vacuum, to provide (1-isopropylamide-2-dimethylaminopropane-N,N') lithium.

Additionally, (1-isopropylamide-2-dimethylaminopropane-N,N') lithium was used for the subsequent reaction without any treatment.

Example C2

Synthesis of bis(1-isopropylamide-2-dimethylaminopropane-N,N') cobalt (Cobalt Compound (1c)

Under argon atmosphere, into a 100 mL-volume flask equipped with a stirrer, a thermometer and a dropping funnel were placed 1.07 g (8.25 mmol) of anhydrous cobalt(II) chloride and 20 ml of tetrahydrofuran. And then, the mixture was stirred for 2 hours. Subsequently, while maintaining the solution temperature at 0° C., 20 ml of solution of 1 isopropylamide-2-dimethylaminopropane-N,N')lithium, which was prepared in Reference Example C4, in tetrahydrofuran was slowly dropped into the flask. And then, the mixture was reacted while stirring at 20° C. for 6 hours. After the completion of the reaction, the reaction solution was concentrated under reduced pressure. To the resultant concentrate was added 100 ml of hexane. And then, the mixture was stirred. The mixture was filtrated, and the filtrate was concentrated under reduced pressure. And then, the resultant concentrate was distilled under reduced pressure (95° C., 13.3 Pa), to provide 1.2 g of bis(1-isopropylamide-2-dimethylaminopropane-N,N') cobalt as a dark brown solid. (Isolation yield: 43%)

Reference Example C5

Synthesis of a Mixture of 1-(s-butylamino)-2-dimethylaminopropane and 2-s-butylamino-1-dimethylaminopropane Into a 300 mL-volume flask equipped with a stirrer and a thermometer were placed 25.0 g (158 mmol) of 2-(dimethylamino)propane chloride hydrochloride and 69.4 g (949 mmol) of s-butylamine. And then, the mixture was reacted while stirring at 80-90° C. for 10 hours. After the completion of the reaction, the reaction mixture was filtrated and washed with 200 ml of hexane, and the hexane layer was concentrated under reduced pressure. The resultant concentrate was distilled under reduced pressure (110° C., 11 kPa), to provide 21.7 g of a mixture of 1-(s-butylamino)-2-dimethylaminopropane and 2-s-butylamino-1-dimethylaminopropane (mixture ratio 8:2). (Isolation yield: 87%)

Additionally, the mixture of 1-(s-butylamino)-2-dimethylaminopropane and 2-s-butylamino-1-dimethylaminopropane had the following properties:

$^1$H-NMR (CDCl$_3$, δ (ppm)); 0.95 (9H, m), 1.29 (1H, m), 1.50 (1H, m), 1.70 (1H, br), 2.20 (6H, s), 2.48 (3H, m), 2.73 (1H, m)

Reference Example C6

Synthesis of a Mixture of 1-(s-butylamide)-2-dimethylaminopropane-N,N')lithium and 2-(s-butylamide)-1-dimethylaminopropane-N,N')lithium Under argon atmosphere, into a 50 mL-volume flask equipped with a stirrer, a thermometer and a dropping funnel were placed 2.65 g (16.5 mmol) of the mixture of 1-(s-butylamino)-2-dimethylaminopropane and 2-s-butylamino-1-dimethylaminopropane (mixture ratio 8:2) prepared in Reference Example C5, and 15 ml of hexane. And then, while maintaining the mixture solution at 0° C., 10 ml (16.5 mmol) of 1.65 mol/l n-butyl lithium/hexane solution was slowly dropped into the flask. After the dropping, the mixture solution was stirred at 0° C. for 30 minutes, and then the mixture was reacted while stirring at 20° C. for 2 hours. After the completion of the reaction, the reaction solution was concentrated under reduced pressure. The resultant concentrate was dried under vacuum, to provide a mixture of 1-(s-butylamide)-2-dimethylaminopropane-N,N') lithium and 2-(s-butylamide)-1-dimethylaminopropane-N,N')lithium.

Additionally, the mixture of 1-(s-butylamide)-2-dimethylaminopropane-N,N')lithium and 2-(s-butylamide)-1-dimethylaminopropane-N,N')lithium was used for the subsequent reaction without any treatment.

Example C3

Synthesis of a Mixture of bis(1-(s-butylamide)-2-dimethylaminopropane-N,N')cobalt (Cobalt Compound (1e)), bis(2-(s-butylamide)-1-dimethylaminopropane-N,N')cobalt (Cobalt Compound (1l)) and (1-(s-butylamide)-2-dimethylaminopropane-N,N')(2-(s-butylamide)-1-dimethylaminopropane-N,N')cobalt (Cobalt Compound (1s))

Under argon atmosphere, into a 100 mL-volume flask equipped with a stirrer, a thermometer and a dropping funnel were placed 1.07 g (8.25 mmol) of anhydrous cobalt(II) chloride and 20 ml of tetrahydrofuran. And then, the mixture was stirred for 2 hours. Subsequently, while maintaining the solution temperature at 0° C., 20 ml of solution of the mixture of 1-(s-butylamide)-2-dimethylaminopropane-N,N') lithium and 2-(s-butylamide)-1-dimethylaminopropane-N,N') lithium, which was prepared in Reference Example C6, in tetrahydrofuran was slowly dropped into the flask. And then, the mixture was reacted while stirring at 20° C. for 6 hours. After the completion of the reaction, the reaction solution was concentrated under reduced pressure. To the resultant concentrate was added 100 ml of hexane. And then, the mixture was stirred. The mixture was filtrated, and the filtrate was concentrated under reduced pressure. And then, the resultant concentrate was distilled under reduced pressure (105° C., 13.3 Pa), to provide 2.1 g of a mixture of (bis(1-(s-butylamide)-2-dimethylaminopropane-N,N') cobalt, (bis(2-(s-butylamide)-1-dimethylaminopropane-N,N') cobalt and (1-(s-butylamide)-2-dimethylaminopropane-N,N')(2-(s-butylamide)-1-dimethylaminopropane-N,N') cobalt as a dark brown liquid. (Isolation yield: 68%)

Additionally, the mixture of bis(1-(s-butylamide)-2-dimethylaminopropane-N,N')cobalt, bis(2-(s-butylamide)-1-dimethylaminopropane-N,N')cobalt and (1-(s-butylamide)-2-dimethylaminopropane-N,N')(2-(s-butylamide)-1-dimethylaminopropane-N,N') cobalt was a novel compound, which had the following properties:

Cobalt content determined by inductively coupled plasma (ICP) analysis; 15.3 wt % (calculated value; 15.8 wt %)

Reference Example C7

Synthesis of a Mixture of 1-t-butylamino-2-dimethylaminopropane and 2-t-butylamino-1-dimethylaminopropane

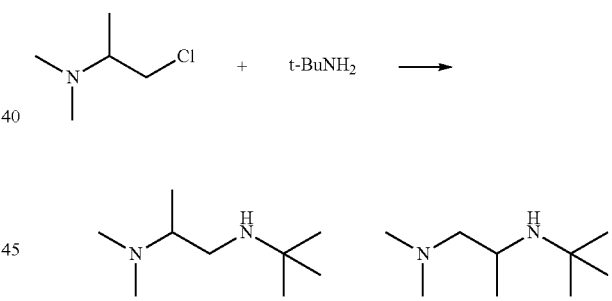

Into a 300 mL-volume flask equipped with a stirrer and a thermometer were placed 25.0 g (158 mmol) of 2-(dimethylamino)propane chloride hydrochloride, 69.4 g (949 mmol) of t-butylamine and 3 ml of water. And then, the mixture was reacted while stirring at 60° C. for 10 hours. After the completion of the reaction, the reaction mixture was filtrated and washed with 200 ml of hexane, and the hexane layer was concentrated under reduced pressure. The resultant concentrate was distilled under reduced pressure (120° C., 12 kPa), to provide 19.2 g of a mixture of 1-t-butylamino-2-dimethylaminopropane and 2-t-butylamino-1-dimethylaminopropane (mixture ratio 8:2). (Isolation yield: 77%)

Additionally, the mixture of 1-t-butylamino-2-dimethylaminopropane and 2-t-butylamino-1-dimethylaminopropane had the following properties:

$^1$H-NMR(CDCl$_3$, δ (ppm)); 0.89 (3H, t, 6.5 Hz), 1.10 (9H, s), 1.40 (1H, brs), 2.18 (6H, s), 2.38 (1H, m), 2.53 (1H, t, 11.0 Hz), 2.48 (3H, m), 2.67-2.77 (1H, m)

Reference Example C8

Synthesis of a Mixture of 1-t-butylamide-2-dimethylaminopropane-N,N')lithium and 2-t-butylamide-1-dimethylaminopropane-N,N')lithium

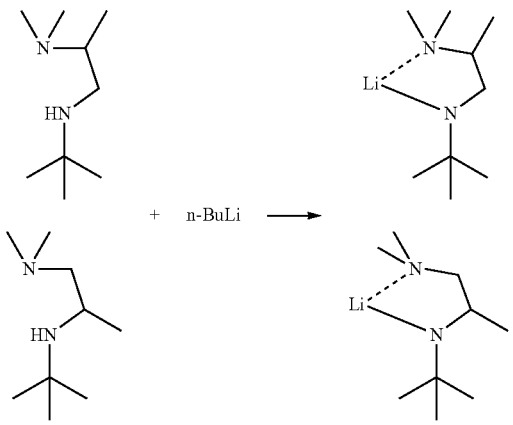

Under argon atmosphere, into a 50 mL-volume flask equipped with a stirrer, a thermometer and a dropping funnel were placed 3.15 g (19.9 mmol) of the mixture of 1-t-butylamino-2-dimethylaminopropane and 2-t-butylamino-1-dimethylaminopropane (mixture ratio 8:2) prepared in Reference Example C7, and 15 ml of hexane. And then, while maintaining the mixture solution at 0° C., 10 ml (16.5 mmol) of 1.65 mol/l n-butyl lithium/hexane solution was slowly dropped into the flask. After the dropping, the mixture solution was stirred at 0° C. for 30 minutes, and then the mixture was reacted while stirring at 20° C. for 2 hours. After the completion of the reaction, the reaction solution was concentrated under reduced pressure. The resultant concentrate was dried under vacuum, to provide a mixture of 1-t-butylamide-2-dimethylaminopropane-N,N')lithium and 2-t-butylamide-1-dimethylaminopropane-N,N')lithium.

Additionally, the mixture of 1-t-butylamide-2-dimethylaminopropane-N,N') lithium and 2-t-butylamide-1-dimethylaminopropane-N,N') lithium was used for the subsequent reaction without any treatment.

Example C4

Synthesis of a Mixture of bis(1-t-butylamide-2-dimethylaminopropane-N,N')cobalt (cobalt compound (1d)), bis(2-t-butylamide-1-dimethylaminopropane-N,N')cobalt (Cobalt Compound (1k)) and (1-t-butylamide-2-dimethylaminopropane-N,N')(2-t-butylamide-1-dimethylaminopropane-N,N')cobalt (Cobalt Compound (1r))

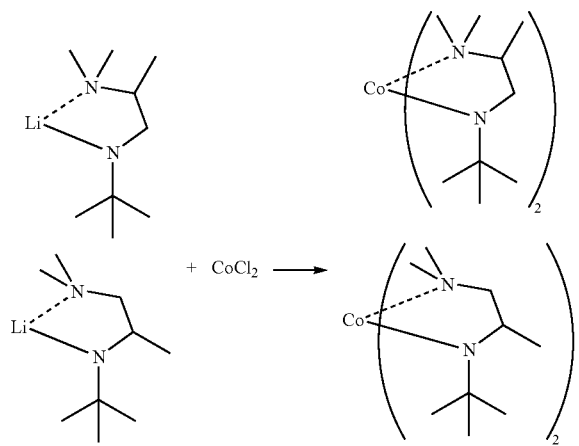

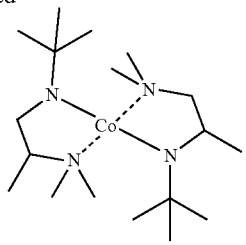

Under argon atmosphere, into a 100 mL-volume flask equipped with a stirrer, a thermometer and a dropping funnel were placed 1.07 g (8.25 mmol) of anhydrous cobalt(II) chloride and 20 ml of tetrahydrofuran. And then, the mixture was stirred for 2 hours. Subsequently, while maintaining the solution temperature at 0° C., 20 ml of solution of the mixture of 1-t-butylamide-2-dimethylaminopropane-N,N') lithium and 2-t-butylamide-1-dimethylaminopropane-N,N') lithium, which was prepared in Reference Example C8, in tetrahydrofuran was slowly dropped into the flask. And then, the mixture was reacted while stirring at 20° C. for 6 hours. After the completion of the reaction, the reaction solution was concentrated under reduced pressure. To the resultant concentrate was added 100 ml of hexane. And then, the mixture was stirred. The mixture was filtrated, and the filtrate was concentrated under reduced pressure. And then, the resultant concentrate was distilled under reduced pressure (115° C., 13.3 Pa), to provide 2.9 g of a mixture of bis(1-t-butylamide-2-dimethylaminopropane-N,N') cobalt, bis(2-t-butylamide-1-dimethylaminopropane-N,N')cobalt and (1-t-butylamide-2-dimethylaminopropane-N,N')(2-t-butylamide-1-dimethylaminopropane-N,N') cobalt as a dark brown solid. (Isolation yield: 94%)

Additionally, the mixture of bis(1-t-butylamide-2-dimethylaminopropane-N,N') cobalt, bis(2-t-butylamide-1-dimethylaminopropane-N,N') cobalt and (1-t-butylamide-2-dimethylaminopropane-N,N')(2-t-butylamide-1-dimethylaminopropane-N,N') cobalt was a novel compound, which had the following properties:

Melting point; 90° C.

Cobalt content determined by inductively coupled plasma (ICP) analysis; 15.0 wt % (calculated value; 15.8 wt %)

Example C5

Vapor-deposition Test; Formation of Cobalt-containing Thin Film

The vapor-deposition tests were conducted by the CVD method in the same way as in Example B5, using the cobalt compound obtained in Example C1, to evaluate the film-forming performance. The vapor-deposition conditions and the film properties were as follows.

(Vapor-deposition Conditions)

Cobalt raw material; the cobalt compound obtained in Example C1

(Mixture of bis(1-isopropylamide-2-dimethylaminopropane-N,N') cobalt (compound (1c)), bis(2-isopropylamide-1-dimethylaminopropane-N,N') cobalt (compound (1j)) and (1-isopropylamide-2-dimethylaminopropane-N,N')(2-isopropylamide-1-dimethylaminopropane-N,N') cobalt (compound (N)))

Vaporization temperature; 90° C.

He carrier gas flow rate; 30 sccm

Ammonia gas flow rate; 10 sccm

Substrate material; SiO$_2$/Si wafer
Substrate temperature; 200° C.
Pressure in the reaction system; 0.67 kPa
Vapor-deposition time; 5 min.
(Film Properties (SEM and XPS-Depth Measurement)
Film thickness; 300 nm
XPS analysis; cobalt film
Carbon content; Not detected
Nitrogen content; Not detected Example C6

Vapor-deposition Test; Formation of Cobalt-containing Thin Film

The vapor-deposition tests were conducted by the CVD method in the same way as in Example B5, using the cobalt compound obtained in Example C2, to evaluate the film-forming performance. The vapor-deposition conditions and the film properties were as follows.
(Vapor-deposition Conditions)
Cobalt raw material; the cobalt compound obtained in Example C2
(Bis(1-isopropylamide-2-dimethylaminopropane-N,N') cobalt (Compound (1c))
Vaporization temperature; 90° C.
He carrier gas flow rate; 30 sccm
Ammonia gas flow rate; 10 sccm
Substrate material; SiO$_2$/Si wafer
Substrate temperature; 200° C.
Pressure in the reaction system; 0.67 kPa
Vapor-deposition time; 5 min.
(Film Properties (SEM and XPS-Depth Measurement))
Film thickness; 300 nm
XPS analysis; cobalt film
Carbon content; Not detected
Nitrogen content; Not detected Example C7

Vapor-deposition Test; Formation of Cobalt-containing Thin Film

The vapor-deposition tests were conducted by the CVD method in the same way as in Example B5, using the cobalt compound obtained in Example C3, to evaluate the film-forming performance. The vapor-deposition conditions and the film properties were as follows.
(Vapor-deposition Conditions)
Cobalt raw material; the cobalt compound obtained in Example C3
(Mixture of bis(1-(s-butylamide)-2-dimethylaminopropane-N,N') cobalt (Compound (1e)), bis(2-(s-butylamide)-1-dimethylaminopropane-N,N') cobalt (Compound (1l)) and (1-(s-butylamide)-2-dimethylaminopropane-N,N')(2-(s-butylamide)-1-dimethylaminopropane-N,N')cobalt (Compound (1s))
Vaporization temperature; 100° C.
He carrier gas flow rate; 30 sccm
Ammonia gas flow rate; 10 sccm
Substrate material; SiO$_2$/Si wafer
Substrate temperature; 200° C.
Pressure in the reaction system; 0.67 kPa
Vapor-deposition time; 5 min.
(Film Properties (SEM and XPS-Depth Measurement))
Film thickness; 200 nm
XPS analysis; cobalt film
Carbon content; Not detected
Nitrogen content; Not detected Example C8

Vapor-deposition Test; Formation of Cobalt-containing Thin Film

The vapor-deposition tests were conducted by the CVD method in the same way as in Example B5, using the cobalt compound obtained in Example C4, to evaluate the film-forming performance. The vapor-deposition conditions and the film properties were as follows.
(Vapor-deposition Conditions)
Cobalt raw material; the cobalt compound obtained in Example C4
(Mixture of bis(1-t-butylamide-2-dimethylaminopropane-N,N')cobalt (Cobalt Compound (1d)), bis(2-t-butylamide-1-dimethylaminopropane-N,N') cobalt (Cobalt Compound (1k)) and (1-t-butylamide-2-dimethylaminopropane-N,N')(2-t-butylamide-1-dimethylaminopropane-N,N')cobalt (Cobalt Compound (1r))
Vaporization temperature; 90° C.
He carrier gas flow rate; 30 sccm
Ammonia gas flow rate; 30 sccm
Substrate material; SiO$_2$/Si wafer
Substrate temperature; 200° C.
Pressure in the reaction system; 0.67 kPa
Vapor-deposition time; 5 min.
(Film Properties (SEM and XPS-Depth Measurement))
Film thickness; 300 nm
XPS analysis; cobalt film
Carbon content; Not detected
Nitrogen content; Not detected Comparative Example C1

(Vapor-deposition Test; Formation of Cobalt-containing Thin Film)
The vapor-deposition tests were conducted by the CVD method in the same way as in Example B5, using bis(N-t-butyl-N'-ethylpropionamidinato) cobalt (the compound disclosed in Patent Document 8), to evaluate the film-forming performance. The vapor-deposition conditions and the film properties were as follows.
(Vapor-deposition Conditions)
Cobalt compound; bis(N-t-butyl-N'-ethylpropionamidinato) cobalt (the compound disclosed in Patent Document 8)
Vaporization temperature; 90° C.
He carrier gas flow rate; 10 sccm
Ammonia gas flow rate; 10 sccm
Substrate material; SiO$_2$/Si wafer
Substrate temperature; 200° C.
Pressure in the reaction system; 0.67 kPa
Vapor-deposition time; 5 min.
(Film Properties (SEM and XPS-Depth Measurement))
Film thickness; 40 nm
XPS analysis; cobalt film
Carbon content; 3% (in terms of carbon atom)
Nitrogen content; 7% (in terms of nitrogen atom)
The results revealed that the bis(amide amino alkane) cobalt compound of the present invention might be a material from which a cobalt-containing thin film might be formed in a short time (high film-forming rate), and from which a high-quality cobalt-containing thin film, which does not contain impurities such as carbon atom and nitrogen atom, might be formed.

Reference Example D1

Synthesis of (1-isopropylamide-2-dimethylaminoethane-N,N') lithium

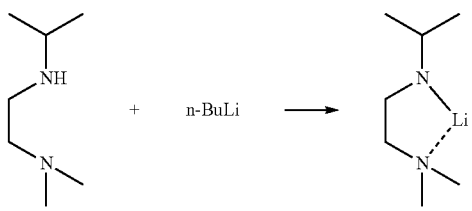

Under argon atmosphere, into a 50 mL-volume flask equipped with a stirrer, a thermometer and a dropping funnel were placed 2.1 g (16 mmol) of 1-isopropylamino-2-dimethylaminoethane and 15 ml of hexane. And then, while maintaining the solution temperature at 0° C., 10 ml (16 mmol) of 1.6 mol/l n-butyl lithium/hexane solution was slowly dropped into the flask, and the mixture was reacted while stirring at the same temperature for 30 minutes and at 20° C. for 2 hours. After the completion of the reaction, the reaction solution was concentrated under reduced pressure. The resultant concentrate was dried under vacuum, to provide 2.1 g of (1-isopropylamide-2-dimethylaminoethane-N,N') lithium. (Isolation yield: 94%)

Additionally, (1-isopropylamide-2-dimethylaminoethane-N,N') lithium had the following properties:

$^1$H-NMR (tetrahydrofuran-d$_8$, δ (ppm)); 2.95 (2H, t, 6.0 Hz), 2.91 (1H, quint, 6.2 Hz), 2.44 (2H, t, 6.0 Hz), 2.18 (6H, s), 0.99 (6H, d, 6.2 Hz)

Example D1

Synthesis of bis(1-isopropylamide-2-dimethylaminoethane-N,N') manganese(II) (Manganese Compound (8)

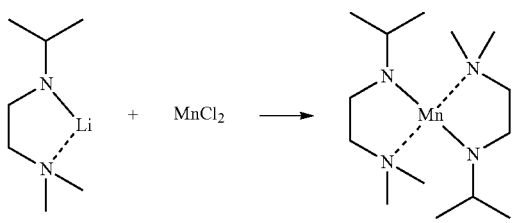

Under argon atmosphere, into a 50 mL-volume flask equipped with a stirrer, a thermometer and a dropping funnel were placed 0.48 g (3.8 mmol) of manganese(II) chloride (pre-dried anhydride) and 10 ml of tetrahydrofuran. And then, these were mixed and the mixture was stirred for 2 hours. Subsequently, while maintaining the solution temperature at 0° C., 10 ml of solution of 1.0 g (7.6 mmol) of (1-isopropylamide-2-dimethylaminoethane-N,N') lithium, which was prepared in the same way as in Reference Example D1, in tetrahydrofuran was slowly dropped into the flask. And then, the mixture was reacted while stirring at 20° C. for 6 hours. After the completion of the reaction, the reaction solution was concentrated under reduced pressure. To the resultant concentrate was added 50 ml of hexane. And then, the mixture was stirred. The mixture was filtrated, and the filtrate was concentrated under reduced pressure. And then, the resultant concentrate was distilled under reduced pressure (80° C., 13.3 Pa), to provide 1.0 g of (bis(1-isopropylamide-2-dimethylaminoethane-N,N') manganese(II) as a light brown liquid. (Isolation yield: 84%)

Additionally, bis(1-isopropylamide-2-dimethylaminoethane-N,N') manganese(II) was a novel compound, which had the following properties:

Manganese content determined by inductively coupled plasma (ICP) analysis; 17.7 wt % (calculated value; 17.5 wt %)

Reference Example D2

Synthesis of 1-(t-butylamino)-2-dimethylaminoethane-N,N')lithium

The reaction was conducted in the same way as in Reference Example D1, except that 2.3 g (16 mmol) of 1-(t-butylamino)-2-dimethylaminoethane was used instead of 1-isopropylamino-2-dimethylaminoethane, to provide 2.4 g of 1-(t-butylamino)-2-dimethylaminoethane-N,N')lithium. (Isolation yield: 96%)

Example D2

Synthesis of bis(1-(t-butylamide)-2-dimethylaminoethane-N,N') manganese(II) (Manganese Compound (9)

The reaction was conducted in the same way as in Example D1, except that 10 ml of solution of 1.1 g (7.6 mmol) of 1-(t-butylamino)-2-dimethylaminoethane-N,N') lithium in tetrahydrofuran was used instead of the solution of (1-isopropylamide-2-dimethylaminoethane-N,N')lithium in tetrahydrofuran. Then, the reaction solution was concentrated, and the resultant concentrate was sublimed under reduced pressure (90° C., 13 Pa), to provide 1.1 g of bis(1-(t-butylamide)-2-dimethylaminoethane-N,N') manganese as a light greenish brown solid. (Isolation yield: 85%)

Additionally, bis(1-(t-butylamide)-2-dimethylaminoethane-N,N') manganese(II) was a novel compound, which had the following properties:

Melting point; 70-71° C.

Manganese content determined by inductively coupled plasma (ICP) analysis; 16.5 wt % (calculated value; 16.1 wt %)

Example D3

Vapor-deposition Test; Formation of Manganese-Containing Thin Film

The vapor-deposition tests were conducted by the CVD method, using bis(1-(t-butylamide)-2-dimethylaminoethane-N,N') manganese(II) (manganese compound (9)) obtained in Example D2, to evaluate the film-forming performance.

The apparatus shown in FIG. 2 was used to conduct the evaluation tests. The manganese compound 20 in a vaporizer (glass ampule) 3 is heated by means of a heater 10B and vaporized, and discharged from the vaporizer 3, together with a helium gas which is fed via a mass flow controller 1a after pre-heating by a pre-heater 10A. The gas discharged from the vaporizer 3 is fed into a reactor 4, together with a reactive gas such as an ammonia gas or a hydrogen gas and an oxygen gas, which is fed via a mass flow controller 1B and a stop valve 2. The pressure in the reaction system is controlled to a predetermined pressure by opening and closing a valve 6, which is provided upstream of a vacuum pump, and is monitored by a pressure gauge 5. The central part of the reactor can be heated by a heater 10C. The manganese compound, which is fed into the reactor, is reduced, or oxidized and thermally-decomposed on a surface of a substrate 21 which is placed in the central part of the reactor and heated to a predetermined temperature by the heater 10C, to deposit a manganese-containing thin film on the substrate 21. The gas discharged from the reactor 4 is exhausted to the atmosphere via a trap 7 and the vacuum pump.

The vapor-deposition conditions and the film properties were as follows. The rectangular substrate of 6 mm×20 mm was used as the substrate on which the film was vapor-deposited.

(Vapor-deposition Conditions 1)
Manganese raw material; bis(1-(t-butylamide)-2-dimethylaminoethane-N,N') manganese(II) (Manganese Compound (9))
Vaporization temperature; 50° C.
He carrier gas flow rate; 60 sccm
Hydrogen gas flow rate; 10 sccm
Substrate material; Si wafer
Substrate temperature; 300° C.
Pressure in the reaction system; 1.33 kPa
Vapor-deposition time; 30 min.
(Film Properties (SEM and XPS-Depth Measurement, and Resistivity Determined by Four-Probe Method)
Film thickness; 100 nm
XPS analysis; manganese film
Resistivity; $(1.6$-$1.9)\times 10^{-6}$ $\Omega$m
(Vapor-deposition Conditions 2)
Manganese raw material; bis(1-(t-butylamide)-2-dimethylaminoethane-N,N') manganese(II) (manganese compound (9))
Vaporization temperature; 50° C.
He carrier gas flow rate; 60 sccm
  Ammonia gas flow rate; 10 sccm
Substrate material; $SiO_2$ wafer
Substrate temperature; 200° C.
Pressure in the reaction system; 1.33 kPa
Vapor-deposition time; 30 min.
(Film Properties (Appearance Observation))
Appearance of film; Mn-containing film with metallic luster was formed.

Comparative Example D1

(Vapor-deposition Test; Formation of Manganese-Containing Thin Film)
The vapor-deposition tests were conducted by the CVD method in the same way as in Example D3, using bis(N,N'-diisopropylpentaneamidinato) manganese (the compound disclosed in Non-Patent Documents 9 and 10), to evaluate the film-forming performance. The vapor-deposition conditions and the film properties were as follows.
(Vapor-deposition Conditions 3)
Vaporization temperature; 70° C.
He carrier gas flow rate; 60 sccm
Hydrogen gas flow rate; 10 sccm
Substrate material; Si wafer
Substrate temperature; 300° C.
Pressure in the reaction system; 1.33 kPa
Vapor-deposition time; 30 min.
A film was not formed under the conditions substantially similar to Example D3 (Vapor-deposition conditions 3).
(Vapor-deposition Conditions 4)
Vaporization temperature; 70° C.
He carrier gas flow rate; 60 sccm
Hydrogen gas flow rate; 10 sccm
Substrate material; Si wafer
Substrate temperature; 350° C.
Pressure in the reaction system; 1.33 kPa
Vapor-deposition time; 30 min.
(Film Properties (Film Thickness, and Resistivity Determined by Four-Probe Method)
Film thickness; 10 nm or less
Resistivity; Unmeasurable The results revealed that the bis(amide amino alkane) manganese compound of the present invention might be a material from which a manganese-containing thin film might be formed at a lower temperature and in a short time (high film-forming rate), and from which a high-quality manganese-containing thin film having a lower resistivity (which does not contain impurities such as carbon atom) might be formed.

Example E1

Synthesis of bis(1-isopropylamide-2-dimethylaminoethane-N,N') zinc(II)

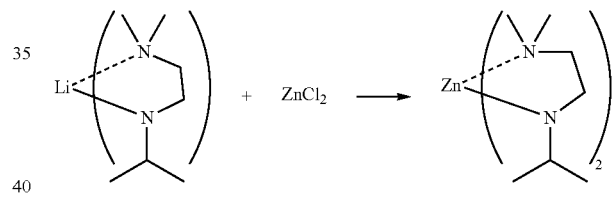

Under argon atmosphere, into a 50 mL-volume flask equipped with a stirrer, a thermometer and a dropping funnel were placed 0.52 g (3.8 mmol) of zinc(II) chloride (pre-dried anhydride) and 10 ml of tetrahydrofuran. And then, these were mixed and the mixture was stirred for 2 hours. Subsequently, while maintaining the solution temperature at 0° C., 10 ml of solution of 1.0 g (7.6 mmol) of (1-isopropylamide-2-dimethylaminoethane-N,N') lithium, which was prepared in the same way as in Reference Example D1, in tetrahydrofuran was slowly dropped into the flask. And then, the mixture was reacted while stirring at 20° C. for 6 hours. After the completion of the reaction, the reaction solution was concentrated under reduced pressure. To the resultant concentrate was added 50 ml of hexane. And then, the mixture was stirred. The mixture was filtrated, and the filtrate was concentrated under reduced pressure. And then, the resultant concentrate was distilled under reduced pressure (80° C., 13.3 Pa), to provide 1.1 g of (bis(1-isopropylamide-2-dimethylaminoethane-N,N') zinc(II) as a colorless and transparent liquid. (Isolation yield: 89%)

Additionally, bis(1-isopropylamide-2-dimethylaminoethane-N,N') zinc(II) was a novel compound, which had the following properties:

$^1$H-NMR (tetrahydrofuran-$d_8$, δ (ppm)); 3.01 (4H, t, 6.0 Hz), 2.91 (2H, quint, 6.2 Hz), 2.52 (4H, t, 6.0 Hz), 2.27 (12H, s), 1.03 (12H, d, 6.2 Hz)

Zinc content determined by inductively coupled plasma (ICP) analysis; 19.8 wt % (calculated value; 20.2 wt %)

Example E2

Synthesis of bis(1-(t-butylamide)-2-dimethylamino-ethane-N,N') zinc(II)

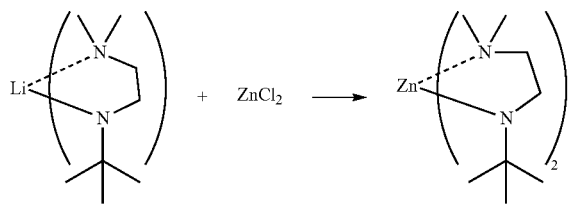

The reaction was conducted in the same way as in Example E1, except that 10 ml of solution of 1.1 g (7.6 mmol) of 1-(t-butylamino)-2-dimethylaminoethane-N,N')lithium, which was prepared in the same way as in Reference Example D2, in tetrahydrofuran was used instead of the solution of (1-isopropylamide-2-dimethylaminoethane-N,N') lithium in tetrahydrofuran. Then, the reaction solution was concentrated, and the resultant concentrate was sublimed under reduced pressure (90° C., 13 Pa), to provide 1.2 g of bis(1-(t-butylamide)-2-dimethylaminoethane-N,N') zinc(II) as a white solid. (Isolation yield: 90%)

Additionally, bis(1-(t-butylamide)-2-dimethylaminoethane-N,N') zinc(II) was a novel compound, which had the following properties:

$^1$H-NMR (tetrahydrofuran-$d_8$, δ (ppm)); 3.03 (4H, t, 6.0 Hz), 2.50 (4H, t, 6.0 Hz), 2.26 (12H, s), 1.11 (18H, s)

Melting point; 98-100° C.

Zinc content determined by inductively coupled plasma (ICP) analysis; 18.5 wt % (calculated value; 18.6 wt %)

Example E3

Vapor-deposition Test; Formation of Zinc-Containing Thin Film

The vapor-deposition tests were conducted by the CVD method in the same way as in Example D3, using (bis(1-isopropylamide-2-dimethylaminoethane-N,N') zinc(II)) obtained in Example E1, to evaluate the film-forming performance. The vapor-deposition conditions and the film properties were as follows.

(Vapor-deposition Conditions 1)

Zinc raw material; the zinc compound obtained in Example E1
(bis(1-isopropylamide-2-dimethylaminoethane-N,N') zinc(II))
Vaporization temperature; 40° C.
He carrier gas flow rate; 100 sccm
Oxygen gas flow rate; 10 sccm
Substrate material; SiO$_2$ wafer
Substrate temperature; 300° C.
Pressure in the reaction system; 1.33 kPa
Vapor-deposition time; 30 min.
(Film Properties (XPS-Depth Measurement))
Film thickness; 50 nm or more
XPS analysis; zinc oxide film
Carbon content; Not detected
Nitrogen content; Not detected Comparative Example E1

(Vapor-deposition Test; Formation of Zinc-Containing Thin Film)

The vapor-deposition tests were conducted by the CVD method in the same way as in Example E3, using bis(acetylacetonato)zinc (the compound disclosed in Patent Document 14), to evaluate the film-forming performance. The vapor-deposition conditions and the film properties were as follows.

(Vapor-deposition Conditions 2)
Vaporization temperature; 50° C.
He carrier gas flow rate; 30 sccm
Oxygen gas flow rate; 10 sccm
Substrate material; SiO$_2$ wafer
Substrate temperature; 300° C.
Pressure in the reaction system; 1.33 kPa
Vapor-deposition time; 30 min.

A film was not formed under the conditions substantially similar to Example E3 (Vapor deposition conditions 2).

(Vapor-deposition Conditions 3)
Vaporization temperature; 50° C.
He carrier gas flow rate; 30 sccm
Oxygen gas flow rate; 10 sccm
Substrate material; SiO$_2$ wafer
Substrate temperature; 450° C.
Pressure in the reaction system; 1.33 kPa
Vapor-deposition time; 30 min,
(Film Properties (XPS-Depth Measurement)
Film thickness; 50 nm or more
XPS analysis; zinc oxide film
Carbon content; 5% (in terms of carbon atom)
Nitrogen content; Not detected (the raw material does not contain a nitrogen atom at all.)

The results revealed that a high-quality zinc-containing thin film (zinc oxide film), which does not contain impurities such as carbon atom and nitrogen atom, might be formed using the bis(amide amino alkane) zinc compound of the present invention.

Example F1

Synthesis of bis(1-isopropylamide-2-dimethylamino-ethane-N,N') iron(II)

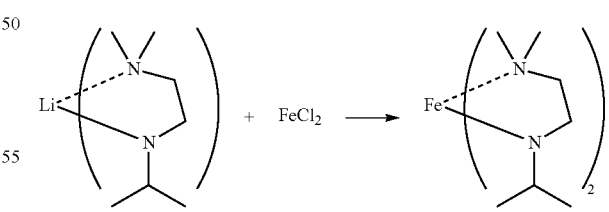

Under argon atmosphere, into a 50 mL-volume flask equipped with a stirrer, a thermometer and a dropping funnel were placed 0.48 g (3.8 mmol) of iron(II) chloride (pre-dried anhydride) and 10 ml of tetrahydrofuran. And then, these were mixed and the mixture was stirred for 2 hours. Subsequently, while maintaining the solution temperature at 0° C., 10 ml of solution of 1.0 g (7.6 mmol) of 1-isopropylamide-2-dimethylaminoethane-N,N') lithium, which was prepared in the same way as in Reference Example D1, in tetrahydrofuran was slowly dropped into the flask. And then, the mixture was reacted while stirring at 20° C. for 6 hours. After the completion of the reaction, the reaction solution was concentrated under reduced pressure. To the resultant concentrate was added 50 ml of hexane. And then, the mixture was stirred. The mixture was filtered, and the filtrate was concentrated under reduced pressure. And then, the resultant concentrate was distilled under reduced pressure (80° C., 13.3 Pa), to provide 1.0 g of (bis(1-isopropylamide-2-dimethylaminoethane-N,N') iron(II) as a brown transparent liquid. (Isolation yield: 84%)

Additionally, (bis(1-isopropylamide-2-dimethylaminoethane-N,N') iron(II) was a novel compound, which had the following properties:

Iron content determined by inductively coupled plasma (ICP) analysis; 18.2 wt % (calculated value; 17.8 wt %)

Example G1

Synthesis of bis(1-(t-butylamide)-2-dimethylamino-ethane-N,N') nickel

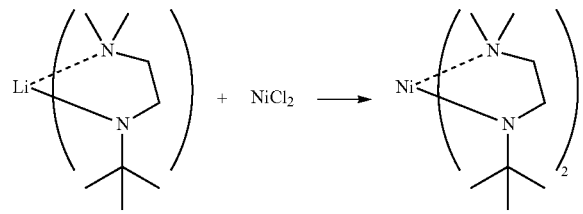

The reaction was conducted in the same way as in Example E2, except that 0.49 g (3.8 mmol) of nickel(II) chloride was used instead of zinc(II) chloride. Then, the reaction solution was concentrated, and the resultant concentrate was sublimed under reduced pressure (90° C., 13 Pa), to provide 0.80 g of bis(1-(t-butylamide)-2-dimethylaminoethane-N,N') nickel as a brown solid. (Isolation yield: 61%)

Additionally, bis(1-(t-butylamide)-2-dimethylaminoethane-N,N') nickel(II) was a novel compound, which had the following properties:

Melting point; 90-92° C.

Nickel content determined by inductively coupled plasma (ICP) analysis; 17.4 wt %© (calculated value; 17.0 wt %)

Reference Example H1

Synthesis of (1-methylamide-2-dimethylaminoethane-N,N')lithium

The reaction was conducted in the same way as in Reference Example D1, except that 1.6 g (16 mmol) of 1-methylamino-2-dimethylaminoethane was used instead of 1-isopropylamino-2-dimethylaminoethane, to provide 1.6 g of (1-methylamide-2-dimethylaminoethane-N,N')lithium. (Isolation yield: 92%)

Example H1

Synthesis of tris(1-methylamide-2-dimethylaminoethane-N,N') indium(III)

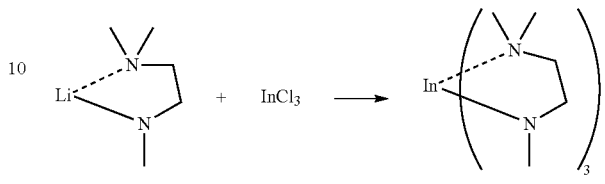

Under argon atmosphere, into a 50 mL-volume flask equipped with a stirrer, a thermometer and a dropping funnel were placed 0.84 g (3.8 mmol) of indium(III) chloride (pre-dried anhydride) and 10 ml of tetrahydrofuran. And then, these were mixed and the mixture was stirred for 2 hours. Subsequently, while maintaining the solution temperature at 0° C., 10 ml of solution of 1.1 g (11 mmol) of (1-methylamide-2-dimethylaminoethane-N,N') lithium, which was prepared in Reference Example H1, in tetrahydrofuran was slowly dropped into the flask. And then, the mixture was reacted while stirring at 20° C. for 6 hours. After the completion of the reaction, the reaction solution was concentrated under reduced pressure. To the resultant concentrate was added 50 ml of hexane. And then, the mixture was stirred. The mixture was filtered, and the filtrate was concentrated under reduced pressure. And then, the resultant concentrate was distilled under reduced pressure (130° C., 13.3 Pa), to provide 1.2 g of tris(1-methylamide-2-dimethylaminoethane-N,N') indium(III) as a light yellow semi-solid (wax). (Isolation yield: 75%)

Additionally, tris(1-methylamide-2-dimethylaminoethane-N,N') indium(III) was a novel compound, which had the following properties:

$^1$H-NMR (tetrahydrofuran-$d_8$, δ (ppm)); 2.95 (6H, t, 5.6 Hz), 2.83 (9H, s), 2.44 (6H, t, 5.6 Hz), 2.26 (18H, s)

Indium content determined by inductively coupled plasma (ICP) analysis; 26.8 wt % (calculated value; 27.5 wt %)

Example I1

Synthesis of (1-methylamide-2-dimethylaminoethane-N,N')sodium

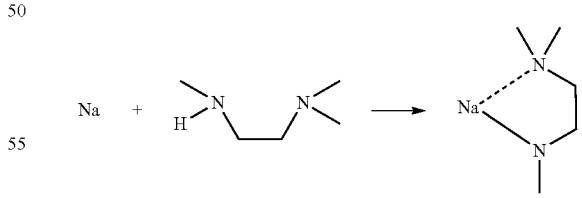

Under argon atmosphere, into a 50 mL-volume flask equipped with a stirrer, a thermometer and a dropping funnel were placed 0.21 g (9.0 mmol) of metallic sodium, 1.0 g (10 mmol) of 1-methylamino-2-dimethylaminoethane, 1.4 g (20 mmol) of isoprene and 25 ml of hexane at 20° C. And then, the mixture was stirred at the same temperature for 20 hours. After the completion of the reaction, under argon atmosphere, the reaction solution was filtered, and the precipitate was washed with 20 ml of hexane. And then, the precipitate was dried under vacuum, to provide 0.9 g of (1-methylamide-2-dimethylaminoethane-N,N') sodium. (Isolation yield: 80%)

Additionally, (1-methylamide-2-dimethylaminoethane-N,N')sodium was a novel compound, which had the following properties:

$^1$H-NMR (tetrahydrofuran-d$_8$, δ (ppm)); 2.98 (2H, t, 6.0 Hz), 2.97 (3H, s), 2.42 (2H, t, 6.0 Hz), 2.16 (6H, s)

Example J1

Synthesis of tris(1-methylamide-2-dimethylaminoethane-N,N') yttrium(III)

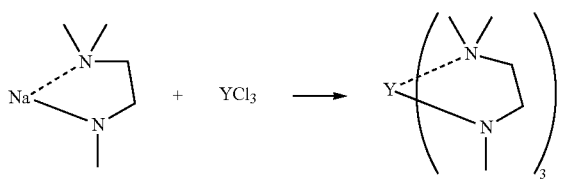

Under argon atmosphere, into a 50 mL-volume flask equipped with a stirrer, a thermometer and a dropping funnel were placed 0.74 g (3.8 mmol) of yttrium(III) chloride (pre-dried anhydride) and 10 ml of tetrahydrofuran. And then, these were mixed and the mixture was stirred for 2 hours. Subsequently, while maintaining the solution temperature at 0° C., 10 ml of solution of 1.4 g (11 mmol) of (1-methylamide-2-dimethylaminoethane-N,N') sodium, which was prepared in Example I1, in tetrahydrofuran was slowly dropped into the flask. And then, the mixture was reacted while stirring at 20° C. for 6 hours. After the completion of the reaction, the reaction solution was concentrated under reduced pressure. To the resultant concentrate was added 50 ml of hexane. And then, the mixture was stirred. The mixture was filtrated, and the filtrate was concentrated under reduced pressure. And then, the resultant concentrate was distilled under reduced pressure (140° C., 13.3 Pa), to provide 0.60 g of (tris(1-methylamide-2-dimethylaminoethane-N,N') yttrium(III) as a light yellow semi-solid (wax). (Isolation yield: 40%)

Additionally, tris(1-methylamide-2-dimethylaminoethane-N,N') yttrium(III) was a novel compound, which had the following properties:

$^1$H-NMR (tetrahydrofuran-d$_8$, δ (ppm)); 2.49 (6H, t, 6.0 Hz), 2.30 (9H, s), 2.26 (6H, t, 6.0 Hz), 2.14 (18H, s)

Yttrium content determined by inductively coupled plasma (ICP) analysis; 21.9 wt % (calculated value; 22.7 wt %)

Example K1

Synthesis of tris(1-methylamide-2-dimethylaminoethane-N,N') lanthanum(III)

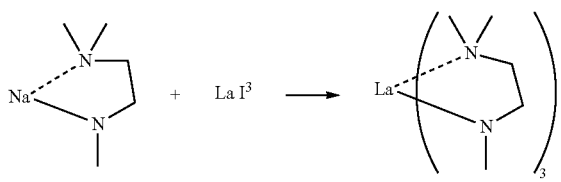

Under argon atmosphere, into a 50 mL-volume flask equipped with a stirrer, a thermometer and a dropping funnel were placed 1.97 g (3.8 mmol) of lanthanum(III) iodide (pre-dried anhydride) and 20 ml of tetrahydrofuran. And then, these were mixed and the mixture was stirred for 2 hours. Subsequently, while maintaining the solution temperature at 0° C., 10 ml of solution of 1.4 g (11 mmol) of (1-methylamide-2-dimethylaminoethane-N,N') sodium, which was prepared in Example I1, in tetrahydrofuran was slowly dropped into the flask. And then, the mixture was reacted while stirring at 20° C. for 6 hours. After the completion of the reaction, the reaction solution was concentrated under reduced pressure. To the resultant concentrate was added 50 ml of hexane. And then, the mixture was stirred. The mixture was filtrated, and the filtrate was concentrated under reduced pressure. And then, the resultant concentrate was distilled under reduced pressure (140° C., 13.3 Pa), to provide 0.50 g of (tris(1-methylamide-2-dimethylaminoethane-N,N')lanthanum(III) as a light yellow semi-solid (wax). (Isolation yield: 30%)

Additionally, tris(1-methylamide-2-dimethylaminoethane-N,N') lanthanum(III) was a novel compound, which had the following properties:

$^1$H-NMR (tetrahydrofuran-d$_8$, δ (ppm)); 2.90 (6H, t, 6.0 Hz), 2.84 (9H, s), 2.70 (6H, t, 6.0 Hz), 2.31 (18H, s)

Lanthanum content determined by inductively coupled plasma (ICP) analysis; 30.2 wt % (calculated value; 31.4 wt %)

INDUSTRIAL APPLICABILITY

According to the present invention, there may be provided a novel (amide amino alkane) metal compound from which a metal-containing thin film may be produced by a simple method. There may be also provided a method of producing a metal-containing thin film on an object by a CVD method using the metal compound. The (amide amino alkane) metal compound of the present invention is suitable for the formation of metal-containing thin film by a CVD method, and therefore is suitable for industrial use.

The bis(amide amino alkane) magnesium compound is useful as a material for the formation of magnesium-containing thin film, a polymerization catalyst, and a material for the production of medicines, agricultural chemicals, and the like, for example. The bis(amide amino alkane) cobalt compound is useful as a material for the formation of cobalt-containing thin film, a polymerization catalyst, and a material for the production of medicines, agricultural chemicals, and the like, for example.

The bis(amide amino alkane) manganese compound is useful as a material for the formation of manganese-containing thin film, a polymerization catalyst, and a material for the production of medicines, agricultural chemicals, and the like, for example. The bis(amide amino alkane) zinc compound is useful as a material for the formation of manganese-containing thin film, a polymerization catalyst, and a material for the production of medicines, agricultural chemicals, and the like, for example.

DESCRIPTION OF THE MAIN SYMBOLS (FIG. 1)
1. Carrier gas (He)
2. Diluting gas (He)
3. Reactive gas (O$_2$)
4. Mass flow controller
5. Mass flow controller
6. Mass flow controller
7. Container for magnesium raw material (vaporizer)
8. Thermostatic bath 9. Reactor
10. Substrate
11. Heater for reactor
12. Pressure gauge
13. Trap
14. Vacuum pump
(FIG. 2)
3. Vaporizer
4. Reactor
10B. Heater for vaporizer
10C. Heater for reactor
20. Raw material, (amide amino alkane) metal compound
21. Substrate

The invention claimed is:

1. An (amide amino alkane) metal compound represented by the formula (1);

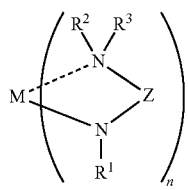
(1)

wherein
M represents a metal atom;
R$^1$ represents a linear, branched or cyclic alkyl group having 1 to 6 carbon atoms;
R$^2$ and R$^3$ may be the same as, or different from each other, and each independently represents a linear or branched alkyl group having 1 to 3 carbon atoms, or R$^2$ and R$^3$ may form a substituted or unsubstituted 5- or 6-membered ring together with the nitrogen atom to which they are bound;
Z represents a linear or branched alkylene group having 1 to 10 carbon atoms (a part of which may optionally form a ring); and
n represents a number of the ligands, which is equal to the valence of the metal (M), and represents an integer of from 1 to 3;
with the proviso that
the metal compounds in which M is Li (Lithium), Be (Beryllium), Ge (Germanium) or Nd (Neodymium) are excluded;
the metal compounds in which M is Mg (Magnesium) and R$^1$ is methyl group are excluded;
the metal compounds in which M is Zn (Zinc) and R$^1$ is methyl group are excluded;
the metal compounds in which M is Bi (Bismuth) and R$^1$ is t-butyl group are excluded; and
in cases where n is two or greater, two or more ligands may be the same as, or different from each other.

2. The (amide amino alkane) metal compound as claimed in claim 1, wherein M is sodium, magnesium, manganese, iron, cobalt, nickel, zinc, yttrium, lanthanum, or indium.

3. The (amide amino alkane) metal compound as claimed in claim 1, wherein Z is a linear or branched alkylene group having 1 to 5 carbon atoms, or a group represented by the formula:

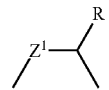

wherein
Z$^1$ represents a linear alkylene group having 1 to 3 carbon atoms, and
R represents a linear or branched alkyl group having 1 to 6 carbon atoms, or a cycloalkyl group having 3 to 6 carbon atoms.

4. A method of producing an (amide amino alkane) metal compound as claimed in claim 1, which is represented by the formula (1):

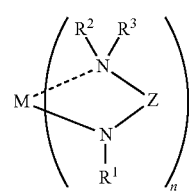
(1)

wherein M, R$^1$, R$^2$, R$^3$, Z and n are defined as above;
comprising a step of;
reacting a mono- or di-alkyl metal compound represented by the formula (2a) or (2b):

R$^4$M (2a)

R$^4$R$^5$M (2b)

wherein
M represents a metal atom; and
R$^4$ and R$^5$ may be the same as, or different from each other, and each independently represents a linear or branched alkyl group having 1 to 10 carbon atoms;
with a di-amino alkane compound represented by the formula (3):

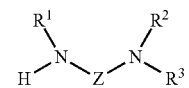
(3)

wherein R$^1$, R$^2$, R$^3$ and Z are defined as above.

5. A method of producing an (amide amino alkane) metal compound as claimed in claim 1, which is represented by the formula (1);

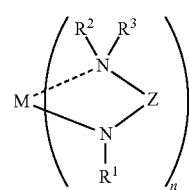
(1)

wherein M, R$^1$, R$^2$, R$^3$, Z and n are defined as above;
comprising steps of
reacting an alkyl alkali metal compound represented by the formula (4a);

R$^4$A (4a)

wherein
R$^4$ represents a linear or branched alkyl group having 1 to 10 carbon atoms; and
A represents an alkali metal atom;
or an alkali metal with a di-amino alkane compound represented by the formula (3):

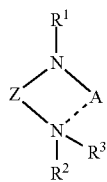
(3)

wherein R$^1$, R$^2$, R$^3$ and Z are defined as above;
to form a (amide amino alkane) alkali metal compound represented by the formula (5):

(5)

wherein R$^1$, R$^2$, R$^3$, A and Z are defined as above; and
reacting the (amide amino alkane) alkali metal compound with a metal halide compound represented by the formula (6):

MX$_n$ (6)

wherein
M represents a metal atom;
X represents a halogen atom; and
n represents a number of the halogen atoms, which is equal to the valence of the metal (M), and represents an integer of from 1 to 3.

6. A method of producing an (amide amino alkane) metal compound as claimed in claim 1, which is represented by the formula (1):

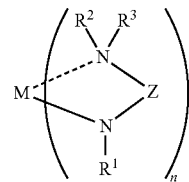
(1)

wherein R$^1$, R$^2$, R$^3$, M, Z and n are defined as above;
comprising a step of:
reacting a metal represented by the formula (7):

M (7)

wherein
M represents a metal atom, and is defined as above;
with a di-amino alkane compound represented by the formula (3):

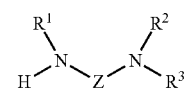
(3)

wherein R$^1$, R$^2$, R$^3$ and Z are defined as above.

7. A method of producing a metal-containing thin film by a chemical vapor deposition method, wherein an (amide amino alkane) metal compound as claimed in claim 1 is used as a source.

8. A material for forming a metal-containing thin film, comprising an (amide amino alkane) metal compound as claimed in claim 1.

\* \* \* \* \*